(12) United States Patent
Mackerell, Jr. et al.

(10) Patent No.: US 8,785,499 B2
(45) Date of Patent: Jul. 22, 2014

(54) TARGETING NAD BIOSYNTHESIS IN BACTERIAL PATHOGENS

(75) Inventors: Alexander Mackerell, Jr., Baltimore, MD (US); Hong Zhang, Dallas, TX (US); Andrei Osterman, San Diego, CA (US); Rohit Kolhatkar, Loves Park, IL (US)

(73) Assignees: University of Maryland, Baltimore, Baltimore, MD (US); The Board of Regents of the University of Texas System, Austin, TX (US); Sanford-Burnham Medical Research Institute, La Jolla, CA (US)

( * ) Notice: Subject to any disclaimer, the term of this patent is extended or adjusted under 35 U.S.C. 154(b) by 228 days.

(21) Appl. No.: 13/383,340

(22) PCT Filed: Jul. 12, 2010

(86) PCT No.: PCT/US2010/041708
§ 371 (c)(1),
(2), (4) Date: Apr. 10, 2012

(87) PCT Pub. No.: WO2011/006158
PCT Pub. Date: Jan. 13, 2011

(65) Prior Publication Data
US 2012/0190708 A1    Jul. 26, 2012

Related U.S. Application Data

(60) Provisional application No. 61/224,504, filed on Jul. 10, 2009.

(51) Int. Cl.
*A61K 31/165* (2006.01)

(52) U.S. Cl.
USPC ........................... 514/615; 514/614; 564/151

(58) Field of Classification Search
USPC .................................. 564/151; 514/614, 615
See application file for complete search history.

(56) References Cited

U.S. PATENT DOCUMENTS

2007/0037752 A1*  2/2007  Ansorge et al. ................. 514/18
2009/0312363 A1  12/2009  Bradner et al.

FOREIGN PATENT DOCUMENTS

WO         2008091349 A1     7/2008

OTHER PUBLICATIONS

Sorci et al, Chemistry and Biology, 2009, 16(8), 849-861.*
J. Finn et al. "Identification of novel inhibitors of methionyl-tRNA synthetase (MetRS) by virtual screening," Bioorganic & Medicinal Chemistry Letters 18, 2008, pp. 3932-3937, cited in ISR.
A. K. Halve et al. "N/C-4 substituted azetidin-2-ones: Synthesis and preliminary evaluation as new class of antimicrobial agents," Bioorganic & Medicinal Chemistry Letters 17, 2007, pp. 341-345, cited in IRS.
P. V. Desai et al. "Identification of Novel Parasitic Cysteine Protease Inhibitors Using Virtual Screening. 1. The ChemBridge Datebase," Journal of Medicinal Chemistry 2004, No. 47, pp. 6609-6615, cited in ISR.
H. J. Yoon et al."Crystal Structure of Nicotinic Acid Mononucleotide Adenylyltransferase from *Pseudomonas aeruginosa* in its Apo and Substrate-complexed Forms Reveals a Fully Open Conformation," Journal of Medicinal Chemistry, 2005, No. 351, pp. 258-265.
S. Lu et al. "Structure of nicotinic acid mononucleotide adenylyltransferase from *Bacillus anthracis*," Structural Biology and Crystalization Communications, 2008, No. 64, pp. 893-898.
H. Zhang et al. "Crystal Structures of *E. coli* Nicotinate Mononucleotide Adenylyltransferase and its Complex with Deamido-NAD," Structure, Vo. 10, Jan. 2002, pp. 69-79.
A. M. Olland et al. "Identification, Characterization, and Crystal Structure of *Bacillus subtilis* Nicotinic Acid Mononucleotide Adenylyltransferase," The Journal of Biological Chemistry, vol. 277, No. 5, Feb. 1, 2002, pp. 3698-3707.
S. Han et al. "Crystal Structure of Nicotinic Mononucleotide Adenylyltransferase from *Staphyloccocus aureus*: Structural Basis for NaAD Interaction in Functional Dimer," Journal of Mol. Biol., 2006, No. 360, pp. 814-825.
V. C. Sershon et al. "Kinetic and X-Ray Structural Evidence for Negative Cooperativity in Substrate Binding to Nicotinate Mononucleotide Adenylyltransferase (NMAT) from *Bacillus anthracis*," Journal of Mol. Biol. 2009, No. 385, pp. 867-888.
International Search Report of PCT/US2010/041708, date of mailing Mar. 28, 2011.
Written Opinion of PCT/US2010/041708, date of mailing Mar. 28, 2011.
L. Sorci et al. "Targeting NAD Biosynthesis in Bacterial Pathogens: Structure-Based Development of Inhibitors of Nicotinate Mononucleotide Adenylyltransferase NadD," Chemistry & Biology 16, Aug. 28, 2009, pp. 849-861.
L. Sorci et al. "Targeting Nad Biosynthesis in Bacterial Pathogens: Structure-Based Development of Inhibitors of Nicotinate Mononucleotide Adenylyltransferase NadD," Chemistry & Biology 16, Aug. 28, 2009, Supplemental Data.

* cited by examiner

*Primary Examiner* — Shailendra Kumar
(74) *Attorney, Agent, or Firm* — Westerman, Hattori, Daniels & Adrian, LLP

(57) ABSTRACT

The emergence of multidrug-resistant pathogens necessitates the search for new antibiotics acting on previously unexplored targets. Nicotinate mononucleotide adenylyltransferase of the NadD family, an essential enzyme of NAD biosynthesis in most bacteria, was selected as a target for structure-based inhibitor development. To this end, the inventors have identified small molecule compounds that inhibit bacterial target enzymes by interacting with a novel inhibitory binding site on the enzyme while having no effect on functionally equivalent human enzymes.

6 Claims, 18 Drawing Sheets

Figure 6
A
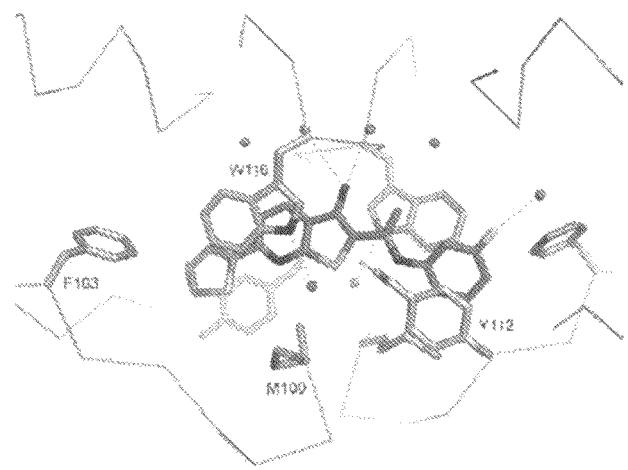
B.
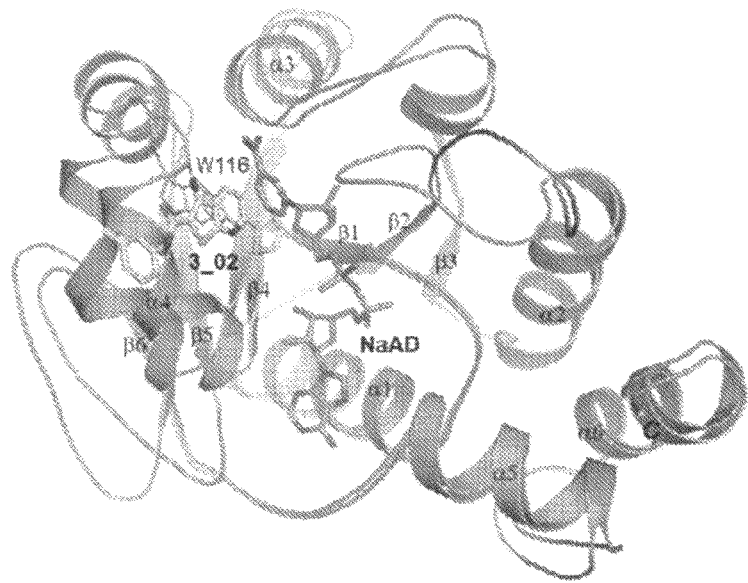

Figure 7
A
B
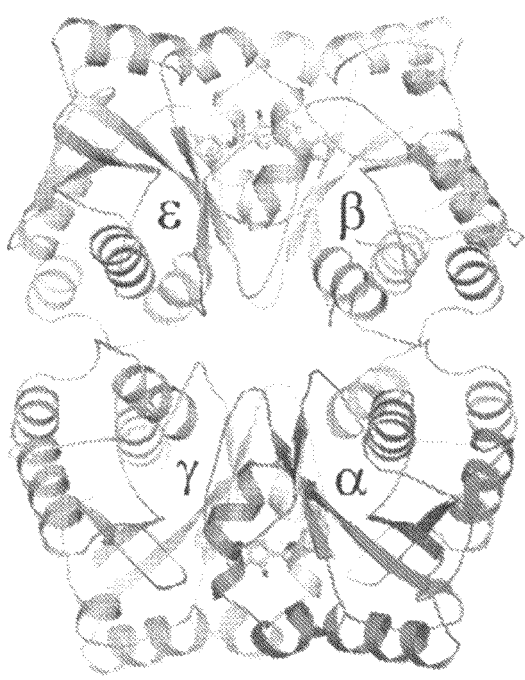

Figure 8
A 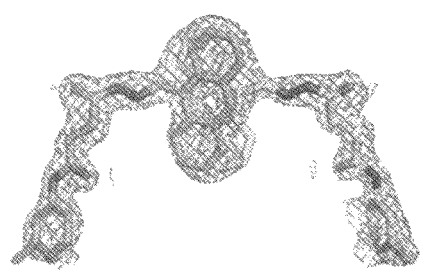
B 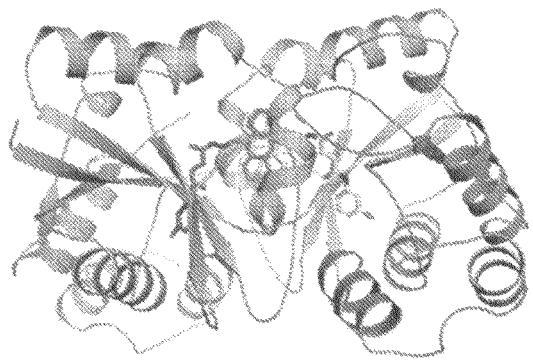

Figure 11
A
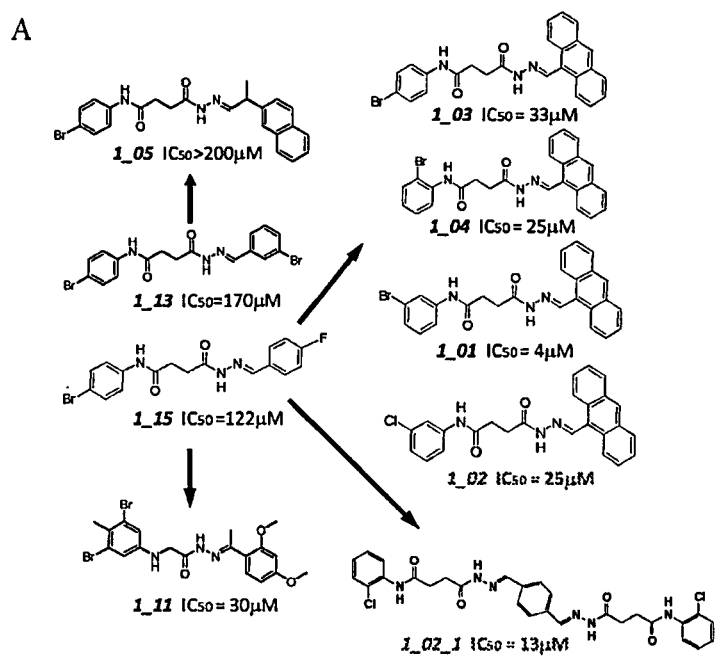
B
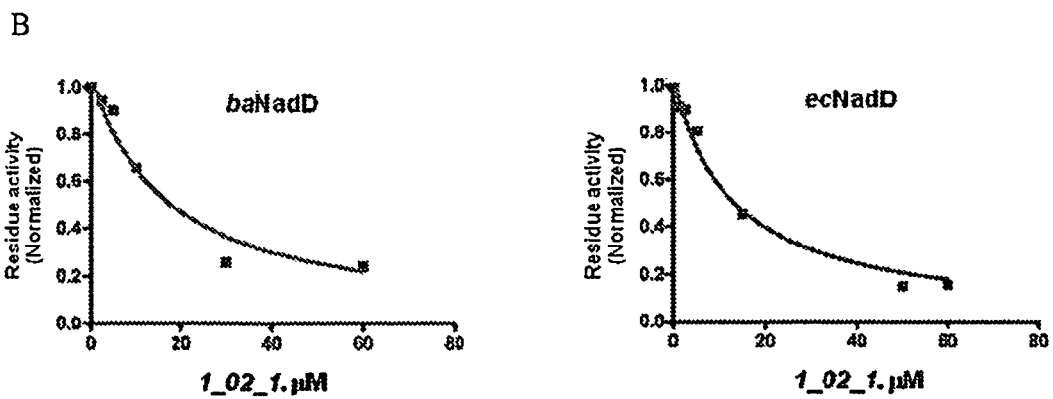

Figure 12
A
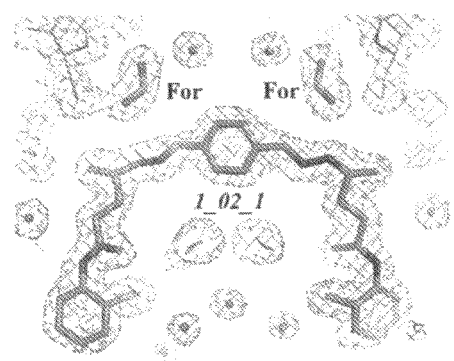
B
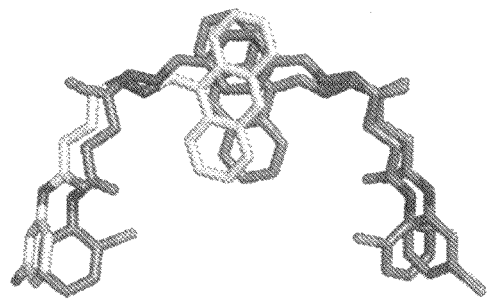
C
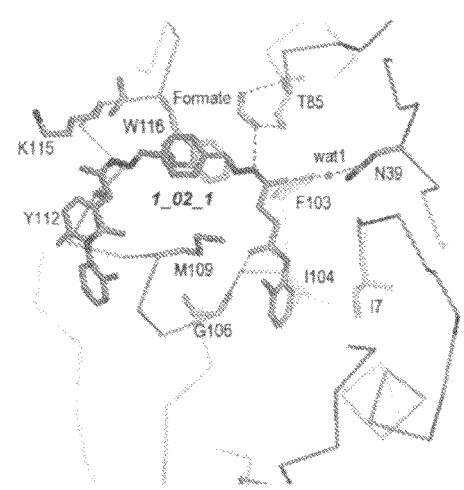

Scheme 1 a) benzene-1,4-dicarbaldehyde, ethanol, reflux

Scheme 2 a) water. b) succinic anhydride, DMF, 70°C. c) HBTU, DIPEA, DMF. d) TFA/CH$_2$Cl$_2$. e) Ethanol, 1N NaOH.

Scheme 3 a) napthalene-1-carbaldehyde, ethanol, reflux. b) benzene-1,4-dicarbaldehyde, ethanol, reflux

TARGETING NAD BIOSYNTHESIS IN BACTERIAL PATHOGENS

STATEMENT REGARDING FEDERALLY SPONSORED RESEARCH OR DEVELOPMENT

This invention was made with the support of the U.S. government under Grant Number AI059146 from the National Institute of Health (NIH). The U.S. government has certain rights in this invention.

CROSS REFERENCE TO RELATED APPLICATIONS

This application is a 371 of PCT/US10/41708 Jul. 12, 2010, which claims the benefit of U.S. Provisional Application No. 61/224,504 filed Jul. 10, 2009, which is hereby incorporated by reference.

TECHNICAL FIELD

The invention relates to microbiology. The invention further relates to methods of treating a microbial infection. In further aspects the invention relates to treating a bacterial infection.

BACKGROUND OF INVENTION

The versatility and resourcefulness of microbes in developing resistance to various therapies are widely recognized. Although chemical modifications of existing drugs and the development of novel inhibitors against a handful of previously established targets has proven to be successful in the short term, it is also apparent that new drug targets need to be explored to maintain and extend efficacious antibacterial therapy in the long run [1]. The need for new targets is further exacerbated by the emergence of bacterial pathogens with natural resistance to existing antibiotics and by a potential threat of pathogens with engineered antibiotic resistance.

NAD(P) biosynthesis as a promising, albeit relatively unexplored target pathway for the development of novel antimicrobial agents [2-4]. Cofactors of the NAD pool are indispensable as they are involved in hundreds of redox reactions in the cell. Additionally, NAD is utilized as a cosubstrate by a number of non-redox enzymes (e.g., by bacterial DNA ligases and protein deacetylases of the CobB/Sir2 family). This dictates the need to maintain NAD homeostasis via its active resynthesis and recycling of NAD degradation products. Recently, a number of insightful reviews have emphasized the potential of NAD(P) biosynthetic enzymes as drug targets for the treatment of cancer, autoimmune diseases, and neurodegenerative disorders [5-8]. Although the early steps in NAD biogenesis and recycling vary substantially between species, the enzymes driving the downstream conversion of nicotinic acid mononucleotide (NaMN) to NAD and NADP are present in nearly all analyzed bacterial genomes[2, 9]. Therefore, all three enzymes of this pathway—NaMN adenylyltransferase (EC 2.7.7.18), NAD synthetase (EC 6.3.1.5) and NAD kinase (EC 2.7.1.23) (encoded by the conserved genes nadD, nadE and nadF, respectively), represent promising broad-spectrum antibacterial targets. The observed essentiality of the respective genes is due to bacteria being unable to uptake phosphorylated pyridine nucleotides [2, 3]. Recent progress in the development of inhibitors targeting the last two enzymes, NadE [10-12] and NadF [13, 14], provides additional validation of NAD biosynthesis as a target pathway.

NadD converts NaMN, the first intermediate shared by the most common de novo and salvage/recycling routes, to nicotinic acid adenine dinucleotide (NaAD). Therefore, this enzyme should be indispensable in all bacterial species that utilize one or both of these routes for NAD biosynthesis. This is consistent with gene essentiality data for a number of bacterial species (as reviewed in [3, 16]). For example, the nadD gene was shown to be essential for survival in *Staphylococcus aureus* and *Streptococcus pneumoniae* that are fully dependent on niacin salvage (via PncA-PncB route). It is also essential in *Escherichia coli* and *Mycobacterium tuberculosis*, organisms that harbor both the de novo (NadB-NadA-NadC) and the salvage pathways. Remarkably, it has been recently demonstrated that NAD downstream pathway holds as an attractive target in both actively growing and nonreplicating pathogens [17]. NadD is present in nearly all important pathogens with only a few exceptional cases, such as *Haemophilus influenzae* which lacks most of NAD biosynthetic machinery and is dependent on salvage of the so-called V-factors [18].

Many representatives of the NadD family from pathogenic and model bacteria have been characterized mechanistically and structurally [19-24]. All of these enzymes have a strong substrate preference for NaMN over its amidated analog, NMN. On the other hand, all three isoforms of the functionally equivalent human enzyme (hsNMNAT-1, hsNMNAT-2 and hsNMNAT-3) have an almost equal catalytic efficiency for either substrate, NaMN or NMN [25, 26]. The observed difference in substrate specificity reflects the dual physiological role of the human enzyme (hereafter referred to as hsNMNAT) in the adenylation of both intermediates contributing to NAD biogenesis [7, 27]. Notably, among the three bacterial enzymes of the target pathway, NadD has the lowest sequence similarity to its human counterparts [3]. Comparative analysis of 3D structures of bacterial NadD and hsNMNAT revealed significant differences between their active site conformations [15], which are likely responsible for their distinct substrate specificities, thus opening an opportunity for selective targeting.

It is apparent that there is a need in the art for novel antimicrobial agents. To this end, the inventors have selected the NadD enzyme as a target for the development of specific inhibitors based on a number of criteria such as essentiality, broad conservation and structure-function distinction from its human counterpart.

BRIEF SUMMARY OF INVENTION

The emergence of multidrug-resistant pathogens necessitates the search for new antibiotics acting on previously unexplored targets. Nicotinate mononucleotide adenylyltransferase of the NadD family, an essential enzyme of NAD biosynthesis in most bacteria, was selected as a target for structure-based inhibitor development. Using iterative in silico and in vitro screens, the inventors identified small molecule compounds that efficiently inhibited target enzymes from *Escherichia coli* (ecNadD) and *Bacillus anthracis* (baNadD), but which had no effect on functionally equivalent human enzymes. Importantly, the results of this study for the first time validated NadD as a drug target for the development of broad-spectrum antibacterial compound.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 6. Structure of baNadD in complex with inhibitor 3_02 and comparison with product-bound baNadD structure. (A) Interactions between inhibitor and baNadD. Cα traces of baNadD are shown. Protein residues that interact with 3_02 are shown as sticks. Water molecules are shown as small spheres. (B) Superimposition of baNAD complex structure with the inhibitor (3_02) bound structure.

FIG. 7. baNadD-3_02 complex tetramer and 3_02 binding. (A) Crystal structure of *Bacillus anthracis* NadD-3_02 complex. Two baNadD dimers are shown. Only one orientation of the inhibitor 3_02 (in sticks) is shown in each binding site. (B) Overall structure of baNadD dimer (cyan and blue subunits) is shown with bound NaAD product. The orientation of this dimer is similar to monomer α and β in (A).

FIG. 8. Inhibitor 1_02 binds between two monomers of baNadD. (A). The Fo-Fc omit map for 1_02. Two 1_02 molecules, colored green and yellow, respectively, each with half occupancy are modeled in the density. (B). 1_02 binds at a baNadD monomer-monomer interface formed in the crystal of the complex. The two baNadD monomers are colored cyan and green respectively.

FIG. 11. (A). Structure and activities of representative Class 1 compounds. The compounds cocrystallized with baNadD are indicated with labels. (B). Dose dependent inhibition by compound 1_02_1 against baNadD (left panel) and ecNadD (right panel).

FIG. 12. Structure of baNadD-1_02_1 complex. (A). The 2Fo-Fc map of 1_02_1, the two formate molecules (For) and the surrounding regions. (B). Superposition of the enzyme bound 1_02_1 (blue) with 1_02 in its two orientations (represented in two different shades of gray). C). Detailed interactions between 1_02_1 and baNadD residues.

(B) Superposition of baNadD-3 02 complex (magenta) with apo human NMNAT-i (blue). Selected residues in baNadD that are involved in inhibitor binding (M109, Y112 and W116) are displayed as thin lines. Corresponding residues in hsNMNAT-i (L159, S162 and W169) are also shown.

The structure comparison illustrates that the conformations of bacterial NadD enzymes are very similar around the inhibitor binding region while the human enzyme is more divergent. hsNMNAT-1 residues corresponding to baNadID W116 and Y112 (W169 and S162, shown in thin blue line in B would clash with the inhibitor in its present pose.

Figure 20:
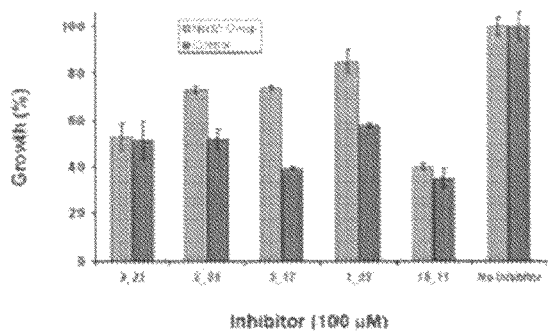

FIG. 20. Antibacterial assay: on-target versus off-target activity

Antibacterial activity of selected compounds at 100 tM on $E.\ coli$ overexpressing NadD compared to a control $E.\ coli$ strain (see Methods for details). The error bars represent the standard deviation between triplicate samples.

Figure 21:
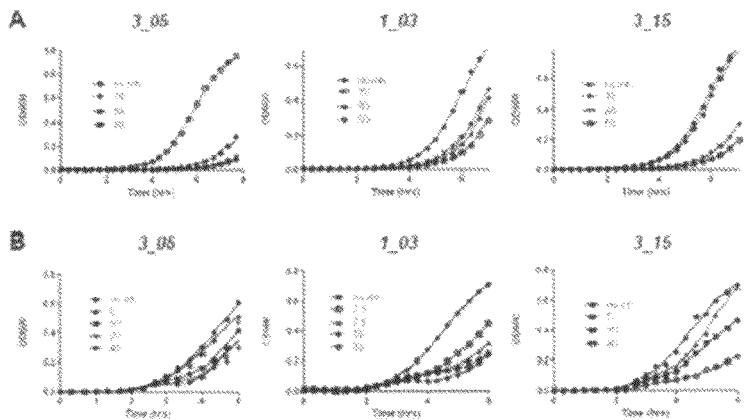

FIG. 21. Antibacterial assay: on-target versus off-target activity

Antibacterial activity of selected compounds at 100 μM on $E.\ coli$ overexpressing NadD (blue) compared to a control $E.\ coli$ strain (red) (see Methods for details). The error bars represent the standard deviation between triplicate samples.

Table 1. Inhibitory parameters of representative compounds from two chemotypes. The apparent values of inhibitory parameters (Ki and α) of two compounds (3_02 and 1_02) were determined for both enzymes by fitting the kinetic data to the general equation for the mixed-model inhibition ([43]). The data were collected by varying the concentration of an inhibitor and one of the two substrates (NaMN or ATP) at fixed concentration of another substrate (0.5 mM ATP or NaMN).

Table 2. Inhibition of target enzymes and antibacterial activity of selected compounds.

[a]Inhibitory efficiency of selected compounds (representative of classes 1, 3, and 15) for two target enzymes, ecNadD and baNadD is illustrated by $IC_{50}$ values. [b]Antibacterial activity of the same compounds against Gram-negative ($E.\ coli$) and Gram-positive ($B.\ subtilis,\ B.\ anthracis$) model species is reflected by $MIC_{50}$ values (the lowest concentration of compound causing more than 50% growth inhibition). [c]Only single-point high estimates of $MIC_{50}$ values were determined (70% growth inhibition at 100 microM for $E.\ coli$, and 96% inhibition at 50 microM for $B.\ subtilis$) for a representative of the class 15 that displayed mostly off-target antibacterial activity in $E.\ coli$ model; NA, not assayed. [d]$MIC_{50}$ of cmpd 1_03 for $B.\ anthracis$ was determined using a different set of concentrations (120, 60, 30, 15, 7.5, and 3.5 microM)

Table 3. Proteins targeted and the identification of residues adjacent to the sphere sets used to direct docking in each protein.

Table 4. Docking energies using selected compounds. Values represent the most favorable energy for each compound over the crystal structures used for docking for each species. Energies in kcal/mol. Most favorable energy for each compound is highlighted in light gray and the least favorable in dark gray.

Table 5. Electrostatic and van der Waals inhibitor-protein interaction energies using selected compounds. Values are based on the most favorable electrostatic or vdW energy for each compound over the crystal structures used for docking for each species. Energies in kcal/mol. Most favorable energy for each compound is highlighted in light gray and the least favorable in dark gray.

Table 6. Attractive van der Waals inhibitor-protein interaction energies using selected compounds. Values are based on the most favorable attractive vdW energy for each compound over the crystal structures used for docking for each species. Energies in kcal/mol. Most favorable energy for each compound is highlighted in light gray and the least favorable in dark gray.

Table 7. Crystal Data and refinement statistics. [a]$R_{sym}=\Sigma_{hkl}\Sigma_j|I_j-<I>|/\Sigma_{hkl}\Sigma_j|I_j|$. [b]$R_{work}=\Sigma_{hkl}|F_o-F_c|/\Sigma hkl|F_o|$, where $F_o$ and $F_c$ are the observed and calculated structure factors, respectively. [c]Five percent randomly selected reflections were excluded from refinement and used in the calculation of $R_{free}$.

Table 8. Inhibition data for compound primary testing. Compounds were originally selected from an ~million compound library.

Table 9. Inhibition data for selected compounds class 1_, 3_ and 15_. Inhibition % was measured at compound concentration of 100 μM for $E.\ coli$ NadD and 50 μM for $B.\ anthracis$ NadD. 1050 values, when applicable, are indicated.

Table 10. Selected structures for compounds of class 1_.

Table 11 Selected structures for compounds of class 3_.

Table 12. Additional structures for compounds of class 1_.

Table 13. Chemical structures of two classes of bacterial NadD inhibitors as represented by compounds 1_02 and 3_02[a]

Table 14. Crystal Data and refinement statistics

DETAILED DESCRIPTION OF THE INVENTION

I. Definitions

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a bacterial infection), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need thereof of treatment include, those in which a pathological condition of the invention is to be prevented, in which case treating refers to administering to a subject a therapeutically effective amount of a composition to a subject at risk of developing a pathological conditional of the invention.

II. The Present Invention

In earlier studies the inventors have used a comparative-genomics approach to identify NAD cofactor biosynthesis as a target pathway for development of new anti-infective therapies [2, 3]. The NadD enzyme was chosen as one of the most attractive targets within this pathway due to its nearly universal conservation in bacterial pathogens and its essentiality directly confirmed in a number of model bacteria [3]. A comparative enzymatic and structural analysis revealed substantial differences between bacterial enzymes and their human counterparts, opening an opportunity for development of selective NadD inhibitors. The fact that no drugs are known to act on NadD further contributes to this choice of a target in the context of the growing challenge of multidrug-resistant bacterial pathogens.

In the instant invention, an integrated structure-based approach was employed to identify small-molecule compounds that selectively inhibit enzymes of the NadD family with a potential broad spectrum of antibacterial activity. Combining computational screening of a virtual compound library with experimental testing of inhibitory and antibacterial activity of selected compounds and their analogs, the inventors have identified and characterized at least two classes (including 3_ class of compounds, 1_ class of compounds; see Table 2) of inhibitors with distinct chemical scaffolds (chemotypes) possessing a number of desired properties.

The approach of in silico screening was based on selective targeting of those active site residues that are highly conserved among bacterial NadD enzymes, yet quite distinct from the human counterpart enzymes [15, 19]. A focused targeting of a nicotinosyl-binding (as opposed to adenosyl-binding) site was also aimed to exploit the functional differences between the NaMN-preferring bacterial NadD and human enzymes with dual specificity for NaMN and NMN substrates [25, 26]. The inventors also took advantage of the large conformational differences between the apo and substrate-bound enzymes by specifically targeting the enzyme active site in the apo form so that the inhibitors would stabilize the enzyme in a catalytically impaired conformation.

Figure 2:
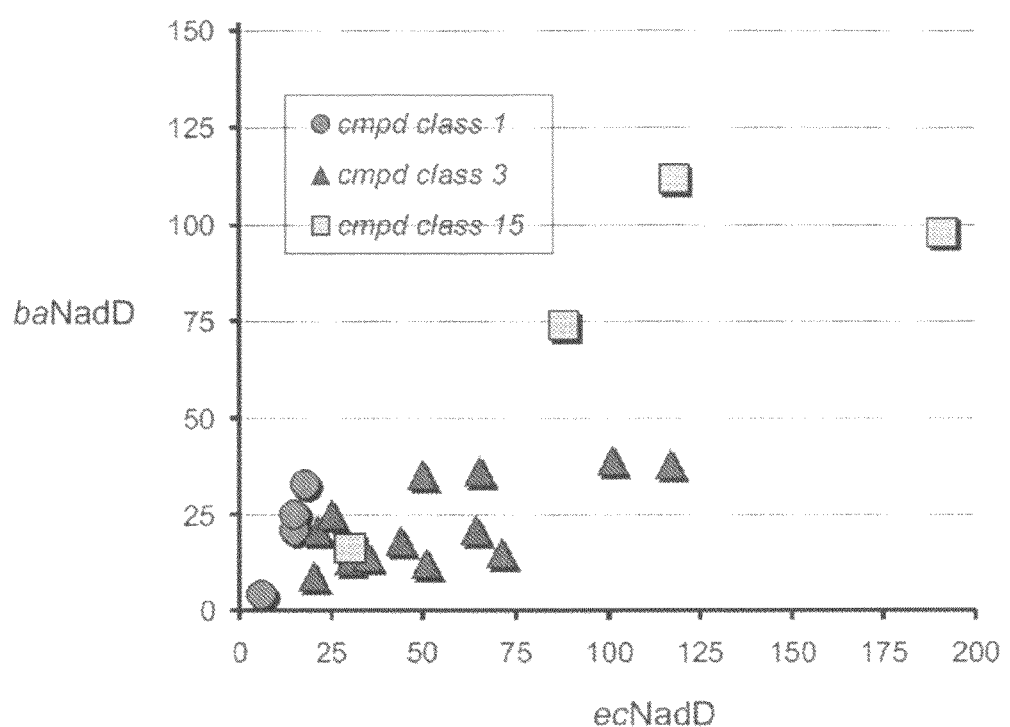
FIG. 2. Correlation analysis of IC50 values for classes 1, 3 and 15 compounds. The analysis, restricted to compounds with IC50 values <0.2 mM, was computed on the assumption that both 1050 values for *E. coli* and *B. anthracis* NadDs follow a Gaussian distribution (Pearson correlation).

The results of the invention support the efficiency and effectiveness of this strategy. First, it observed that an appreciable correlation between inhibitory properties of compounds against two divergent members of the NadD family, from Gram-negative (ecNadD) and Gram-positive bacteria (baNadD), even at the level of the primary experimental testing of ~300 compounds. This trend was even more apparent in the comparison of inhibitory properties of analogs of the three class of compounds (1_, 3_, and 15_) selected for detailed characterization (FIG. 2 and Table 8). These observations indicate that the level of structural conservation in the active sites of divergent representatives of the NadD family provides a potential for developing broad-spectrum inhibitors. At the same time, the three selected chemotypes showed no appreciable activity against human counterparts (hsNMNAT-1-3). This finding validated another premise of the invention, that the distinction between bacterial and human enzymes is sufficient for the development of selective (bacterial-specific) NadD inhibitors.

Figure 3:
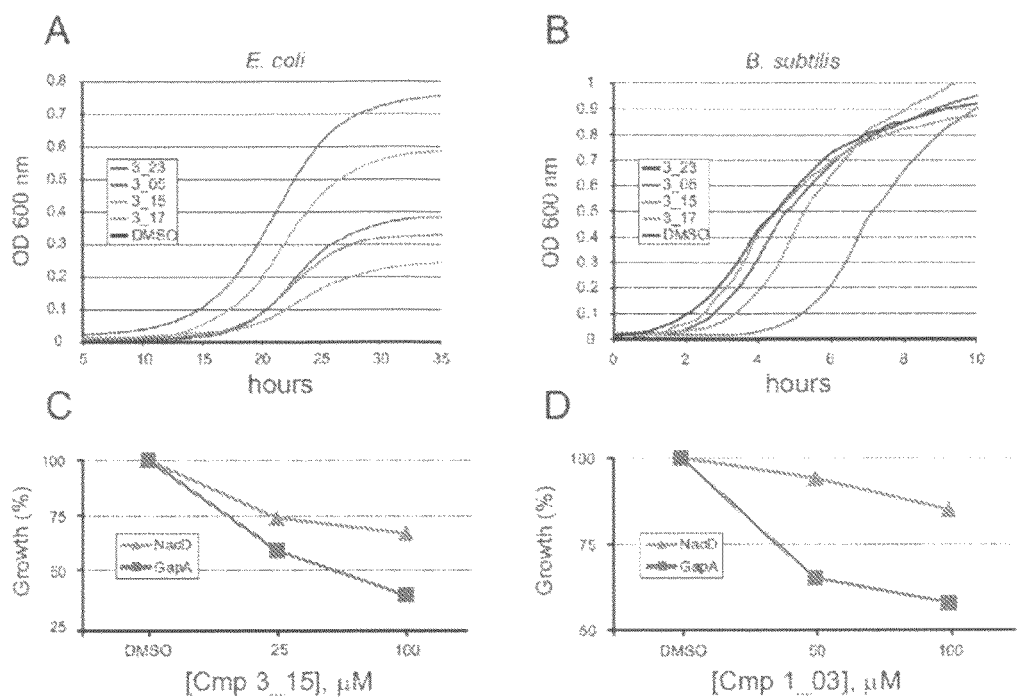
FIG. 3. Bacterial growth inhibition. (A) and (B) Effect of inhibitors of class 1 (100 μM) on cell growth as reflected in changes of the optical density at 600 nm of *E. coli* ΔnadA (A) and *B. subtilis* BSI 68 (B). (C) and (D) On-target inhibition effect. Overexpression of NadD in *E. coli* ΔnadA, nadD+ partially or totally suppresses action of the inhibitors 3_15 (C) and 1_03 (D), resulting in better cell survival.

The essentiality of the nadD gene previously established by genetic techniques, by itself, does not guarantee that inhibition of the NadD enzyme in the cell is possible and may indeed suppress bacterial growth. Moreover, the antibacterial activity of the analyzed compounds observed in Gram-negative (E. coli) and Gram-positive (B. subtilis) model systems, while being encouraging, could be due to some effects other than inhibition of the NadD enzyme. An E. coli model system to test whether the observed growth suppression was indeed due to the "on-target" action of representative NadD inhibitors was used. As illustrated in FIGS. 3C and 3D and FIG. 20, overexpression of the target nadD gene substantially increased resistance of this strain toward compounds of classes 1_ and 3_. These data directly validated the NadD enzyme as a drug target amenable to inhibition in a bacterial cell, which results in growth suppression.

Figure 5:
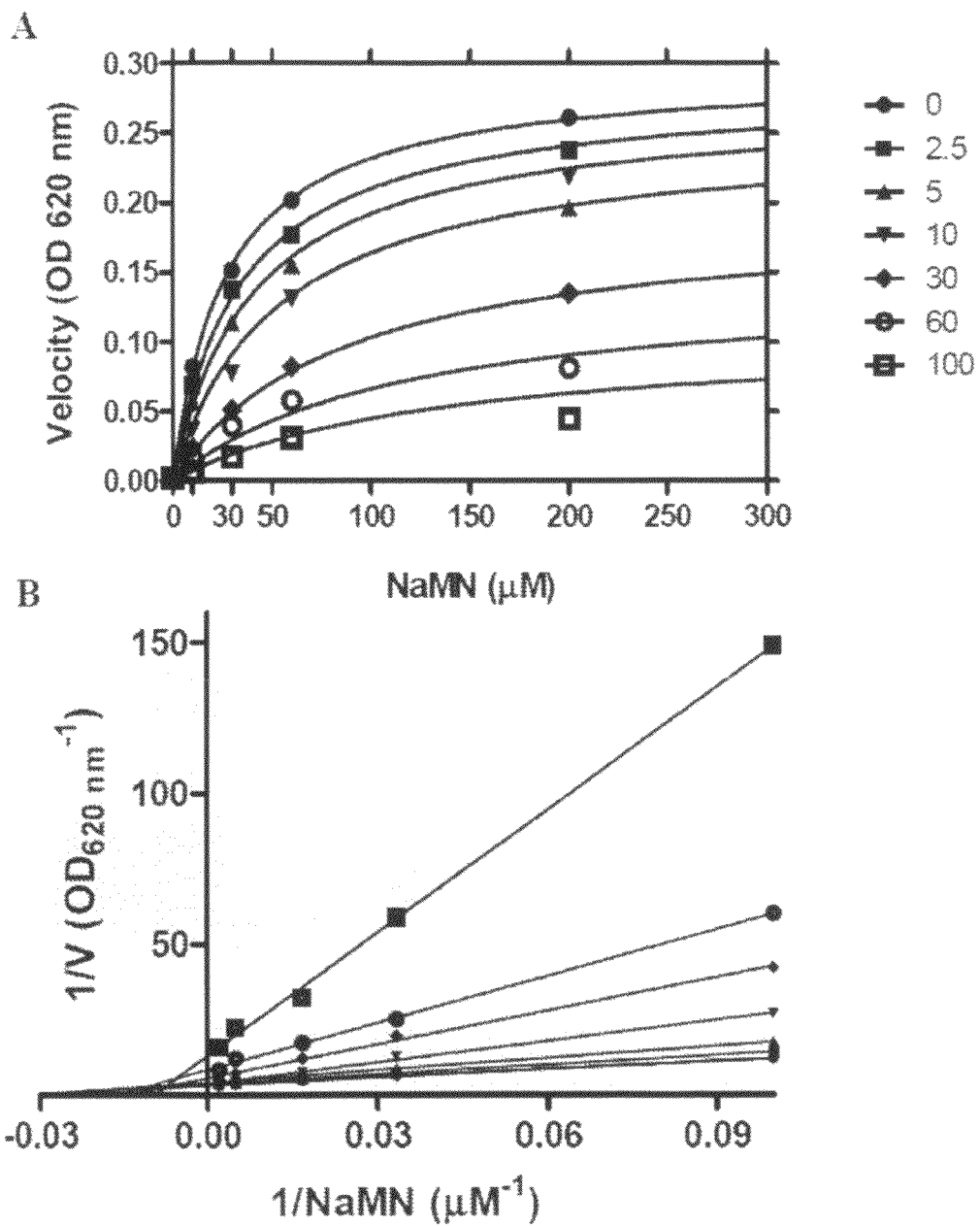
FIG. 5. NadD inhibition by two lead compounds 3_02 and 1_02. Hyperbolic plots of initial reaction rate (μmol/mg/min) as a function of NaMN substrate concentration (μM) measured at fixed concentration of the ATP substrate (500 μM) in the presence of varying concentrations of compounds 3_02 and 1_02 (0-200 μM range). The same data are also presented by a double-reciprocal (Lineweaver-Burk) plot illustrating mixed-type inhibition.

Finally, it was important to test the binding mode of NadD inhibitors. This seemed particularly important as the steady-state kinetic analysis of the representative compounds of both classes 1_ and 3_ revealed a mixed-type inhibition with a strong noncompetitive component (FIG. 5). To assess inhibitor binding mode(s) and to obtain a basis for rational improvement of the inhibitors, the inventors attempted co-crystallization of both bacterial NadD enzymes with a panel of compounds of classes 1_ and 3_. The structure of baNadD in complex with the compound 3_02 reported here confirmed that this inhibitor indeed binds in the active site area partially overlapping with the targeted NaMN substrate binding site (FIG. 6). Moreover the conformation of the baNadD active site in this complex is drastically different from its product-bound conformation. In fact, the inhibitor binding appears to stabilize the baNadD conformation in its apo form, incompatible with substrate binding and catalysis [21, 24]. Inhibitor interference at the level of substrate binding and the stabilization of alternative enzyme conformation may provide a rationale for the observed complex (mixed-type) kinetics of inhibition. Although the actual inhibitory mechanism is not fully clear, the obtained structural information is useful for further inhibitor optimization via structure-based design and synthesis of analogs. For example, engineering additional functional groups that may form specific hydrogen-bond interactions with the enzyme may enhance the binding affinity of the compound.

There is an unmet need in the medical arts related to treating bacterial infections for which the instant inventions fills a void. In particular, bacterial resistance was a consideration by the inventors. An example of bacterial resistance includes strains of Staphylococcus aureus resistant to methicillin and other antibiotics that are becoming more common place. Infection with methicillin-resistant S. aureus (MRSA) strains is also increasing in non-hospital settings. Vancomycin is an effective treatment for MRSA infections. A particularly troubling observation is that S. aureus strains with reduced susceptibility to vancomycin have emerged recently in Japan and the United States. The emergence of vancomycin-resistant strains would present a serious problem for physicians and patients. Another example of bacterial resistance is illustrated in the increasing reliance on vancomycin, which has led to the emergence of vancomycin-resistant enterococci (VRE), bacteria that infect wounds, the urinary tract and other sites. Until 1989, such resistance had not been reported in United States hospitals. By 1993, however, more than 10 percent of hospital-acquired enterococci infections reported to the Centers for Disease Control ("CDC") were resistant. Yet another example is apparent when considering *Streptococcus pneumoniae* causes thousands of cases of meningitis and pneumonia, as well as 7 million cases of ear infection in the United States each year. Currently, about 30 percent of *S. pneumoniae* isolates are resistant to penicillin, the primary drug used to treat this infection. Many penicillin-resistant strains are also resistant to other antimicrobial or antibacterial compounds. These examples, as well as many more, support the notion that there is a tremendous need in the medical arts for novel antibacterial compounds.

In certain aspects of the invention, a compound disclosed herein is useful for treating a bacterial infection. A bacterial infection is an infection that is, in-whole or in-part, caused by, for example, exposure to a bacterium from a bacterial genera and any species or derivative associated therewith, including for example, any one or more of the following bacterium genera: *Abiotrophia, Acaricomes, Acetitomaculum, Acetivibrio, Acetobacter, Acetobacterium, Acetobacteroides, Acetogenium, Acetohalobium, Acetomicrobium, Acetomonas, Acetonema, Achromobacter, Acidaminobacter, Acidaminococcus, Acidimicrobium, Acidiphilium, Acidithiobacillus, Acidobacterium, Acidocaldus, Acidocella, Acidomonas, Acidovorax, Acinetobacter, Acrocarpospora, Actinacidiphilus, Actinoacidiphilus, Actinoalloteichus, Actinobacillus, Actinobaculum, Actinobifida, Actinobispora, Actinocatenispora, Actinocorallia, Actinokineospora, Actinomadura, Actinomyces, Actinoplanes, Actinopolyspora, Actinopycnidium, Actinosporangium, Actinosynnema, Actinotelluria, Adhaeribacter, Aequorivita, Aerobacter, Aerococcus, Aeromicrobium, Aeromonas, Aestuariibacter, Afipia, Agarbacterium, Agitococcus, Agreia, Agrobacterium, Agrococcus, Agromonas, Agromyces, Ahrensia, Albidovulum, Alcaligenes, Alcanivorax, Algibacter, Algoriphagus, Alicycliphilus, Alicyclobacillus, Alishewanella, Alistipes, Alkalibacillus, Alkalibacter, Alkalibacterium, Alkalilimnicola, Alkalispirillum, Alkanindiges, Allisonella, Allobaculum, Allochromatium, Allofustis, Alteromonas, Alysiella, Aminobacter, Aminobacterium, Aminomonas, Ammonifex, Ammoniphilus, Amoebobacter, Amorphosphorangium, Amphibacillus, Ampullariella, Amycolata, Amycolatopsis, Anaeroarcus, Anaerobacter, Anaerobaculum, Anaerobiospirillum, Anaerobranca, Anaerocellum, Anaerococcus, Anaerofilum, Anaerofustis, Anaerolinea, Anaeromusa, Anaerophaga, Anaeroplasma, Anaerosinus, Anaerostipes, Anaerotruncus, Anaerovibrio, Anaerovorax, Ancalomicrobium, Ancylobacter, Aneurinibacillus, Angiococcus, Angulomicrobium, Anoxybacillus, Antarctobacter, Aquabacter, Aquabacterium, Aquamicrobium, Aquaspirillum, Aquicella, Aquifex, Aquiflexum, Aquimonas, Arachnia, Arcanobacterium, Archangium, Arcicella, Arcobacter, Arenibacter, Arhodomonas, Arizona, Arsenicicoccus, Arsenophonus, Arthrobacter, Asanoa, Asiosporangium, Asticcacaulis, Atopobium, Atopococcus, Atopostipes, Aurantimonas, Aureobacterium, Avibacterium, Axonoporis, Azoarcus, Azohydromonas, Azomonas, Azomonotrichon, Azorhizobium, Azorhizophilus, Azospira, Azospirillum, Azotobacter, Bacillus, Bacterionema, Bacteriovorax, Bacterium, Bacteroides, Balnearium, Balneatrix, Bartonella, Bdellovibrio, Beggiatoa, Beijerinckia, Belliella, Belnapia, Beneckea, Bergeriella, Betabacterium, Beutenbergia, Bifidobacterium, Bilophila, Blastobacter, Blastochloris, Blastococcus, Blastomonas, Blastopirellula, Bogoriella, Bordetella, Borrelia, Bosea, Brachybacterium, Brachymonas, Brachyspira, Brackiella, Bradyrhizobium, Branhamella, Brenneria, Brevibacillus, Brevibacterium, Brevigemma, Brevundimonas, Brochothrix, Brucella, Bryantella, Budvicia, Bulleidia, Burkholderia, Buttiauxella, Butyribacterium, Butyrivibrio, Byssovorax, Caenibacterium, Caldanaerobacter, Calderobacterium, Caldicellulosiruptor, Caldilinea, Caldithrix, Caldocellum, Caloramator, Caloranaerobacter, Caminibacillus, Caminibacter, Caminicella, Campylobacter, Capnocytophaga, Carbophilus, Carboxydibrachium, Carboxydocella, Carboxydothermus, Cardiobacterium, Carnobacterium, Caryophanon, Caseobacter, Castellaniella, Catellatospora, Catellibacterium, Catenibacterium, Catenococcus, Catenuloplanes, Catenulospora, Caulobacter, Cedecea, Cellulomonas, Cellulophaga, Cellulosimicrobium, Cellvibrio, Centipeda, Cerasibacillus, Chainia, Chelatobacter, Chelatococcus, Chitinihacter, Chitinophaga, Chlorobaculum, Chlorobium, Chloroflexus, Chondrococcus, Chondromyces, Chromatium, Chromobacterium, Chromohalobacter, Chlyseobacterium, Chryseomonas, Chrysiogenes, Citreicella, Citricoccus, Citrobacter, Clavibacter, Clavisporangium, Clostridium, Cobetia, Cohnella, Collimonas, Collinsella, Colwellia, Comamonas, Conchiformibius, Conexibacter, Coprothermobacter, Corallococcus, Coriobacterium, Corynebacterium, Couchioplanes, Crossiella, Cryobacterium, Cryptanaerobacter, Cryptobacterium, Cryptosporangium, Cupriavidus, Curtobacterium, Curvibacter, Cyclobacterium, Cystobacter, Cytophaga, Dactylosporangium, Dechloromonas, Dechlorosoma, Deferribacter, Defluvihacter, Dehalohacter, Dehalospirillum, Deinohacter, Deinococcus, Deleya, Delftia, Demetria, Dendrosporobacter, Denitrovibrio, Dermabacter, Dermacoccus, Dermatophilus, Derxia, Desemzia, Desulfacinum, Desulfarculus, Desulfatibacillum, Desulfitobacterium, Desulfoarculus, Desulfobacca, Desulfobacter, Desulfobacterium, Desulfobacula, Desulfobulbus, Desulfocapsa, Desulfocella, Desulfococcus, Desulfofaba, Desulfofrigus, Desulfofustis, Desulfohalobium, Desulfomicrobium, Desulfomonas, Desulfomonile, Desulfomusa, Desulfonatronovibrio, Desulfonatronum, Desulfonauticus, Desulfonema, Desulfonispora, Desulforegula, Desulforhabdus, Desulforhopalus, Desulfosarcina, Desulfospira, Desulfosporosinus, Desulfotalea, Desulfothermus, Desulfotignum, Desulfotomaculum, Desulfovihrio, Desulfovirga, Desulfurella, Desulfurobacterium, Desulfuromonas, Desulfuromusa, Dethiosulfovibrio, Devosia, Dialister, Diaphorobacter, Dichelobacter, Dichotomicrobium, Dickeya, Dictyoglomus, Dietzia, Diplococcus, Dokdoa, Dokdonella, Dokdonia, Dolosicoccus, Donghaeana, Dorea, Duganella, Dyadobacter, Dyella, Eberthella, Ectothiorhodospira, Edwardsiella, Eggerthella, Eikenella, Elizabethkingia, Elytrosporangium, Empedobacter, Enhygromyxa, Ensifer, Enterobacter, Enterococcus, Enterovibrio, Epilithonimonas, Eremococcus, Erwinia, Erysipelothrix, Erythrobacter, Erythromicrobium, Erythromonas, Escherichia, Eubacterium, Ewingella, Excellospora, Exiguobacterium, Faecalibacterium, Faenia, Falcivibrio, Ferrimonas, Ferrobacillus, Fervidobacterium, Filibacter, Filifactor, Filobacillus, Filomicrobium, Finegoldia, Flammeovirga, Flavimonas, Flavobacterium, Flectobacillus, Flexihacter, Flexistipes, Flexithrix, Fluoribacter, Fluviicola, Formivibrio, Francisella, Frankia, Frateuria, Friedmanniella, Frigoribacterium, Fulvimarina, Fulvimonas, Fundibacter, Fusibacter, Fusobacterium, Gaetbulibacter, Gaetbulimicrobium, Gaffkya, Gallibacterium, Gallicola, Garciella, Gardnerella, Gariaella, Gelidibacter, Gelria, Gemella, Gemmata, Gemmatimonas, Gemmobacter, Geobacillus, Geobacter, Geoder-* matophilus, Geopsychrobacter, Georgenia, Geospirillum, Geothermobacter, Geothrix, Geovibrio, Giesbergeria, Gillisia, Glaciecola, Globicatella, Gluconacetobacter, Gluconoacetobacter, Gluconobacter, Glycomyces, Goodfellowia, Gordona, Gordonia, Gracilibacillus, Granulicatella, Granulobacter, Grimontia, Guggenheimella, Gulosihacter, Haemophilus, Hafnia, Hahella, Halanaerobacter, Halanaerohium, Haliangium, Haliscomenobacter, Haloanaerobacter, Haloanaerobium, Halobacillus, Halobacteroides, Halocella, Halochromatium, Halococcus, Haloincola, Halolacti bacillus, Halomonas, Halonatronum, Halorhodospira, Halothermothrix, Halothiobacillus, Halovibrio, Helcococcus, Helicobacter, Heliobacillus, Heliobacterium, Heliophilum, Heliorestis, Herbaspinllum, Herbidospora, Herpetosiphon, Hespellia, Hippea, Hirschia, Hoeflea, Holdemania, Holophaga, Hongiella, Hordeomyces, Hyalangium, Hydrocarboniphaga, Hydrogenivirga, Hydrogenobacter, Hydrogenobaculum, Hydrogenomonas, Hydrogenophaga, Hydrogenophilus, Hydrogenothermophilus, Hydrogenothermus, Hydrogenovibrio, Hylemonella, Hymenobacter, Hyphomicrobium, Hyphomonas, Idiomarina, Ignavigranum, Ilyobacter, Inflabilis, Inquilinus, Intrasporangium, Iodobacier, Isobaculum, Isochromatium, Isoptericola, Jahnia, Janibacter, Jannaschia, Janthinobacterium, Jensenia, Jeotgalicoccus, Jiangella, Jonesia, Kangiella, Kerstersia, Kibdellosporangium, Kibdelosporangium, Kineococcus, Kineosphaera, Kineosporia, Kingella, Kitasatoa, Kilasalospora, Kitasatospora, Klebsiella, Kluyvera, Knoellia, Kocuria, Kofleria, Koserella, Kozakia, Kribbella, Kurthia, Kutzneria, Kytococcus, Labrys, Laceyella, Lachnobacterium, Lachnospira, Lactobacillus, Lactobacterium, Lactococcus, Lactosphaera, Lamprocystis, Lampropedia, Laribacter, Lautropia, Leadbetterella, Lebetimonas, Lechevalieria, Leclercia, Leeuwenhoekiella, Legionella, Leifsonia, Leisingera, Leminorella, Lentibacillus, Lentzea, Leptospirillum, Leptothrix, Leptotrichia, Leucobacter, Leuconostoc, Leucothrix, Levilinea, Levinea, Limnobacter, List, Listeria, Listonella, Loktanella, Lonepinella, Longispora, Lophomonas, Lucibacterium, Luteibacter, Luteimonas, Luteococcus, Lysobacter, Macrococcus, Macromonas, Magnetospirillum, Mahella, Malikia, Malonomonas, Mannheimia, Maribacter, Maricaulis, Marichromatium, Marinibacillus, Marinilabilia, Marinilactibacillus, Marinithermus, Marinitoga, Marinobacter, Marinobacterium, Marinococcus, Marinomonas, Marinospirillum, Marinovum, Marmoricola, Massilia, Megamonas, Megasphaera, Meiothermus, Melittangium, Mesonia, Mesophilobacter, Mesorhizobium, Methanomonas, Methylobacillus, Methylobacterium, Methylocapsa, Methylocella, Methylomicrohium, Methylomonas, Methylophaga, Methylophilus, Methylopila, Methylosarcina, Methylotenena, Methylovorus, Microbacterium, Microbispora, Microhulhifer, Micrococcus, Microcyclus, Microechinospora, Microellobosporia, Microlunatus, Micromonas, Micromonospora, Micropo/yspora, Micropruina, Microscilla, Microsphaera, Microstreptospora, Microtetraspora, Microvirgula, Millisia, Mima, Mitsuokella, Mobiluncus, Modestobacter, Moellerella, Mogibacterium, Moorella, Moraxella, Moraxella, (Branhamella), Moraxella, (Moraxella), Morganella, Moritella, Muricauda, Muricoccus, Myceligenerans, Mycetocola, Mycobacterium, Mycoplana, Myroides, Myxococcus, Nakamurella, Nannocystis, Natroniella, Natronincola, Nautilia, Naxibacter, Neisseria, Nereida, Nesterenkonia, Nevskia, Nicoletella, Nitratifractor, Nitratireductor, Nitratiruptor, Nitrobacter, Nocardia, Nocardioides, Nocardiopsis, Nonomuraea, Novosphingobium, Obesumbacterium, Oceanibulbus, Oceanicaulis, Oceanicola, Oceanimonas, Oceanithermus, Oceanohacillus, Oceanohacier, Oceanomonas, Oceanospirillum, Ochrobactrum, Octadecabacter, Odontomyces, Oenococcus, Oerskovia, Oleiphilus, Oleispira, Oligella, Oligotropha, Olsenella, Opitutus, Orenia, Oribacterium, Ornithinicoccus, Ornithinimicrobium, Ornithobacterium, Ottowia, Oxalicibacterium, Oxalobacter, Oxalophagus, Oxobacter, Paenibacillus, Paludibacter, Pandoraea, Pannonibacter, Pantoea, Papillibacter, Paracoccus, Paracolobactrum, Paralactobacillus, Paraliobacillus, Parascardovia, Parasporobaaerium, Parvibaculum, Parvopolyspora, Pasteurella, Pasteuria, Patulibacter, Paucihacter, Paucimonas, Pectinatus, Pectobacterium, Pediococcus, Pedohacter, Pelczaria, Pelobacter, Pelodictyon, Pelomonas, Pelospora, Pelotomaculum, Peptococcus, Peptoniphilus, Peptostreptococcus, Peredibacter, Persephonella, Persicivirga, Persicobacter, Petrimonas, Petrobacter, Petrotoga, Phaeobacter, Phaeospirillum, Phascolarctobaaerium, Phenylobacterium, Phocoenobacter, Photobacterium, Photorhabdus, Phyllobacterium, Phytomonas, Pigmentiphaga, Pilimelia, Pimelobacter, Pirella, Pirellula, Planctomyces, Planifulum, Planobispora, Planococcus, Planomicrobium, Planomonospora, Planopolyspora, Planotetraspora, Plantibacter, Pleomorphomonas, Plesiocystis, Plesiomonas, Podangium, Polaribacter, Polaromonas, Polyangium, Polymorphosphora, Pontibacillus, Porphyrobacter, Porphyromonas, Pragia, Prauserella, Prevotella, Proactinomyces, Promicromonospora, Promyxobacterium, Propionibacter, Propionibacterium, Propionicimonas, Propioniferax, Propionigenium, Propionimicrobium, Propionispira, Propionispora, Propionivibrio, Prosthecobacter, Prosthecochloris, Prosthecomicrobium, Protaminobacter, Proteiniphilum, Proteus, Protomonas, Providencia, Pseudaminobacter, Pseudoalteromonas, Pseudoamycolata, Pseudobutyrivibrio, Pseudoclavibacter, Pseudomonas, Pseudonocardia, Pseudoramibacter, Pseudorhodobacter, Pseudospirillum, Pseudoxanthomonas, Psychrobacter, Psychroflexus, Psychromonas, Psychroserpens, Pusillimonas, Pyxicoccus, Quadrisphaera, Rahnella, Ralstonia, Ramibacterium, Ramlibacter, Raoultella, Rarobacter, Rathayibacter, Reinekea, Renibacterium, Renobacter, Rhabdochromatium, Rheinheimera, Rhizobacter, Rhizobium, Rhizomonas, Rhodobacter, Rhodobium, Rhodoblastus, Rhodocista, Rhodococcus, Rhodocyclus, Rhodoferax, Rhodomicrohium, Rhodopila, Rhodoplanes, Rhodopseudomonas, Rhodospirillum, Rhodothalassium, Rhodothermus, Rhodovibrio, Rhodovulum, Riemerella, Rikenella, Robiginitalea, Roseateles, Roseburia, Roseiflexus, Roseinatronobacter, Roseobacter, Roseococcus, Roseospira, Roseospirillum, Roseovarius, Rothia, Rubritepida, Rubrivivax, Rubrobacter, Ruegeria, Ruminobacter, Ruminococcus, Saccharibacter, Saccharococcus, Saccharomonospora, Saccharophagus, Saccharopolyspora, Saccharothrix, Sagittula, Salana, Salegentibacter, Salibacillus, Salinibacter, Salinibacterium, Salinicoccus, Salinimonas, Salinispora, Salinivihrio, Salinospora, Salipiger, Salmonella, Samsonia, Sanguihacter, Saprospira, Sarcina, Sarraceniospora, Scardovia, Schineria, Schlegelella, Schwartzia, Sebekia, Sedimentibacter, Segniliparus, Seinonella, Sejongia, Selenomonas, Seliberia, Serinicoccus, Serpulina, Serratia, Shewanella, Shigella, Shinella, Shuttleworthia, Silanimonas, Silicibacter, Simonsiella, Simplicispira, Simsoniella, Sinorhizobium, Skermania, Slackia, Smaragdicoccus, Smithella, Sodalis, Soehngenia, Sorangium, Sphaerobacter, Sphaerophorus, Sphaerosporangium, Sphaerotilus, Sphingobacterium, Sphingobium, Sphingomonas, Sphingopyxis, Spirilliplanes, Spirillospora, Spirillum, Spirochaeta, Spirosoma, Sporacetigenium, Sporanaerobacter, Sporichthya, Sporobacter, Sporobacterium, Sporocytophaga, Sporohalobacter, Spornlactobacillus, Sporomusa, Sporosarcina, Sporotomaculum, Stackehrandtia, Staleya, Stanierella, Staphylococcus, Stap-

*pia, Starkeya, Stella, Stenotrophomonas, Sterolibacterium, Stigmatella, Stomatococcus, Streptacidiphilus, Streptimonospora, Streptoallomorpha, Streptoalloteichus, Streptobacillus, Streptobacterium, Streptococcus, Streptomonospora, Streptomyces, Streptomycoides, Streptosporangium, Streptoverticillium, Subdoligranulum, Subtercola, Succiniclasticum, Succinimonas, Succinispira, Succinivibrio, Sulfitobacter, Sulfobacillus, Sulfitricurvum, Sulfurihydrogenibium, Sulfurimonas, Sulfurospirillum, Sutterella, Suttonella, Syntrophobacter, Syntrophobotulus, Syntrophococcus, Syntrophomonas, Syntrophosphora, Syntrophothermus, Syntrophus, Tatlockia, Tatumella, Taxeohacter, Taylorella, Teichococcus, Telluria, Tenacibaculum, Tepidibacier, Tepidimicrobium, Tepidimonas, Tepidiphilus, Terasakiella, Terrabacter, Terracoccus, Terrimonas, Tessaracoccus, Tetragenococcus, Tetrasphaera, Tetrathiobacter, Thalassobacillus, Thalassobacter, Thalassobius, Thalassolituus, Thalassomonas, Thauera, Thaxtera, Thermacetogenium, Thermaerobacter, Thermanaeromonas, Thermanaerovibrio, Thermicanus, Thermincola, Thermithiobacillus, Thermoactinomyces, Thermoanaerobacter, Thermoanaerobacterium, Thermoanaerobium, Thermoanaerolinea, Thermobacterium, Thermobacteroides, Thermobifida, Themobispora, Thermobrachium, Thermochromatium, Thermocrinis, Thermocrispum, Thermodesulfatator, Thermodesulfobacterium, Thermodesulfobium, Thermodesulforhabdus, Thermodesulfovibrio, Thermojlavimicrobium, Thermohydrogenium, Thermomicrobium, Thermomonas, Thermomonospora, Thermonema, Thermonospora, Thermopolyspora, Thermosediminibacter, Thermosiculum, Thermosinus, Thermosipho, Thermosyntropha, Thermoterrabacterium, Thermotoga, Thermovenabulum, Thermovibrio, Thermus, Thetysia, Thialkalimicrobium, Thialkalivibrio, Thioalkalimicrobium, Thioalkalivibrio, Thiobaca, Thiobacillus, Thiobacter, Thiocapsa, Thiococcus, Thiocystis, Thiodictyon, Thiohalocapsa, Thiolamprovum, Thiomicrospira, Thiomonas, Thiopedia, Thioreductor, Thiorhodoccocus, Thiorhodococcus, Thiorhodovibrio, Thiosphaera, Thiothrix, Tindallia, Tissierella, Toltimonas, Trabulsiella, Treponema, Trichococcus, Trichotomospora, Truepera, Tsukamurella, Turicella, Turicibacter, unclassified, Ureibacillus, Uruburuella, Vagococcus, Varihaculum, Variovorax, Veillonella, Verrucomicrohium, Verrucosispora, Vibrio, Victivallis, Virgibacillus, Virgisporangium, Vitreoscilla, Vogesella, Volcaniella, Volucribacter, Vulcanibacillus, Vulcanithermus, Waksmania, Wautersia, Weeksella, Weissella, Williamsia, Wolinella, Woodsholea, Xanthobacter, Xanthomonas, Xenophilus, Xenorhabdus, Xylanibacterium, Xylanimicrobium, Xylanimonas, Xylella, Xylophilus, Yania, Yersinia, Yokenella, Zavarzinia, Zimmermannella, Zobellia, Zoogloea, Zooshikella, Zymobacter, Zymobacterium, Zymomonas,* and *Zymophilus.*

In certain aspects of the invention, an antibacterial compound selectively binds to an enzyme of the NAD biogenesis pathway thereby inhibiting its function. All three enzymes of this pathway—NaMN adenylyltransferase (EC 2.7.7.18), NAD synthetase (EC 6.3.1.5) and NAD kinase (EC 2.7.1.23) (encoded by the conserved genes nadD, nadE and nadF, respectively), represent promising broad-spectrum antibacterial targets. In specific aspects of the invention, an antibacterial compound selectively binds to and inhibits a function of NadD. In other specific aspects, the compound selectively binds a bacterial NadD over its human counterpart (e.g., hsNMNAT). In further other specific aspects, the bacterial NadD is *Escherichia coli* NadD (ecNadD) or *Bacillus anthracis* NadD (baNadD). In yet further other specific aspects, the bacterial NadD is *Escherichia coli* NadD (ecNadD). In yet even further other specific aspects, the bacterial NadD is *Bacillus anthracis* NadD (baNadD).

In certain aspects of the invention, an antibacterial compound of the invention can be used to treat an infection associated with an infectious or toxic biological warfare agent, including for example, anthrax (*Bacillus anthracis*), botulism (including, for example, *Clostridium botulinum* toxin types A through G), *Brucella* species (brucellosis), *Burkholderia mallei* (glanders), *Burkholderia pseudomallei* (melioidosis), *Chlamydia psittaci* (psittacosis), Cholera (*Vibrio cholerae*), *Clostridium perfringens* (Epsilon toxin), *Coxiella burnetii* (Q fever), *Cryptosporidium parvum, E. coli* O157:H7 (*Escherichia coli*), epsilon toxin of *Clostridium perfringens*, a food safety threat (including, for example, *Salmonella* species, *Escherichia coli* O157:H7, and *Shigella*), *Francisella tularensis* (tularemia), Lassa fever, Ricin toxin from *Ricinus communis* (castor beans), *Rickettsia prowazekii* (typhus fever), *Salmonella* species (salmonellosis), *Salmonella Typhi* (typhoid fever), *Shigella* (shigellosis), Staphylococcal enterotoxin B, Toxic syndrome, a water safety threat (including, for example, *Vibrio cholerae, Cryptosporidium parvum*), and *Yersinia pestis* (plague)).

In certain aspects of the invention, an antibacterial compound that selectively binds to an enzyme of the NAD biogenesis pathway is a compound described in class 1_ compounds, 3_ compounds, and 15_ compounds (for example, compounds described in Tables 1, 2 and 8-12). In specific aspects, a compound described in class 1_ compounds, 3_ compounds, and 15_ compounds inhibit a function of NadD. In other specific aspects, a compound described in class 1_ compounds, 3_ compounds, and 15_ compounds selectively bind bacterial NadD over its human counterpart (e.g., hsNMNAT). In further other specific aspects, the bacterial NadD is *Escherichia coli* NadD (ecNadD) or *Bacillus anthracis* NadD (baNadD). In yet further other specific aspects, the bacterial NadD is *Escherichia coli* NadD (ecNadD). In yet even further other specific aspects, the bacterial NadD is *Bacillus anthracis* NadD (baNadD). In specific aspects, class 1_ compounds, 3_ compounds, and 15_ compounds inhibit bacterial growth (for example, by bacterostatic means or bacteriocidal means).

In certain aspects of the invention, an antibacterial compound that selectively binds to an enzyme of the NAD biogenesis pathway thereby inhibiting its function is administered in combination with one or more other antibacterial compound. The one or more other antibacterial compound can be, for example, an antibacterial compound from a class of antibacterial compounds, including for example, a 2,4-diaminopyrimidine, an aminoglycoside, an amphenicol, an ansamycin, a beta-lactam, a carbapenem, a cephalosporin, a fluoroquinolone, a glycylcycline, a lincosamide, a macrolide, a monobactam, a nitrofuran, an oxazolidinone, a penicillin, a polypeptide, a quinolone or quinoline analog, a sulfonamide, a sulfone, a tetracycline, or other miscellaneous class of antibacterial compound. In specific aspects, the one or more other antibacterial compound can be, for example, amdinocillin (mecillinam), amikacin, amoxicillin, amoxicillin+clavulanate, ampicillin, ampicillin+sulbactam, atovaquone, azithromycin, aztreonam, bacampicillin, bacitracin, capreomycin, carbenicillin indanyl sodium, cefaclor, cefadroxil, cefamandole, cefazolin, cefdinir, cefditoren, cefepime, cefixime, cefinetazole, cefonicid, cefoperazone, cefotaxime, cefotetan, cefoxitin, cefpodoxime, proxetil, cefprozil, ceftazidime, ceftibuten, ceftizoxime, ceftriaxone, cefuroxime and cefuroxime axetil, cephalexin, cephalothin, cephapirin, cephradine, chloramphenicol, cinoxacin, ciprofloxacin, clarithromycin, clindamycin, cloxacillin, colistimethate, cycloserine, daptomycin, demeclocycline, dicloxacillin, dirithromycin, doripenem, doxycycline, enoxacin, ertapenem, erythromycin, fosfomycin, gatifloxacin, gemifloxacin, gentamicin, grepafloxacin, imipenem/cilastatin, imiquimod, kanamycin, levofloxacin, lincomycin, linezolid, lomefloxacin, loracarbef, mafenide, malathion, meropenem, methenamine hippurate, methicillin, metronidazole, mezlocillin, minocycline, moxifloxacin, mupirocin, nafcillin, nalidixic acid, neomycin, netilmicin, nitrofurantoin, nitrofurazone, norfloxacin, novobiocin, ofloxacin, oxacillin, oxytetracycline, penicillin, piperacillin, piperacillin+tazobactam, podofilox, polymyxin B, quinupristin+dalfopristin, retapamulin, rifapentine, rifaximin, saturated solution of potassium iodide, sparfloxacin, spectinomycin, streptomycin, sulfadiazine, sulfamethoxazole, sulfisoxazole, sulphur precipitated in petrolatum, trichloroacetic acid, bichloroacetic acid, teicoplanin, telithromycin, terbinafine, tetracycline, ticarcillin, ticarcillin+clavulanic acid, tigecycline, tobramycin, trimethoprim, trimethoprim+sulfamethoxazole, trovafloxacin, and vancomycin.

Routes of administration for administering an antibacterial compound of the invention or one or more other antibacterial compound includes, for example, intraarterial administration, epicutaneous administration, eye drops, intranasal administration, intragastric administration (e.g., gastric tube), intracardiac administration, subcutaneous administration, intraosseous infusion, intrathecal administration, transmucosal administration, epidural administration, insufflation, oral administration (e.g., buccal or sublingual administration), oral ingestion, anal administration, inhalation administration (e.g., via aerosol), intraperitoneal administration, intravenous administration, transdermal administration, intradermal administration, subdermal administration, intramuscular administration, intrauterine administration, vaginal administration, administration into a body cavity, surgical administration (e.g., at the location of a site of infection), administration into the lumen or parenchyma of an organ, or other topical, enteral, mucosal, parenteral administration, or other method or any combination of the forgoing as would be known to one of ordinary skill in the art (see, for example, Remington's Pharmaceutical Sciences, 18th Ed. Mack Printing Company, 1990, incorporated herein by reference). In certain aspect of the invention drawn to administering antibacterial compound of the invention and one or more other antibacterial compound, the order in which these compounds are administered may be any order (e.g., sequentially or concurrently) and by any route of administration.

alone in the same or in separate containers, depending on, for example, cross-reactivity or stability, and can also be supplied in solid, liquid, lyophilized, or other applicable form. The container means of the kits will generally include, for example, a vial, test tube, flask, bottle, syringe or other container means, into which a component may be placed, and preferably, suitably aliquoted. Where there is more than one component in the kit, the kit can contain a second, third or other additional container into which the additional component may be contained. However, various combinations of components may be comprised in one container. A kit of the invention will also typically include a means for containing the composition, additional agent, or any other reagent container in close confinement for commercial sale. Such containers may include, for example, injection or blow molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition. In this case, the container means may itself be a syringe, pipette, and/or other such like apparatus, from which the formulation may be applied to an infected area of the body, injected into an animal, and/or even applied to and/or mixed with the other components of the kit.

However, in other embodiments the components of the kit may be provided as dried powder(s). When reagents and/or components are provided as a dry powder, the powder can be reconstituted by the addition of a suitable solvent. It is envisioned that the solvent may also be provided in another container means. The container means will generally include a vial, test tube, flask, bottle, syringe and/or other container means, into which the composition is placed, preferably, suitably allocated. The kit may also comprise a second container means for containing a sterile, pharmaceutically acceptable buffer and/or other diluent.

A kit of the present invention will also typically include a means for containing the vials in close confinement for commercial sale, such as, e.g., injection and/or blow-molded plastic containers into which the desired vials are retained. Irrespective of the number and/or type of containers, the kits of the invention may also comprise, and/or be packaged with, an instrument for assisting with the injection/administration and/or placement of the composition within the body of an animal. Such an instrument may be a syringe, pipette, forceps, and/or any such medically approved delivery vehicle.

Examples of compounds are disclosed below.

A Compound of Structural Formula 1A:

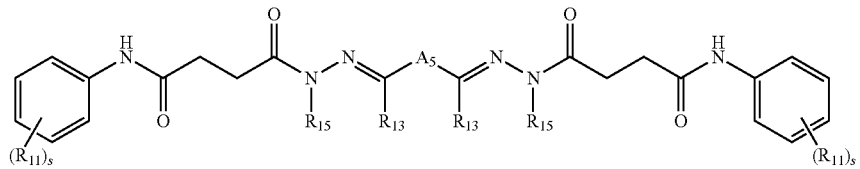

In certain aspects of the invention a kit is captured by the invention. In particular embodiments, the invention is drawn to a kit used for treating a bacterial infection. In specific aspects, the kit comprises one or more antibacterial compounds of the invention for treating a bacterial infection.

The kits may comprise a suitably aliquoted composition and/or additional agent composition as may be necessary. The components of the kit may be packaged in combination or wherein $A_5$ is selected from the group consisting of cycloalkene, arylene, heteroarylene and polycyclic fused ring, preferably benzene, naphthalene and anthracene, each $R_{11}$ is independently selected from the group consisting of halogen, hydroxy and alkyl, preferably Cl, Br, I and methyl; ortho position-Cl;

each $R_{13}$ is independently selected from the group consisting of hydrogen and alkyl, preferably hydrogen and methyl;

each $R_{15}$ is independently selected from the group consisting of a carboxy group and an alkyl group substituted with a carboxy group, preferably —$CH_2$—COOH; and s is an integer from 0 to 5, preferably 1.

A compound of structural formula 1B:

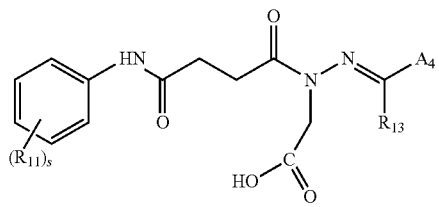

wherein $A_4$ is selected from the group consisting of aryl, heteroaryl and aralkyl, preferably

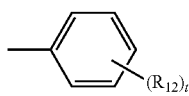

where each $R_{12}$ is independently selected from the group consisting of halogen, alkyl, hydroxy, and —O—$R_{14}$ where $R_{14}$ is selected from the group consisting of halogen, aryl and alkyl, preferably methyl and t is an integer from 0 to 5,

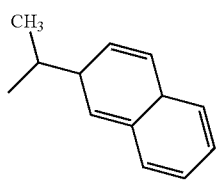

each $R_{11}$ is independently selected from the group consisting of halogen, hydroxy and alkyl, preferably Cl, Br, I and methyl; ortho position-Cl;

each $R_{13}$ are independently selected from the group consisting of hydrogen and alkyl, preferably hydrogen and methyl; and s is an integer from 0 to 5, preferably 1.

A pharmaceutical composition comprising the compound of any one of the compounds of formula 1A, 1_02_01, 1_02_02 and 1B as an active ingredient and a pharmaceutically acceptable carrier or excipient.

Group 01 Compounds

A pharmaceutical composition comprising at least one compound of Formula 1 as an active ingredient and a pharmaceutically acceptable carrier or excipient:

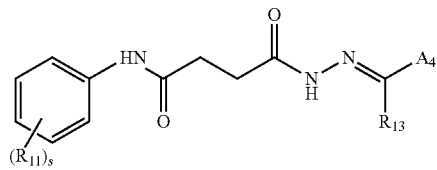

Formula 1 wherein $A_4$ is selected from the group consisting of aryl, heteroaryl and aralkyl;

preferably

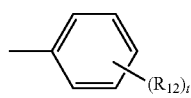

where each $R_{12}$ is independently selected from the group consisting of halogen, alkyl, hydroxy, and —O—$R_{14}$, where $R_{14}$ is selected from the group consisting of halogen and alkyl, preferably methyl, and t is an integer from 0 to 5;

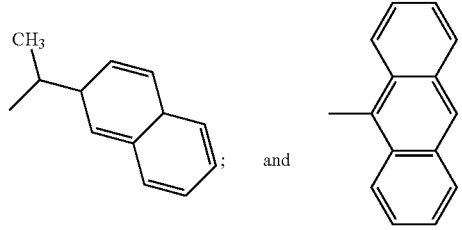

each $R_{11}$ is independently selected from the group consisting of halogen and alkyl, preferably Cl, Br, I and methyl; ortho position-Cl;

each $R_{13}$ are independently selected from the group consisting of hydrogen and alkyl, preferably hydrogen and methyl; and s is an integer from 0 to 5, preferably 1.

In one embodiment, $A_4$ is selected from the group consisting of

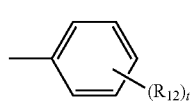

where each $R_{12}$ is independently selected from the group consisting of halogen, alkyl, hydroxy, and —O—$R_{14}$, where $R_{14}$ is selected from the group consisting of halogen and alkyl, preferably methyl, and t is an integer from 0 to 5;

where each $R_{11}$ is independently selected from the group consisting of Cl, Br, I and methyl;
$R_{13}$ is selected from the group consisting of hydrogen and methyl;
and
s is an integer from 0 to 3.

Group 15 Compounds

A pharmaceutical composition comprising at least one compound of Formula 15 as an active ingredient and a pharmaceutically acceptable carrier or excipient:

Formula 15 wherein Ar is selected from the group consisting of arylene, aralkylene, heteroarylene and aralkyheteroarylene.

In one embodiment, where Ar is where $L_1$ is selected from the group consisting of alkylene and a direct bond, preferably methylene, ethylene, direct bond, branched,
each $R_1$ and $R_2$ are independently selected from the group consisting of
halogen,
alkyl,
—N(R)$_2$ where each R is independently selected from the group consisting of hydrogen and alkyl, preferably both methyl),
—O—$R_6$ where $R_6$ is hydrogen or alkyl, preferable methyl,
—COOR$_3$ where $R_3$ is hydrogen or alkyl, preferable methyl,
—S—$R_4$ where is alkyl, preferable methyl,
—CO—$R_5$ where $R_5$ is alkyl, preferable methyl.

In another embodiment, Ar is

Group 03 Compounds

A pharmaceutical composition comprising at least one compound of Formula 3 as an active ingredient and a pharmaceutically acceptable carrier or excipient:

Formula 3 where $A_4$ is selected from the group consisting of hydrogen, alkyl and aryl,
$A_5$ is selected from the group consisting of —CONH$_2$ and $(R_8)_p$ where each $R_8$ is independently selected from the group consisting of halogen and alkyl, preferably halogen, and p is an integer from 0 to 5, preferably 1 or 2,
$A_3$ is selected from the group consisting of $(R_7)_w$ where each $R_7$ is independently selected from the group consisting of halogen and alkyl, preferably para-F, and w is an integer from 0 to 5, and In one embodiment, $A_3$ is selected from the group consisting of -continued

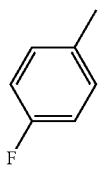

and A₅ is

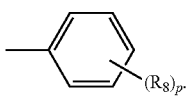

Compounds of structural formula 1A can be produced by, for example, reacting with heating to reflux a compound of Formula 1M with a benzene-1,4-dicarbaldehyde in the presence of a solvent:

Formula 1M

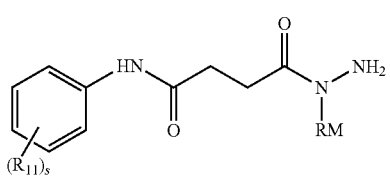

where RM is selected from the group consisting of hydrogen and

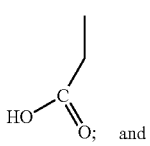

each $R_{11}$ is independently selected from the group consisting of halogen, hydroxy and alkyl and s is an integer from 0 to 5.

The solvent may be ethanol.

The compound of formula 1M may be:

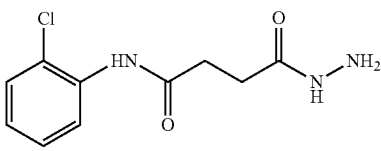 [SMILES: NNC(=O)CCC(=O)Nc1ccccc1Cl]

and the method may produce the compound of structural formula 1_02_1.

The compound of formula 1M may be:

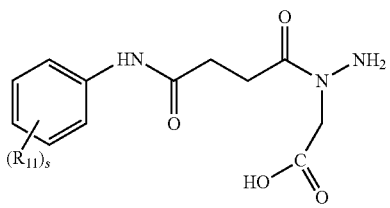

and the method may produce the compound of structural formula 1_02_2.

The compound structural formula 2M may be produced by, for example, reacting with heating to reflux a compound of Formula 3M with a naphthalene-1-carbaldehyde in the presence of a solvent:

Formula 2M

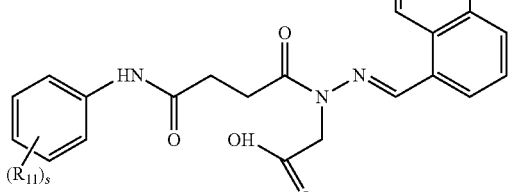

Formula 3M

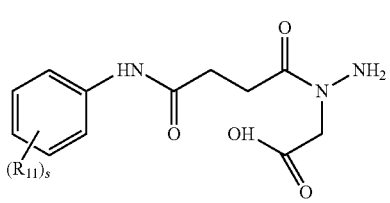

where in formulae 2M and 3M, each $R_{11}$ is independently selected from the group consisting of halogen, hydroxy and alkyl and s is an integer from 0 to 5.

The solvent may be ethanol.

The compound of formula 3M may be compound 8 and the compound produced may be formula 1_02_03:

Compound 8

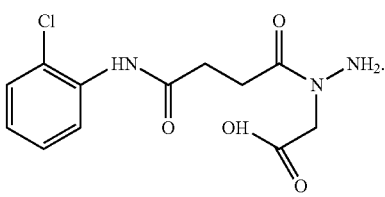

Further, the compound of formula 3M may be produced by:
Reacting ethyl bromoacetate 3 with tert-butylcarbazate 2 to form (N'-tert-Butoxycarbonyl-hydrazino)-acetic acid ethyl ester 4;
Reacting (N'-tert-Butoxycarbonyl-hydrazino)-acetic acid ethyl ester 4 with succinic anhydride to form 4-(N'-tert-Butoxycarbonyl-N-ethoxycarbonylmethyl-hydrazino)-4-oxo-butyric acid 5;
Mixing 4-(N'-tert-Butoxycarbonyl-N-ethoxycarbonylmethyl-hydrazino)-4-oxo-butyric acid 5 with O-Benzotriazole- N,N,N',N'-tetramethyl-uronium-hexafluoro-phosphate (HBTU) and N,N-Diisopropylethylamine (DIPEA) in N,N-dimethylformamide (DMF) and adding an aniline group, where said aniline group may be unsubstituted or substituted with at least one group X selected from halogen, hydroxy and alkyl, to form {N'-tert-Butoxycarbonyl-N-[3-(X-phenylcarbamoyl)-propionyl]-hydrazino}-acetic acid ethyl ester 6';

Dissolving {N'-tert-Butoxycarbonyl-N-[3-(X-phenylcarbamoyl)-propionyl]-hydrazino}-acetic acid ethyl ester 6' in Trifluoroacetic acid (TFA) in dichloromethane to form {N-[3-(X-phenylcarbamoyl)-propionyl]-hydrazino}-acetic acid ethyl ester 7'; and Dissolving {N-[3-(X-phenylcarbamoyl)-propionyl]-hydrazino}-acetic acid ethyl ester 7' in ethanol followed by addition of 1N NaOH to form {N-[3-(X-phenylcarbamoyl)-propionyl]-hydrazino}-acetic acid 8'.

Preferably, the aniline group is a 2-chloroaniline;
compound 6' is butoxycarbonyl-N-[3-(2-chloro-phenylcarbamoyl)-propionyl]-hydrazino}-acetic acid ethyl ester 6;
compound 7' is {N-[3-(2-Chloro-phenylcarbamoyl)-propionyl]-hydrazino}-acetic acid ethyl ester 7; and
compound 8' is {N'-tert-Butoxycarbonyl-N-[3-(X-phenylcarbamoyl)-propionyl]-hydrazino}-acetic acid ethyl ester 6 in ethanol followed by addition of 1N NaOH to form
{N-[3-(X-phenylcarbamoyl)-propionyl]-hydrazino}-acetic acid 8.

III. Examples

Figure 1:
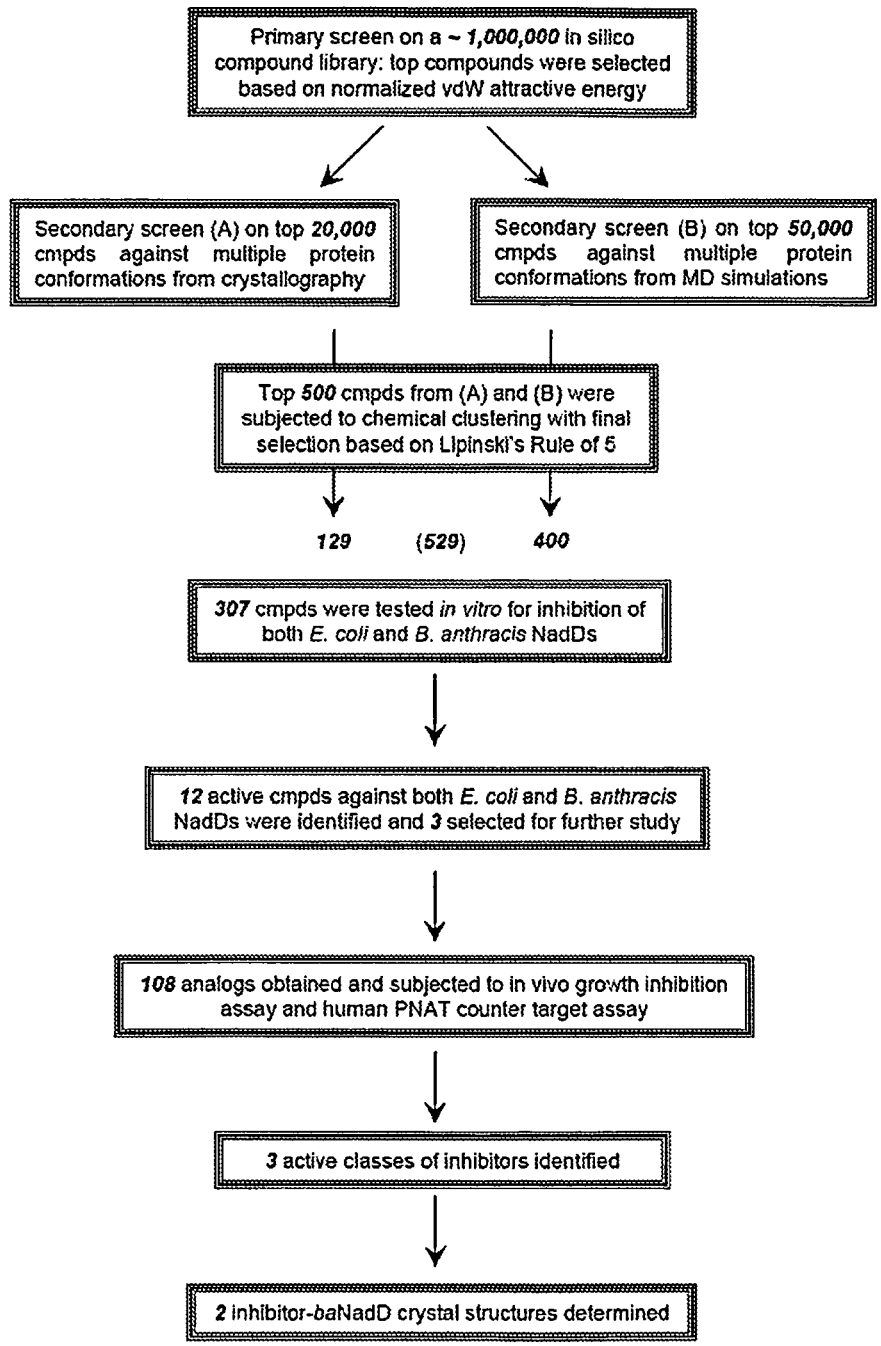
FIG. 1. Flowchart of the structure-based approach for developing bacterial NadD inhibitors.

An overview of the structure-based approach applied in this study for NadD inhibitor discovery is summarized in FIG. 1. In silico screening of the large virtual library of small-molecule compounds to identify potential NadD inhibitors was performed using the ecNadD structural template. Of the ~500 top-ranking in silico hits, 307 commercially available compounds were subjected to in vitro primary testing for inhibition of two representative target enzymes, ecNadD and baNadD. A series of analogs of three high-ranking compounds of distinct chemotypes (1__, 3_, and 15_) active against both target enzymes were characterized in more detail by both enzymatic and cell-based assays. A co-crystal structure of baNadD in complex with one of the inhibitors, 3__02, revealed atomic details of its interactions with the enzyme active site, providing guidelines for future structure-based inhibitor optimization.

Example 1

System Preparation for In Silico Database Screening

The substrate binding site of ecNadD [S1] was selected as the target for docking. Visual inspection of the binding region, solvent accessibility calculations along with consideration of sequence conservation led to the selection of residues Phe8, His19, Ile105 and Ile106 to define the putative inhibitor binding site. In addition, the level of sequence conservation between the bacterial and human enzymes in this region is low, thereby maximizing the potential that inhibitors specific for bacterial NadD are identified. The apo ecNadD structure (pdb 1k4k) was used for the primary screen as it represents a more open form of the binding pocket compared to the product deamido-NAD bound form. Molecular modeling and dynamics calculations were undertaken to prepare the protein structures for screening. All modeling calculations were performed with the program CHARMM [S2, S3] using the CHARMM22 all-atom protein force field and the TIP3P water model [S4]. In the case of the crystallographic structures in 1k4k the sidechain of Trp117 partially blocks the targeted binding side. Therefore, the conformation of sidechain was searched by performing a two-dimensional $\chi 1$, $\chi 2$ dihedral energy surface. Following reading of the structures of monomers A, C and D from 1k4k into CHARMM and adding hydrogens via the IC utility, the energy surfaces were performed by constraining the remainder of the protein structure and systematically sampling $\chi 1$ and $\chi 2$ in 15 degree increments with an energy minimization to an RMS gradient $<10^{-4}$ kcal/mol/Å at each step in the surface. From the resulting energy surfaces the lowest energy conformation of the residue was obtained and used for docking. For all three monomers the resulting conformation was such that the Trp117 sidechain did not block the binding site. The resulting conformation of monomer A of 1k4k was used for the primary screen of ~1 million compounds with those for monomers A, C and D used in secondary screen one. Additional conformations of the protein for use in secondary screen two was generated by MD simulation. System preparation for the simulation involved obtaining the A monomer of 1k4k, building hydrogens based on the IC facility in CHARMM followed by a 500 step Steepest Descent energy minimization with the protein non-hydrogen atoms harmonically restrained with a mass weighted force constant of 1. The system was then overlaid with a preequilibrated box of water designed to be a minimum of 8 Å larger than the protein in the X, Y and Z directions. Water molecules with the oxygen atom within 2.5 Å of any protein non-hydrogen atom were deleted. The system was then minimized for 500 SD steps with the protein harmonically restrained, as above, followed by an additional 500 step SD minimization of the entire system. The MD simulation was initiated from the minimized structure using the Leapfrog integrator in the isothermic, isobaric (NPT) ensemble [S5] with an integration timestep of 2 fs and SHAKE [S6] of all covalent bonds involving hydrogens. Nonbond interactions were truncated at 12 Å with smoothing of the Lennard Jones interactions performed via a switching function over 10 to 12 Å and the electrostatic interactions smoothed via a shifting function. The trajectory was continued for 10 ns with the initial 1 ns treated as equilibration, coordinate sets were saved every 100 ps. To identify unique conformations of the protein for docking, structures from the simulations were separated into structurally similar clusters using the program NMRCLUST [S7]. From this process representative conformations were obtained from the five largest clusters. These included time frames from 2.1, 5.4, 6.6, 8.5 and 9.1 ns.

Example 2

Chemical Similarity and Compounds' Clustering

Chemical similarity was determined using the MACCS Bit fingerprints in combination with the Tanimoto index to define the level of chemical similarity between two compounds [S8, S9]. This procedure allows for all the compounds to be sorted into clusters where the compounds in each cluster have similar chemical features [S10]. One or two compounds were then selected from each cluster, with the selection being based on physical properties related to Lipinksi's rule of 5 [S11, S12]. Application of these rules during compound selection maximizes the potential that the selected compounds will have appropriate bioavailability properties. However, in cases where clusters did not contain compounds that had all the desired physical properties, compounds were still selected for assay. Chemical clustering and estimation of physical properties was performed using the program MOE (Chemical Computing Group, Inc.).

Example 3

In Silico Screening of the Compound Library

The substrate binding site of ecNadD [19] was selected as the target for docking. System preparation involved analysis of the target protein structure, selection of inhibitor binding site, and generation of the sphere set used to direct the docking. The design of the template for in silico screening was based on the 3D structure of ecNadD reported in our earlier study [19]. The targeted binding pocket encompassed the nicotinosyl binding site (near residues Asn40, Thr85, Phe104 and Ile106 in ecNadD) as well as the catalytic site near the conserved (H/T)×GH motif (around Phe8, Gly10 and His19). All database screening calculations were carried out with DOCK 4.0 [37, 38]. The primary screening was performed on a 3D database of over 1 million low-molecular-weight commercially available compounds developed in the University of Maryland Computer-Aided Drug Design (CADD) Center [39, 40]. Ligand flexibility was incorporated during docking via the anchor-based search method [41]. Compounds from the initial primary screen were docked onto the protein based on the total ligand-protein interaction energy and scored based on the van der Waals (vdW) attractive energies normalized for molecular size [42].

Top scoring compounds from the primary screen were subjected to more rigorous secondary docking, where additional optimization of the ligand was performed during the build-up procedure. Additionally, conformational flexibility of ecNadD was taken into account via the inclusion of multiple protein conformations either from the crystallographic studies (secondary screen A) or from a molecular dynamics (MD) simulation of ecNadD (secondary screen B). In secondary screen A, the top 20,000 scoring compounds from the primary screening were individually docked to the three conformations of apo ecNadD obtained from the 1k4k crystal structure. In secondary screen B, multiple protein conformations were obtained from the MD simulation of apo ecNadD. The top 50,000 scoring compounds from the primary screen were then docked against five MD-generated conformations and ranked using the normalized total interaction energy for each compound. The top scoring compounds from the two separate secondary screens, totaling 500 and 1000, respectively, were then separately subjected to the final compound selection based on physical properties and chemical similarity. Determination of chemical similarity and further selection of compounds were performed according to standard procedures. Finally, a total of 529 unique compounds were selected; of these, 307 were purchased from the commercial vendors for the in vitro inhibition assay. After primary testing, three chemotypes (classes 1_, 3_, and 15_) were selected for further analysis of chemical analogs. A total of 89 analogs were purchased and experimentally tested.

Example 4

Testing of Selected Compounds

To evaluate compounds obtained from virtual screening the inventors experimentally tested their inhibitory activity against two representative NadD target enzymes, from the model gram-negative bacterium E. coli and from the Gram-positive pathogen B. anthracis. Both recombinant enzymes were overexpressed in E. coil and purified, and their steady-state kinetic parameters were obtained using a standard coupled assay [28]. An extensive kinetic analysis of baNadD enzyme, which included detection and exploration of negative cooperativity, was recently published [24]. The results of our previously reported kinetic analysis of this enzyme, albeit less detailed, yielded comparable steady state parameters that reflect strong preference for NaMN over NMN [9]. A similar preference was observed for ecNadD. The experimental testing of selected compounds for their ability to inhibit NaM-NATase activity of NadD enzymes was performed in the 96-well microtiter plate format using a colorimetric end-point assay, which includes an enzymatic conversion of the released PPi to Pi and a chromogenic reaction with the ammonium molybdate/Malachite Green reagent [29].

At this stage of analysis inhibitors with moderate affinity were identified (e.g., $IC_{50}$ at least 100 µM or better). Therefore, for each of the two enzymes the testing was performed in the presence of compounds at 50-100 µM. The results of primary testing of all 307 compounds against both enzymes are shown in Table 7. At the 20% inhibition threshold, this method identified 38 ecNadD inhibitors. Remarkably, the baNadD enzyme showed on average a twofold higher susceptibility to inhibition yielding 77 compounds at the same threshold. An appreciable correlation across the entire set of 307 analyzed compounds could be observed in their inhibitory properties against both enzymes (Table 7). This trend can be best illustrated by the comparison of two sets of ~10% top-ranking ecNadD and baNadD inhibitors revealing that nearly one-third of them are shared between both sets (the estimated probability to get at least 12 random matches is $3 \times 10^{-12}$). This observation indicated that the applied in silico screening strategy was indeed successful in targeting NadD active-site components conserved between quite divergent representatives of this enzyme family. Combining this strategy with the parallel experimental testing of compounds against two divergent target enzymes allowed us to identify 12 potentially broad-spectrum NadD inhibitors.

Example 5

Selection and Comparative Analysis of NadD Inhibitor Analogs

To validate and further explore the utility of the three selected chemotypes, structurally similar and commercially available analogs of compounds 1_, 3_, and 15_ were identified using chemical fingerprint-based similarity analysis [30, 31]. For each of the primary compounds, 15 to 40 analogs were purchased and analyzed by the same inhibitory assay. Inhibitory activity above a 20% threshold against at least one of the analyzed NadD enzymes was confirmed for 66 of the 89 analogs (Table 8). For example, of the 29 analogs of compound 3_, 23 were active against ecNadD and 24 against baNadD, whereas all 18 analogs of compound 1_ turned out to be inhibitors of both enzymes. Notably, among 42 analogs of compound 15_, 23 compounds were confirmed as baNadD inhibitors, but only 2 compounds had an appreciable inhibitory effect on ecNadD.

Overall, an observed frequent occurrence of analogs of compounds 1_ and 3_ that are active against both divergent members of NadD family supports the possibility of developing broad-spectrum NadD inhibitors. Although all the analyzed analogs were selected based only on structural similarity (without any attempts of their rational improvement), many of them displayed a moderate improvement of inhibitory properties compared to the original compounds. For example, 10 analogs of compounds 1_ and 3_ had improved activity against ecNadD and 22 against baNadD, pointing to the possibility of their further optimization. $IC_{50}$ values against ecNadD and baNadD determined for a subset of 33 compounds representing all three chemotypes ranged from low micromolar to >200 micromolar (Table 8). Comparative analysis of these data revealed an appreciable correlation (r=0.79) of the inhibitory properties of these compounds against both target enzymes over the entire subset (FIG. 2). The strongest correlation was observed for the compounds from the most active class 1_ (r=0.98). This observation further confirms the feasibility of developing broad-spectrum NadD inhibitors.

To assess potential selectivity of these inhibitors against bacterial targets, several of the most active representatives of each chemotype were tested for their ability to inhibit human countertarget enzymes (hsNMNAT-1-3). These assays were performed at 100 µM concentration of the compounds, i.e., in the conditions leading to >90% inhibition of bacterial NadD enzymes. Remarkably, none of the tested compounds displayed any appreciable inhibitory activity against the three human isozymes (<5% for hsNMNAT-1 and hsNMNAT-3, and <10% for hsNMNAT-2). These compounds displayed the same efficacy and specificity when tested at a higher concentration of BSA (1 mg/ml) in the assay, which is a common test to eliminate promiscuous inhibitors [32, 33]. Overall, the observed antibacterial selectivity and versatility of the analyzed inhibitors further support NadD as a promising target for the use and development of broad-spectrum antibiotics.

Example 6

Kinetic Analysis of NadD and Primary Testing of Selected Compounds

A discontinuous assay was utilized to determine the steady-state kinetics parameters $k_{cat}$ and $K_m$ for NadD and for inhibitory testing of selected compounds. This assay couples pyrophosphate ($PP_i$) byproduct formation of NaMNATase activity to colorimetric detection of free phosphate released upon enzymatic hydrolysis.

(1) NaMN Adenylyltransferase (NaMNATase) Reaction $NaMN + ATP + Mg^{2+} \rightarrow NaAD^+ + AMP + PP_i + Mg^{2+}$ (2) Inorganic pyrophosphatase (IPase) reaction $PP_i + H_2O \rightarrow 2P_i$ Excess IPase is used to ensure rapid conversion of pyrophosphate to orthophosphate so that the rate-limiting step in this system is the NaMN adenylyltransferase reaction. Excess inorganic phosphate also decreases the probability that observed inhibition is due to the inhibition of IPase and not the target enzyme. The inventors confirmed that the best NadD inhibitors (with $IC_{50}$ values ranging from 5 to 25 µM) did not inhibit IPase.

Steady-state kinetic analysis of ecNadD and baNadD target enzymes was performed by varying substrate (NaMN or ATP) concentrations were 0, 10, 30, 60, 200, 500 µM at fixed saturating concentration of second substrate (0.5 mM). Apparent values of $K_m$ and $k_{cat}$ were calculated by fitting initial rates to a standard Michaelis-Menten model using the software GRAPHPAD PRISM.

The standard inhibition assay was configured in a 96-well format for automated liquid-handling and convenient readout. Each compound was prepared as a 10 mM stock solution in dimethyl sulfoxide (DMSO) and diluted tenfold (10% DMSO) before usage.

Each reaction contained 2.3 nM ecNadD (or 1.2 nM baNadD) in 100 mM Hepes, pH 7.5 buffer, 0.2 mM ATP, 0.07 or 0.2 mM NaMN, 10 mM $MgCl_2$, 0.1 mg/ml bovine serum albumin, 0.2 U inorganic pyrophosphatase, and 50 or 100 µM tested compound (the complete lists of tested compounds with structure and vendor information is provided in Tables 1 and 2). Bovine serum albumin was included in the assay to reduce the effects of promiscuous inhibitors.

The choice of two-fold $K_{m(app)}$ concentrations of both NaMN and ATP substrates was necessary to ensure a good signal/noise ratio under the initial velocity phase of enzymatic reactions (10-20% substrate depletion), while retaining a linear signal response (0-15 µM PPi). The same assay setup was applied when testing small—molecule inhibitors against human countertargets. Concentrations of hsNMNAT-1 and hsNMNAT-2 were 3 nM, whereas hsNMNAT-3 was tested at 15 nM. After preincubation of the enzyme with the compounds for 5 min at room temperature, the reaction was initiated by addition of NaMN substrate. The reaction was allowed to progress for 20 min at room temperature prior to quenching by addition of 100 µL of Malachite Green Reagent in 1.2 M sulfuric acid prepared as described by Cogan et al. [29]. After 20-30 min incubation to allow for complex/color formation, the absorbance in each well was measured at 620 nm using a microplate reader (Beckman DTX-880). To account for contribution of free Pi and/or PPi (present in the sample or released due to nonspecific hydrolysis of ATP during incubation) as well as of background absorbance (color) of the tested compounds, parallel reactions were run for each experimental point without addition of NadD enzymes, and their $W_{on}$ values were subtracted from the measurements of enzyme activity in their respective samples. Reaction in the presence of 2% DMSO but without inhibitory compound served as a positive control. Each measurement was made in triplicate. Based on the sensitivity and reproducibility of the assay, inhibition ≥20% was considered reliable. A continuous coupled assay that detected reduction of $NAD^{+}$[28] was used for preliminary assessment of NaMNTase activity and to corroborate kinetic parameters obtained with Malachite Green discontinuous assay.

Example 7

$IC_{50}$ Measurements and $K_i$ Determination

The compounds selected based on the results of primary testing were further characterized using the malachite green end-point assay. The initial rate of enzymatic reaction was measured at fixed NaMN and ATP concentrations (equal to two-fold $K_m$ values) and various concentrations of an inhibitory compound. The $IC_{50}$ value was determined by plotting the relative NaMNATase activity versus inhibitor concentration and fitting to the equation (1) using GRAPHPAD PRISM.

$$V_i = \frac{V_0}{1 + \frac{[I]}{IC_{50}}} \quad (1)$$

$V_0$ and $V_i$ represent initial rates in the absence and presence of inhibitor concentration [I].

For $K_i$ determination, the enzyme was preincubated with various fixed concentrations of inhibitors for 5 min. The reaction was initiated by the addition of fixed concentration of NaMN (five-fold $K_m$) at varying concentrations of ATP (ranging from 0.2 to fivefold $K_m$) and vice versa. The inhibition constant and inhibition pattern were evaluated by fitting the data to the Michealis-Menten rate equation (2) for general (mixed-type) inhibition [43] with the program GRAPHPAD PRISM.

$$V = \frac{V_{max}[S]}{K_m\left(1 + \frac{[I]}{K_i}\right) + [S]\left(1 + \frac{[I]}{\alpha K_i}\right)} \quad (2)$$

$V_{max}$ and $K_m$ are standard Michaelis-Menten parameters, and $K_i$ is the equilibrium dissociation constant for the enzyme-inhibitor complex. The parameter a defines the degree to which the inhibitor binding affects the affinity of the enzyme for the substrate and is diagnostic of the inhibition mode, which may be purely competitive ($\alpha \gg 1$), purely noncompetitive ($\alpha=1$), uncompetitive ($\alpha \ll 1$), or mixed-type ($\alpha>1$ or $\alpha<1$).

Example 8

Suppression of Bacterial Growth in Culture

E. coli strains used for growth-suppression experiments and for target verification were prepared in the background of the E. coli K-12 BW25113 (ΔnadA) knockout strain with disrupted NAD de novo synthesis pathway from the Keio collection (a gift by Dr. H. Mori, Keio University, Japan) [44]. This strain was used in combination with one of the two expression plasmids from the E. coli ASKA library [45] enabling inducible overexpression of the: (i) E. coli nadD gene (to test for the increased resistance against NadD inhibitors) or the (ii) E. coli gapA gene, a housekeeping metabolic enzyme glyceraldehyde-3-phosphate dehydrogenase (as a negative control). Starter cultures were grown overnight in LB medium. Cells were harvested, washed, and resuspended in the M9 minimal growth medium containing 1% glycerol, 0.1 mM IPTG, 50 mg/l kanamicin, 35 mg/l chloramphenicol and a limiting amount of nicotinamide (Nam, 0.4 µM). Upon reaching an optical density at 600 nm of 0.05, cells were used to initiate growth experiments in 96-well plate at various concentrations of inhibitors.

The bacterial growth at 37° C. in these (and other) experiments was monitored by continuous absorbance measurement at 600 nm using an orbital shaker/microplate reader ELx808™. The area under the curve (AUGC) was used to calculate the growth inhibition [46] and was compared to the respective amount of DMSO. The AUGC was integrated and calculated with GRAPHPAD PRISM. Growth suppression studies of B. subtilis 168 (Bs168) were performed following a similar procedure in a chemically defined medium [47] containing glucose (4 g/l), tryptophan (50 mg/l), glutamine (2 g/l, $K_2HPO_4$ (10 g/l), $KH_2PO_4$ (6 g/l), sodium citrate (1 g/l), $MgSO_4$ (0.2 g/l), $K_2SO4$ (2 g/l), $FeCl_3$ (4 mg/l), $MnSO_4$ (0.2 mg/l). B. anthracis was grown in the same minimal medium containing additionally 10% LB medium for robust growth.

Selected compounds causing an appreciable growth inhibition were subject of minimal inhibitory concentration (MIC) determination in a series of dilutions from 160 µM down to 2.5 µM. The high concentration limit was determined by solubility problems observed for many compounds. In this concentration range only some of the analyzed compounds displayed >90% growth inhibition. Therefore, for consistency, the value of MIC was defined as the lowest concentration of compound that caused more than 50% growth inhibition (as determined by AUGC method).

The antibacterial activity of selected NadD inhibitors was assessed by their ability to suppress the growth of model Gram-negative (E. coli) and Gram-positive (B. subtilis) bacteria in liquid culture. To establish conditions potentially maximizing the effect of NadD inhibition in an E. coli model, ΔnadA mutant strain with disrupted de novo NAD synthesis were use. To further restrict the flux of NaMN (the committed substrate of the NadD target enzyme) growth studies on the experimentally established lowest concentration of Nam (0.4 µM) supporting the growth of this diagnostic strain on minimal media were performed. In these conditions, many of the selected NadD inhibitors of classes 1 and 3 showed an appreciable growth suppression effect at 100 µM (FIG. 3A and Table 8). To assess the extent of "on-target" (NadD-dependent) versus "off-target" (nonspecific) antibacterial effects of these compounds, an E. coli strain containing an overexpression plasmid vector with the E. coli nadD gene was used. The growth of this strain in the presence of selected inhibitors was compared to an isogenic control strain containing the same plasmid vector overexpressing a housekeeping gapA gene (unrelated to NAD synthesis). As shown in FIGS. 3C and 3D, overexpression of ecNadD suppressed the antibacterial activity of the tested representatives of NadD inhibitors of classes 1 and 3. On the other hand, the bactericidal effect of the compound 15_11 (Table 2) was essentially the same in both the NadD-overexpressing and control strain suggesting that this effect is largely non-specific (NadD-independent). An alternative interpretation that the on-target activity of 15_11 is too high to be suppressed by NadD overexpression appears unlikely, as the in vitro inhibitory properties of this compound are below average ($IC_{50,\ ecNadD}$~200 µM). Based on the structure of this compound, one may expect its hydrolysis in the medium to benzoate, a compound known to have a general and non-specific antibacterial activity.

Figure 4:
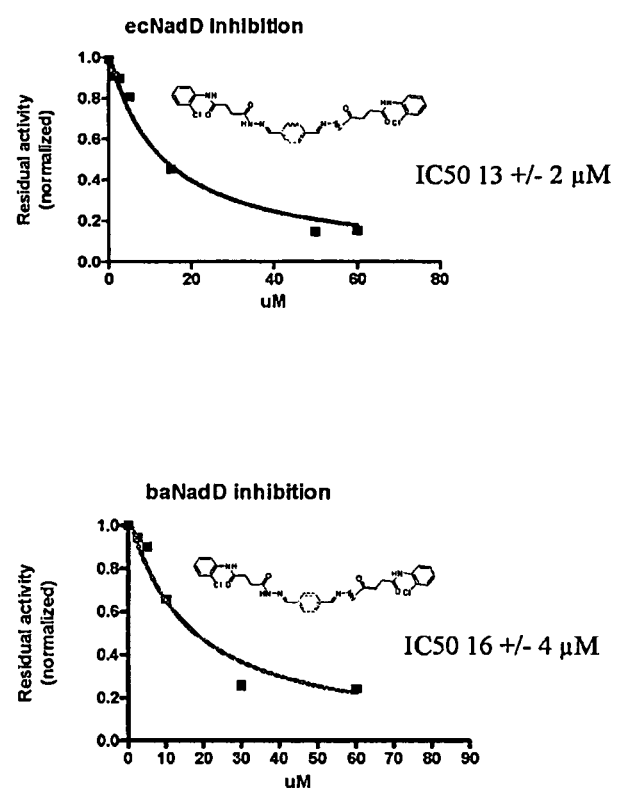
FIG. 4. 01_02_01 inhibition. (A) 01_02_01 inhibition of ecNadD. (B) 01_02_01 inhibition of baNAD.

An appreciable antibacterial activity was also observed for several analogs of compounds of class 1_ and 3_ against the model gram-positive bacteria B. subtilis (Table 2 and Table 8). Interestingly, the antibacterial effect of tested compounds in B. subtilis was manifested by delayed growth in contrast to E. coli where it was largely a decreased final cell density (FIG. 3B). Although establishing a rationale for this difference and confirming the actual target in Gram-positive bacteria remain to be accomplished, the growth-suppression data shown in Table 2 indicate that NadD inhibitors do indeed function as broad-spectrum antibiotics. MIC for active compounds 3_02, 3_05, 3_15, 3_23, and 1_03 against B. anthracis sterne, B. subtilis, and E. coli was determined. A general correlation was observed between NadD inhibition and antibacterial activity, although being less pronounced in E. coli (Table 2). Cell wall impermeability of gram-negative bacteria could be a major determinant of such weaker susceptibility. Notably, some of the less efficient ecNadD inhibitors (e.g. 3_23 and 15_11) showed a relatively strong antibacterial activity against E. coli. This observation may reflect the existence of additional targets affected by these compounds, non-specific or even sharing some common features with NadD [34]. In addition the inventors demonstrated that 01_02_01 (RK-AL-1) (see Table 12) are effective ecNadD and baNAD inhibitors (FIG. 4).

Example 9

Mechanistic and Structural Analysis of NadD Inhibition

Figure 18:
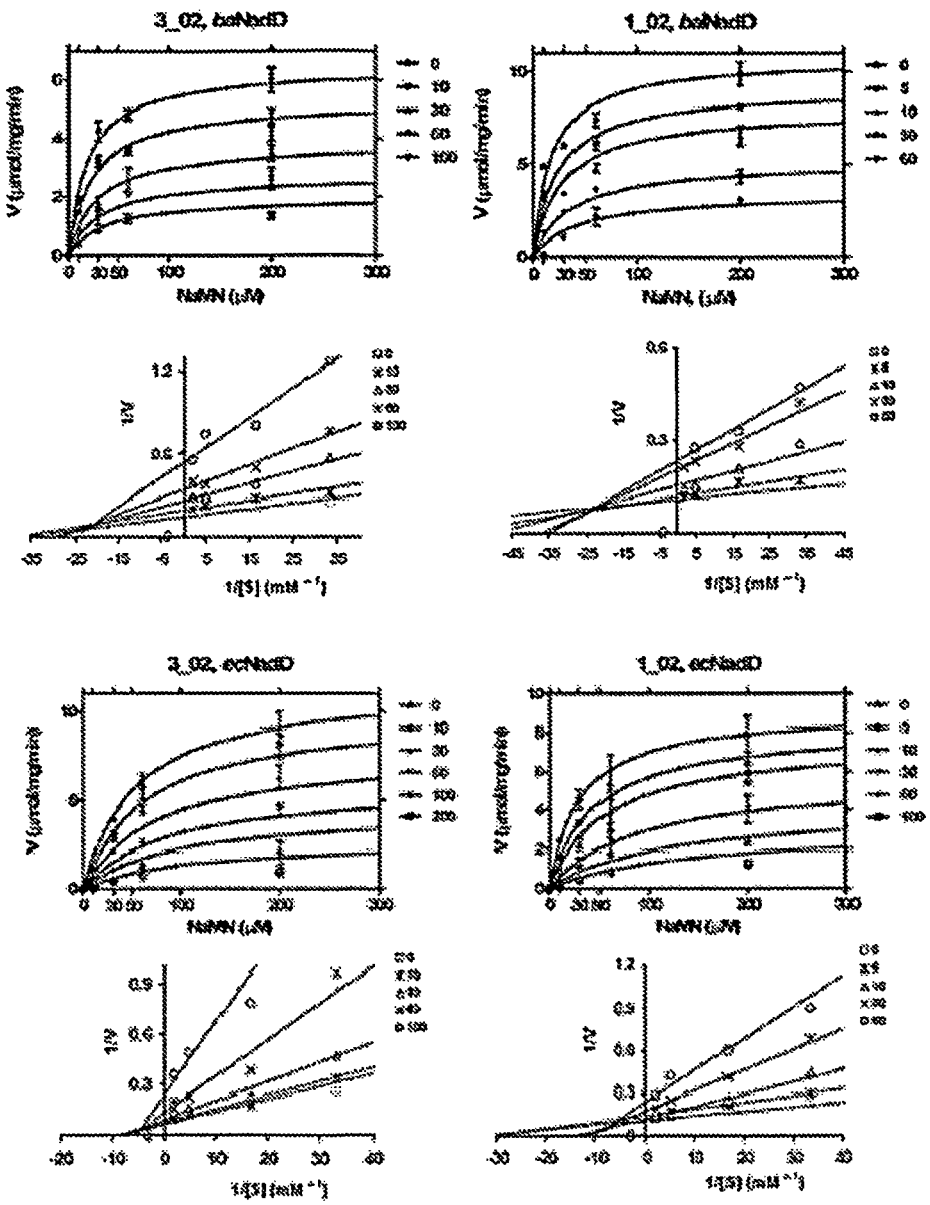
FIG. 18. NadD inhibition by two lead compounds 3_02 and 1_02 Hyperbolic plots of initial reaction rate (∫mol/mg/min) as a function of NaMN substrate concentration (∫M) measured at fixed concentration of the ATP substrate (500 ∫M) in the presence of varying concentrations of compounds 3_02 and 1_02 (0-200 ∫M range). The same data are also presented by a double-reciprocal (Lineweaver-Burk) plot illustrating mixed-type inhibition.

Representatives of both classes 1 and 3 of efficient NadD inhibitors were selected for detailed kinetic characterization and co-crystallization trials. Apparent steady-state inhibitory parameters were obtained for compounds 1_02 and 3_02 against ecNadD and baNadD with respect to each substrate ATP and NaMN (Table 1 and FIG. 18). A preliminary assessment of all kinetic profiles revealed a mixed-type inhibition as indicated by α>1 values obtained by fitting initial rates to a general inhibition model. Despite the observed complex behavior preventing a straightforward mechanistic interpretation, the obtained data showed a substantial similarity in the inhibitory properties of both compounds with respect to both target enzymes.

The 3D structure of the complex of baNadD co-crystallized with compound 3_02 and solved at 2.0-Å resolution revealed its binding in the active-site area mostly through van der Waals interactions. The planar compound stacks against two aromatic residues, Trp116 and Tyr112 (baNadD numbering), and is also in contact with Met109 and Phe103 (FIG. 6A). While there are a few water-mediated indirect interactions between 3_02 and the enzyme, there is no direct intermolecular hydrogen-bond interaction. A comparison with the 3D structure of baNadD complexed with the NaAD product solved in this study at 2.2-Å resolution and with the recently reported apo-baNadD structures [21, 24] provided additional insights to the structural mechanism of inhibition. This comparison revealed that the bound compound 3_02 partially overlaps with the nicotinosyl binding site and would interfere with NaMN substrate binding (FIG. 6B). In particular, inhibitor binding would potentially block the critical stacking interaction between the side-chain of the conserved Trp116 residue with the pyridine ring of the NaMN substrate [19, 22]. This interference may contribute to a competitive aspect of the observed mixed-type inhibition.

The structure comparison also revealed a substantial difference between the active-site conformations in the baNadD-3_02 and baNadD-NaAD complexes. Moreover, the active-site conformation in the baNadD-3_02 complex is much more similar to apo-baNadD (rmsd between $C_\alpha$ atoms 0.77 Å) than to the baNadD-NaAD complex (rmsd of 1.32 Å). The major conformational differences occur in the regions that are involved in NaMN binding, i.e., residues 42-48 (loop connecting β2 and α2), 105-126 (helix α4), and the loop between β5 and β6 (residues 131-149) (FIG. 6B). Notably, these flexible regions correspond to the three regions that deviate the most from the hsNMNAT structure [15]. Without being bound by theory, in addition to interfering with NaMN substrate binding, the interactions between the inhibitor and baNadD may partially "lock" the enzyme active site in the catalytically impaired apo-like conformation. This mechanism provides a rationale for the observed, largely noncompetitive mode of inhibition described above.

The baNadD enzyme has a tendency to form a homodimer as observed in the crystal structure of both, apo-form and of its complex with substrate and confirmed by size-exclusion chromatography and analytical ultracentrifugation (AUC) (data not shown). Inspection of baNadD-3_02 complex crystal packing shows that while the native dimer interface is preserved, an additional dimer interface, similar to that of the "handshake" dimer observed in B. subtilis NadD [22] is also present, resulting in a tetrameric appearance. The 3_02 inhibitor binding site is located at this hand-shake dimer interface. Because the compound binds at a symmetrical site between two baNadD monomers related by a pseudo-twofold symmetry, the two symmetrical orientations of 3_02 cannot be distinguished. Therefore, 3_02 was modeled in both orientations, each with half occupancy.

Although additional interactions between the compound 3_02 and the adjacent baNadD subunit at the handshake dimer interface were observed in the crystal structure, it is unlikely that such interactions would contribute to the inhibition observed in our assay conditions. This conclusion is based on the fact that the enzyme concentration in the assay (~1 nM) was substantially lower than the dimer $K_D$ (0.11 µM) as estimated by AUC analysis. Moreover, AUC data did not reveal any changes in the oligomerization state of the protein in presence of the inhibitor. Therefore, the contribution of the handshake dimer interface to baNadD inhibition by 3_02 should be negligible under the assay conditions. This conclusion is consistent with the fact that ecNadD, being monomeric both in the crystal structure and in solution, exhibits essentially the same inhibitory properties in the presence of 3_02, including the same mixed-type mode and similar kinetic parameters.

Figure 19:
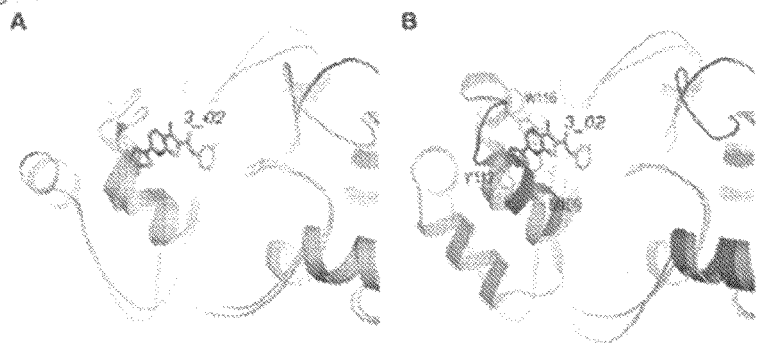
FIG. 19. Structural basis for selective targeting of bacterial NadD (A) Superposition of baNadD-302 complex (magenta) with apo ecNadD (wheat). Inhibitor 302 is shown as magenta sticks.

Notably, the three most flexible regions in baNadD mentioned above also correspond to the regions that deviate the most from the hsNMNAT structure [15] (FIG. 19). Comparison of human NMNAT structures (as represented by hsNMNAT-1 [15]) with various baNadD complexes indicated that hsNMNAT active site conformation is much closer to the product-bound conformation of baNadD than to the apo form of baNadD. No significant conformational change has been observed between the apo and ligand bound human NMNAT enzymes [15, 35, 36]. Therefore the active site of human NMNAT, being quite dissimilar from the apo or inhibitor-bound baNadD, appears unable to accommodate or specifically interact with inhibitor 3_02 (FIG. 19). This interpretation is supported by the results of comparative virtual docking performed for the three classes of active compounds against ecNadD, baNadD, and hsNMNAT-1. The docking energies for the human enzyme consistently have the least favorable scores compared to the energies obtained for ecNadD and baNadD, especially in the van der Waals energy terms, suggesting that the overall shape of the binding region in hsNMNAT is sufficiently different to allow for selective inhibition of bacterial enzymes.

Example 10

Computational Analysis of Inhibitor Selectivity

Docking of selected compounds (Table 2) was performed targeting the binding region into which compound 3_02 was observed to bind in the crystal structure. Docking targeted all available crystal structures of the E. coli (n=2), B. anthracis (n=6) and human (n=4) forms of the enzyme (Table 3). Sphere sets to direct docking were generated using the SPHGEN, selecting sphere sets located in the binding region defined by 3_02 in the crystal structures. Residues adjacent to the sphere sets are listed in Table 3. Docking was performed for each compound against each crystal structure using the secondary screening approach. Table 4 includes the most favorable Dock energy scores for each compound over all the crystal structures for each the three species. With respect to the E. coli and B. anthracis enzymes there is no appreciable correlation with the $IC_{50}$ values reported in Table 2. For example, the $IC_{50}$ values of 1_02 are similar, while docking predicts binding to ecNadD to be favored while with 3_23 the more favorable energy with the baNadD is consistent with the relative $IC_{50}$ values. An interesting outcome of the docking is that a larger number of the compounds have docking energies that are more favorable with baNadD then with ecNadD (9 versus 6, respectively). This may indicate that while docking was performed targeting ecNadD, there is some inherent property of baNadD that leads to favorable ligand-protein interactions. However, this result may be due to the docking analysis being performed against 6 conformations of baNadD versus 2 for ecNadD, where the larger number of conformations increases the probability that a conformation more suitable for a given ligand is targeted. Perhaps more significant are the results when the docking energies are compared for all three species. For all but two of the 15 compounds the least favorable score occurs with hsNMNAT, with the most favorable score occurring for only one compound (3_05). To better understand the types of interactions leading to the less favorable scores with hsNMNAT, the electrostatic and vdW ligand-protein interaction energies were examined. Results in Table 5 show the most favorable electrostatic interaction energies to often occur with the human enzyme while the most unfavorable most often occur with ecNadD. In contrast with the vdW energy, in the majority of cases the human enzyme term is the least favorable, with only two exceptions. To more closely examine the nature of the vdW contribution the attractive vdW interaction energy was calculated. The attractive vdW interaction represents the quality of the steric fit of a ligand with the protein, such that it is used as the compound scoring criteria for the primary screen methodology in this study. Results in Table 6 show that hsNMNAT has the least favorable attractive vdW interaction energy in all but one case. Although the docking approaches and, scoring functions used in the analysis are very approximate, the observed vdW terms were consistently most unfavorable for hsNMNAT suggesting that the overall shape of the binding region of the human enzyme differs enough from that of ecNadD and baNadD to afford the observed selective inhibition. The attractive vdW results show baNadD to typically have the most favorable values.

Additional Results

Structure of baNadD in Complex with Inhibitor 1_02

The complex of baNadD and 1_02 crystallized in the same space group $P2_12_12$ as the previously reported baNadD-3_02 complex[414] and the protein conformations in the two inhibitor complexes are also very similar with root mean square deviation (RMSD) for all $C_\alpha$ atoms of 0.175 Å; they resemble the conformation of the enzyme in its apo state rather than the substrate or product bound state, with RMSD values of 0.494 Å and 0.833 Å, respectively, compared to the apo and product bound baNadD[414, A21, A22] (Reference A14, Sorci et al, *Targeting NAD biosynthesis in bacterial pathogens: Structure-based development of inhibitors of nicotinate mononucleotide adenylyltransferase NadD*, Chem Biol, Aug. 28, 2009, 16, 849-861 and Sorci et al, *Supplemental Data: Targeting NAD biosynthesis in bacterial pathogens: Structure-based development of inhibitors of nicotinate mononucleotide adenylyltransferase NadD*, Chem Biol, Aug. 28, 2009, 16, 849-861 and Huang et al, *Complexes of Bacterial Nicotinate Mononucleotide Adenylyltransferase with Inhibitors: Implication for Structure-Based Drug Design and Improvement*, J. Med. Chem., Jun. 25, 2010 (web) are each hereby incorporated by reference in their entirety.

Figure 9:
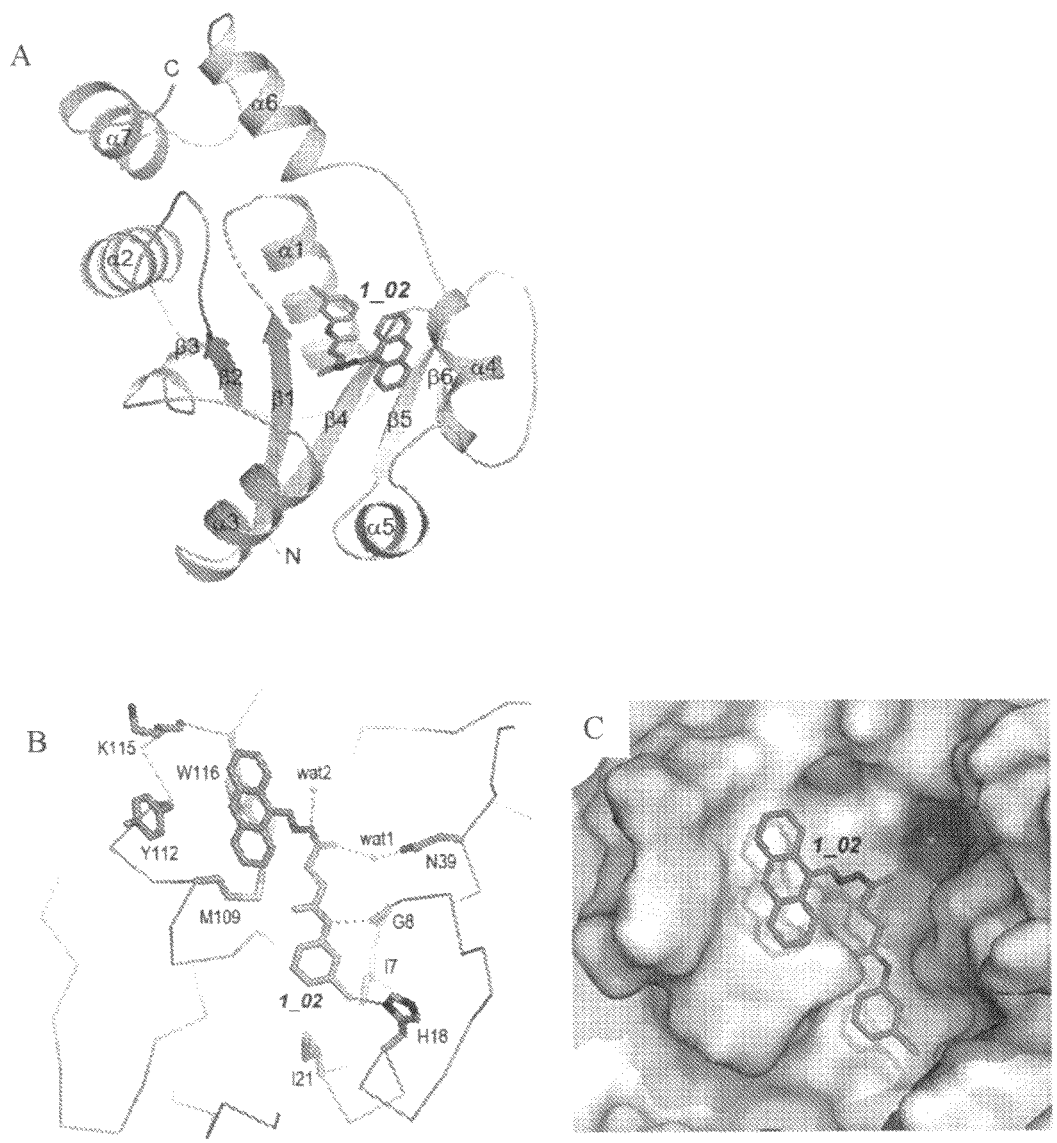
FIG. 9. Interactions of 1_02 with baNadD. (A). Ribbon representation of baNadD-1_02 complex. Inhibitor 1_02 is shown as sticks. (B). Detailed interactions between 1_02 and baNadD residues. The $C_\alpha$ trace of the protein is shown; relevant side chains are shown as sticks. Hydrogen bonds are shown as dotted lines. Water molecules are shown as small red spheres. C). Surface representation of the inhibitor binding site on baNadD, colored by the electrostatic potentials. Three water molecules adjacent to 1_02 are shown as green spheres.

Inspection of the electron density for the bound compound revealed a symmetrically shaped density much larger than the compound (FIG. 8A). This density is located at a symmetrical interface between two baNadD monomers where the inhibitor can bind in one of two different but symmetrically related orientations, with the positions of the central anthracene ring overlapping with each other (FIGS. 8A and 8B). These two orientations are in fact equivalent and physically indistinguishable. It can be viewed as such that in the complex crystal, half of the protein molecule population would bind the inhibitor in one orientation, while the other half bind the inhibitor in the second orientation. The resulted electron density is the accumulated average from all the complex molecules in the crystal. Therefore Applicants modeled 1_02 molecule in two orientations each with half occupancy (FIG. 8).

baNadD structures have been reported recently in its apo form, in complex with substrate NaMN, with product NaAD, as well as with inhibitor 3_02[414, A21, A22]. The overall baNadD structure contains a Rossman-fold core with a central six-stranded parallel β-sheet and two or three α helices on each side of the sheet (FIG. 9A). Following the sixth and the last β strand, two α helices (α6 and α7) form a small C-terminal subdomain that is characteristic of the nucleotidyltransferase superfamily. The signature HxGH motif ($_{15}$HYGH$_{18}$) is located in the loop connecting the first β-strand (β1) and succeeding α helix (α1). This motif is involved in the interaction with the phosphate groups of the substrates (ATP and NaMN) and participates in the catalysis.

In the baNadD-1_02 complex structure, 1_02 sits at a central cleft between strands β1 and β4 of the β sheet, which is the catalytic and substrate binding sites of the enzyme (FIG. 9A). The compound is bent at the acylhydrazone linkage and follows the contour of the crevice of the substrate binding site (FIGS. 9B and 9C). The anthryl rings together with the acylhydrazone of the compound stack against the side chains of Trp 116, Tyr112 and Met109 (FIG. 9B). A single direct hydrogen bond is formed between the amide group of the carboxyamide moiety of 1_02 to the main chain carbonyl of Gly8. The chloride of the terminal chlorophenyl group appears to interact favorably with the side chain of His18 of the HxGH motif. There are two indirect hydrogen bonds between the compound and protein atoms. One is formed between the hydrazone amide and the side chain of Thr85 via a water molecule (wat1), and the other between the acyl oxygen group and Asn39 side chain through wat1. The chlorophenyl ring is also in contact with the side chains of Ile 7 and Ile 21, which may provide additional stabilizing van der Waals interactions with the compound (FIG. 9B).

Comparison of the Binding Modes of 1_02 and 3_02

Figure 10:
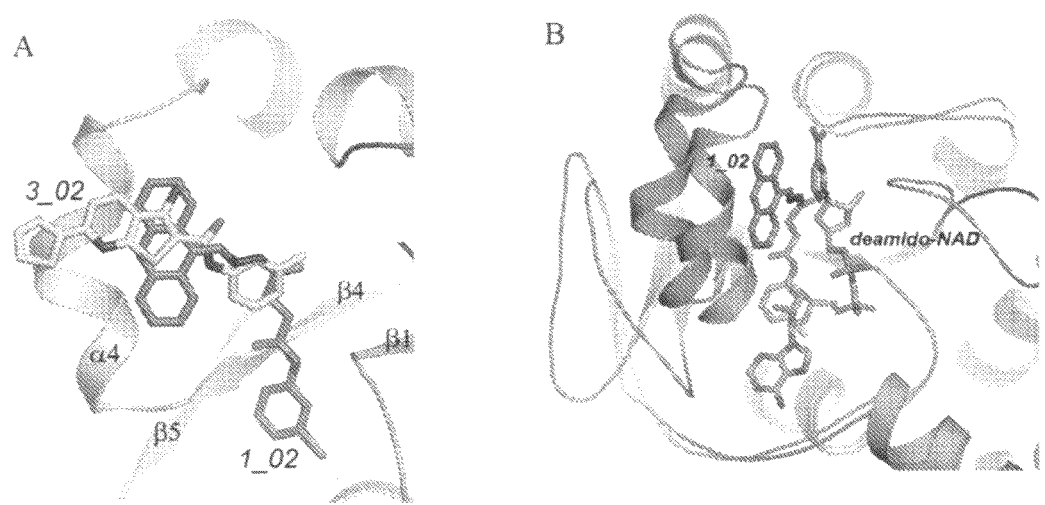
FIG. 10. Comparison of the binding modes of 1_02 (magenta), 3_02 (yellow), and the product deamido-NAD (blue). (A). Superposition of baNadD bound 102 with 3_02 showing the overlapping binding mode. The protein conformations of the two structures are essentially identical and a single ribbon diagram is shown. (B). Superposition of the baNadD-1_02 complex (orange) with the baNadD-product complex (cyan). 1_02 is in magenta; the product deamido-NAD is in blue.

Comparison of the binding mode of 1_02 and that of 3_02 reported previously[414] shows that the nearly coplanar anthracene rings and the hydrazone portion of 1_02 overlaps with the largely planar 3_02 (FIG. 10A). They form similar stacking and van der Waals interactions with multiple protein residues including Trp116, Tyr112, Met109 and Lys115. This shared binding site corresponds to the region that binds nicotinic acid riboside portion of NaMN substrate in the absence of the inhibitors (FIG. 10B). In particular, Trp116 would stack against the pyridine ring of NaMN and is critical for the proper positioning of the substrate. Therefore binding of the inhibitors would prevent NaMN binding all together. Notably, the two classes of compounds do not overlap completely and each has additional interactions with the enzyme that are not present in the other compound (FIG. 10A). While 3_02 largely overlaps with the NaMN substrate binding site, 1_02 also intrudes into the ATP binding pocket and its chlorophenyl group would overlap with the ribose of ATP (FIG. 10B). The inhibitory efficiencies of the two compounds against haNadD have been determined previously, with 1_02 having $K_i$ of 9 μM and 10 μM, respectively, with regard to NaMN and ATP substrates; while 3_02 has $K_i$ of 18 μM and 32 μM against NaMN and ATP, respectively[414]. These values are consistent with the structural observation that 1_02 interferes with binding of both NaMN and ATP whereas 3_02 mostly interferes with NaMN binding.

Binding of both 1_02 and 3_02 appears to stabilize the enzyme in a conformation that is significantly different from its substrate or product bound form, and is apparently catalytic incompetent (FIG. 10B). The conformational differences associated with inhibitor binding as compared to the substrate or product bound conformations has been suggested to lead to mixed inhibition kinetics that contains both competitive and non-competitive characters[414].

Structure of baNadD in Complex with Inhibitor 1_02_1

Because 1_02 must adopt either of the two symmetrically related orientations with half occupancy in the crystal due to the overlapping position of the anthracene rings, Applicants hypothesized that a symmetrical compound that fit the observed density of 1_02 would bind to the enzyme with full occupancy and higher affinity. A compound was designed to retain the central planer ring system with an acylhydrazone arm and terminal chlorophenyl ring on each side. The resulting compound, designated 1_02_1 (Scheme 1) (FIG. 15), was synthesized and subjected to biochemical and crystallographic analysis. Compound 1_02_1 replaced the anthracene ring with a benzene and includes a Cl atom at the ortho position of the terminal phenyl rings; this selection was based on availability of chemical precursors. 1_02_1 was then tested as a NadD inhibitor. According to the structure activity relationship (SAR) data from a limited set of analogs of Class 1 compounds (FIG. 11A), it was expected that 1_02_1 should have an improved activity compared to the different asymmetric "monomeric" compounds. Inhibition assay on 1_02_1 yielded an $IC_{50}$ of 13±2 μM and 16±4 μM against ecNadD and baNadD, respectively (FIG. 11B). Compared to the Class I analogs shown in FIG. 11A, 1_02_1 is significantly better than those compounds with either a benzene or naphthalene rings, while its activity is similar to those compounds containing an antharcene ring, including 1_02. As 1_13 and 1_15 in FIG. 11A contain only benzene rings and linkers identical to 1_02_1, they may be considered as "precursors" of 1_02_1. Therefore the design strategy to create a symmetrical compound may be considered successful, as a more than 10 fold improvement in activity was achieved. 1_02_1 is also slightly more active than compound 1_02, which has an $IC_{50}$ of 25 μM.

To understand the binding mode of 1_02_1, Applicants determined the crystal structure of baNadD in complex with the compound. The baNadD-1_02_1 complex has the same crystal form as the 1_02 complex and retains the crystal lattice packing involving the same monomer-monomer interface to which the inhibitor binds. 1_02_1 has well defined electron density and is modeled with full occupancy (FIG. 12A). As predicted, 1_02_1 binds at the same site as 1_02 and overlaps with the two orientations of that molecule (FIG. 12B). The conformations of the acylhydrazone arms of the two compounds are very similar despite the presence of several rotatable bonds (FIG. 12B). 1_02_1 also interacts with the protein similarly as 1_02. Most van der Waals interactions, especially the stacking interactions with Trp116 and Tyr112, are preserved (FIG. 12C). However, due to the difference in the central ring systems and the restriction of the covalent linkage to the central benzene ring, the acylhydrazone arms of 1_02_1 displays a slight rigid body rotation (~15° compared to 1_02. As a result, there are differences in the hydrogen bond patterns and in the orientation of the end chlorophenyl group. The hydrogen bond between the carboxyamide nitrogen of 1_02 and Gly8 main chain (shown in FIG. 9B) is lost in the 1_02_1 complex structure, whereas a new hydrogen bond is formed between the carboxyamide oxygen and Gly106 main chain amide (FIG. 12C). The smaller single six-membered central ring of 1_02_1 may lead to a decrease in the van der Waals interactions with the protein as compared to the anthracene ring in 1_02.

Interestingly, in the 1_02_1 complex structure, two well-ordered formate molecules are observed mediating specific interactions between the acylhydrazone amide group and the main chain amide and side chain hydroxyl of residue Thr85 (FIG. 12C). In the NaMN or NaAD complex structure, the carboxylate group of the nicotinic acid binds in this region and interacts with the main chain amide of Thr85. Thus, the formate molecule observed in the 1_02_1 complex structure mimics the interaction between the nicotinic acid carboxylate group of the substrate NaMN and the enzyme.

Carboxylate Containing Analogs of 1_02 and 1_02_1

Motivated by the presence of the formates in the 1_02_1 complex structure, additional analogs were designed. These analogs (1_02_2 and 1_02_3 in Scheme 3) (FIG. 17) were designed to include a carboxylate moiety to approximate the location of the formates in the baNadD-1_02_1 complex structure. In that structure, one formate oxygen is 2.76 Å from the side chain hydroxyl group of Thr85 and the other oxygen is 2.91 Å from the backbone amide nitrogen of Thr85, forming a well-defined ion-dipole interactions. Accordingly, it was hypothesized that the carboxylate moieties would mimic these interactions, thereby further improving binding. In addition, the inclusion of the carboxylate moieties would enhance the solubility of the compounds, making them more suitable for biochemical experiments and potentially enhance their bioavailability. This led to the design and synthesis of 1_02_2 and 1_02_3 shown in Scheme 3 (FIG. 17). 1_02_2 was a direct mimic of 1_02_1 while 1_02_3 was designed as an analog of 1_02, to test if the presence of the carboxylate could improve the affinity of the monomeric species.

Experiments were then undertaken on the two new 1_02 analogs to measure the inhibitory activity against baNadD. Surprisingly, 1_02_2 did not inhibit baNadD at concentrations up to 100 μM, while 1_02_3 only weakly inhibits baNadD activity ($IC_{50}$>200 μM). Thus, the inclusion of the carboxylates did not lead to improved binding with the symmetric, dimeric analog 1_02_02, although some binding affinity of the monomer analog, 1_02_3 is present.

Figure 13:
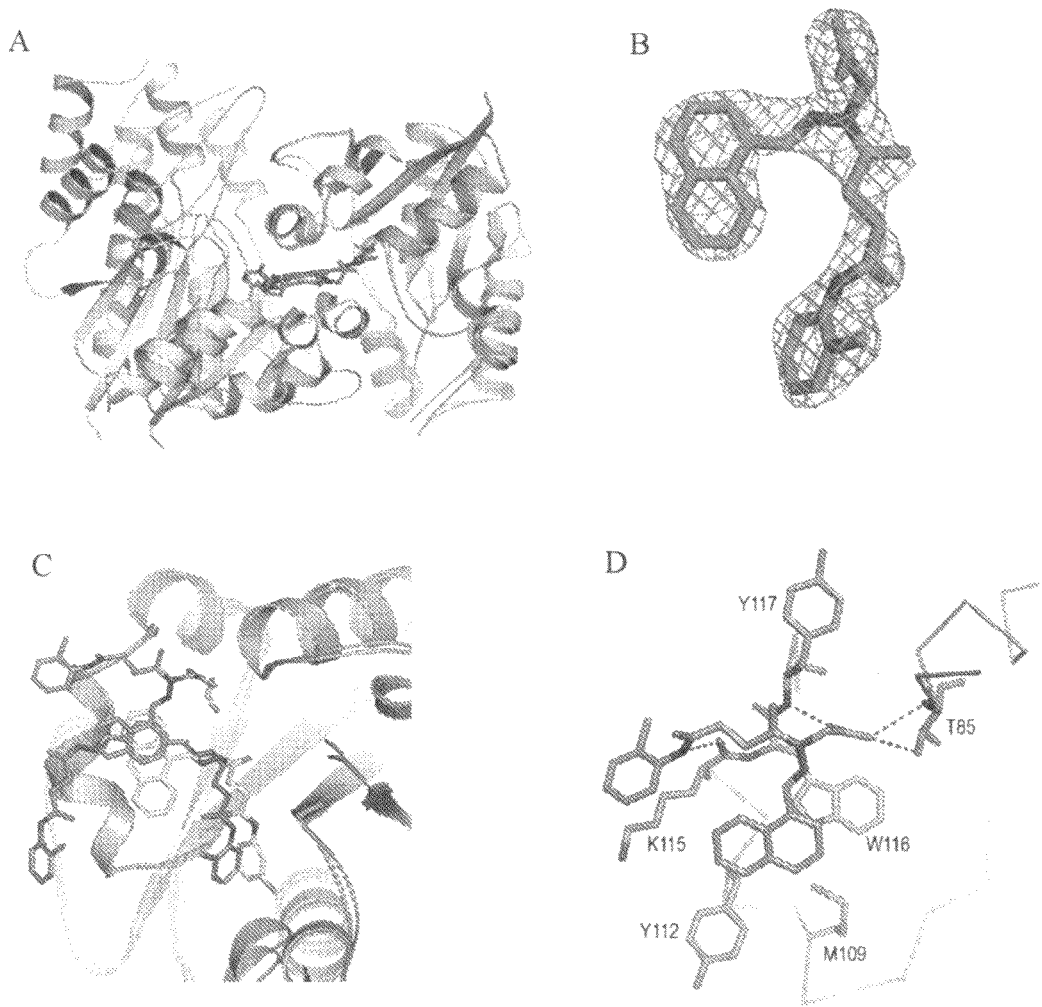
FIG. 13. Structure of baNadD-1_02_3 complex. A). Compound 1_02_3 (blue sticks) binds between two baNadD monomers (colored cyan and light cyan), which have a difference interface from that in the 1_02_1 complex. The two monomers of baNadD in the 1_02_1 complex are colored light pink with one monomer superimposed onto the cyan monomer of the 1_02_3 complex. (B). The Fo-Fc omit map for 1_02_3. (C). Superposition of the three enzyme-bound Class/inhibitors showing the common aromatic binding site as well as differences in the binding mode of each compound. The protein molecules in the 1_02_1 and 1_02_3 complexes are shown in light pink and cyan, respectively. (B). Detailed interactions between 1_02_3 and baNadD residues.

To understand the unexpected results, both 1_02_2 and 1_02_3 were subjected to crystallographic analysis. All attempts to cocrystallize 1_02_2 with baNadD were unsuccessful; however, cocrystals of 1_02_3 bound to baNadD were obtained and the complex structure was determined to 2.55 Å resolution. The 1_02_3 complex crystal is in a different space group (C2) from all other baNadD-inhibitor complexes, and contained eight baNadD monomers in the asymmetric unit. Notably, the baNadD monomer-monomer interface to which 1_02_3 binds is different from that observed in all other inhibitor complex structures (FIG. 13A), indicating that packing of the enzyme molecules in the crystal can be influenced by inhibitor binding. The electron density for 1_02_3 was well-defined allowing unambiguous modeling of the compound in the complex (FIG. 13B). Interestingly, the binding mode of 1_02_3 differs significantly from that of 1_02 and 1_02_1, although some overlap is present (FIG. 13C). In particular, the naphthalene ring of 1_02_3 binds to the same site as the aromatic rings of the other Class 1 compounds, and form similar van der Waals contacts with Trp116, Tyr112, Met 109, as well as with Lys115. However, the acylhydrazone arm and the end chlorobenzene ring of 1_02_3 adopt completely different conformations from that of compounds 1_02 and 1_02_1, and interact with different functional groups on the protein. In this binding mode, the carboxylate group of the compound, though occupying a similar position as the formate molecule in the 1_02_1 complex, interacts with the enzyme somewhat differently. One oxygen of the carboxylate still interacts with the side chain hydroxyl of Thr85 (3.13 Å). In addition, there are ion-dipole interactions of the carboxylate with the main chain amides of Thr85 (3.30 Å) and of Tyr117 (2.81 Å) (FIG. 13D). These interactions are reminiscent of those observed in the NaMN substrate complex where the carboxylate of the substrate also forms two hydrogen bonds with the main chain amides of both Thr85 and Tyr117[414, 422]. An additional hydrogen bond between the amide group of 1_02_3 and the main chain carbonyl of Lys115 is also observed (2.8 Å). Overall, these interactions lead to a different binding mode for 1_02_3 even though the aromatic and acidic groups bind to the sites as predicted based on the 1_02_1 complex. In this mode the carboxy amide moiety and adjacent chlorophenyl ring of the compound are largely exposed to the solvent while their counterpart in the 1_02 and 1_02_1 complexes binds to the adenosine binding site of the enzyme and is much less solvent accessible.

The 1_02_3 complex structure provides a possible explanation as to why 1_02_2 does not bind as anticipated. While the naphthalene ring and carboxylate moieties bind to the anticipated sites, the geometrical restraints to achieve these interactions leads to a reorientation of the compound and a significant change in the overall binding mode of 1_02_3 (FIGS. 13C and 13D). Potential binding of 1_02_2 in the same orientation as 1_02_3 would disallow the second arm of the hydrazine linker to access the binding pocket occupied by 1_02 and 1_02_1, thereby abolishing binding.

Discussion

Figure 14:
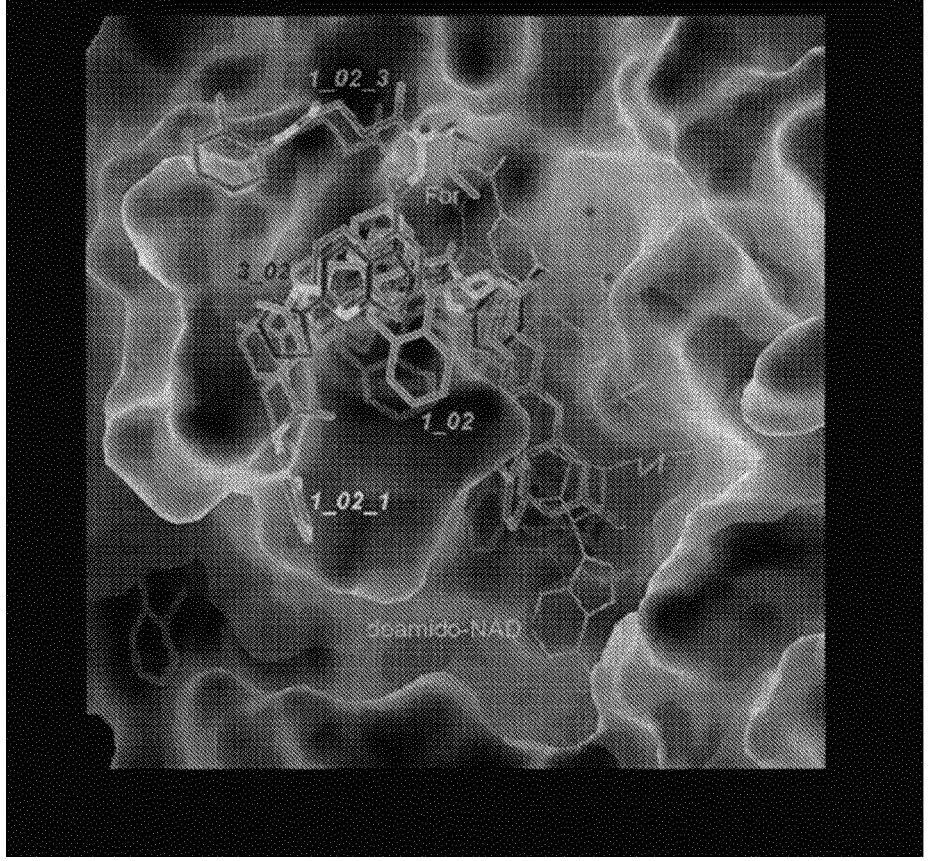
FIG. 14. Superposition of the baNadD bound 3_02 (yellow), 1_02 (magenta), 1_02_1 (blue) and 1_02_3 (green). The surface presentation of the enzyme (colored according to electrostatic potentials) in the 1_02 complex structure is shown. The image also includes three nearby water molecules observed in the 1_02 complex structure (cyan spheres) and the formate molecule observed in the 1_02_1 complex structure. The orientation of deamino-NAD+ (thin, atom-colored licorice representation) from the product-complex structure (pdb code 3e27) is also shown.

In an effort to develop inhibitors targeting the essential bacterial NadD enzymes, Applicants have identified three classes of bacterial NadD inhibitors with distinct scaffolds in a structure-based in sillico screen[414]. Applicants have also obtained the crystals structures of *B. anthracis* NadD in complex with inhibitors from two different chemical classes: 3_02 from Class 3 (reported in Ref. 14), and three different Class 1 compounds (1_02, 1_02_1 and 1_02_3). The complex structures of baNadD with different inhibitors revealed a common binding site near residues Trp116, Try112, and Met109, as shown in FIG. 14, which appears to have an affinity for aromatic groups from different small molecules. This site overlaps but is distinct from the substrate NaMN binding pocket, and may serve as a primary site to be targeted in future inhibitor design efforts. Such design efforts would target compounds whose aromatic moieties interact with the identified "aromatic" site, with the remainder of those putative molecules sampling various binding modes in the vicinity of this site.

The compounds of the present invention also include ones that interact with an inhibitor binding pocket of baNAdD at one or more residues selected from Trp 116, Tyr112, Met109, Lys115 and Phe103. The compounds of the present invention are not limited to ones that interact with an inhibitor binding pocket of baNAdD, but may also be ones that interact with a similar site defined by homologous residues on any bacterial NadD protein. FIGS. 6-10, 12-14 and 19 also show some residues that are not located at the common binding site.

The complex structures of three Class 1 compounds provide useful information about the chemical characters of the inhibitor-binding site of NadD. Compounds 1_02 and 1_02_1 bind to the aromatic site with their central anthracene or benzene rings and hydrazone groups; while the linker and the terminal chlorobenzene ring intrude into a deep groove on the enzyme and interact directly with the conserved active site HxGH motif residues. In addition to this groove, the binding potential of a small pocket adjacent to the primary binding site is highlighted in the 1_02_1 and 1_02_3 complex structures, where it is revealed that this pocket favors binding of a carboxylate group. In the 1_02_3 complex structure, binding of the carboxylate group at this site comes at the expense of completely reorienting the acylhydrazone arms of the compound which results in an overall decreased affinity. This reorientation is also proposed to disallow binding of the dimeric 1_02_2 to the protein.

Although the activities of the current NadD inhibitors are only in the low micromolar $IC_{50}$ range at best, there are several attractive features in their binding modes. Binding of both classes of inhibitors appears to stabilize the enzyme in a catalytically incompetent conformation, significantly different from its substrate or product bound conformation, resulting in a mixed inhibition kinetics behavior that contains both competitive and non-competitive characters. As such the binding pocket can accommodate small molecules with structures very different from the natural ligands of the enzymes. Therefore, such small molecule binders are anticipated to have minimal adverse effects on the numerous other $NAD^+$ or ATP utilizing enzymes. The non-competitive character of inhibition by these inhibitors also indicates that once higher affinity compounds are found, they may not be strongly influenced by cellular ATP or $NAD^+$ concentrations, which are on the order of $\sim 10\text{-}10^3$ $\mu M^{427\text{-}429}$. Such inhibitors could have better in vivo efficacy than purely competitive inhibitors.

Although a non-native dimer interface is observed in several baNadD-inhibitor (e.g., 3_02, 1_02 and 1_02_1) complex crystal structures, it has become clear that this dimerization mode is due to crystal lattice packing interactions under specific crystallization conditions since such dimerization is not observed in solution in an analytical ultracentrifugation study[414]. Crystal structures of 1_02_3 complex and apo-baNadD obtained in different space groups also do not have the same dimerization mode[421, 422]. This observation partially explains the moderate improvement of the activity of the much larger dimeric 1_02_1 as compared to its monomeric precursor. Therefore future inhibitor design and optimization effort should be focused on engineering specific direct interactions between the inhibitors and enzyme monomer. Toward this goal, the complex structures of NadD with different inhibitors provided useful information on a common primary target site and the chemical environment of the vicinity of this site which can be exploited to improve on the existing inhibitor scaffolds or design high affinity inhibitors with novel scaffolds for maximum interaction with the enzyme.

Experimental Section

Protein Crystallography

The expression and purification of *Bacillus anthracis* NadD (baNadD) has been reported elsewhere[414]. For co-crystallization of baNadD with compounds 1_02, 1_02_1 and 1_02_3, appropriate amount of the stock compound solutions (20 mM in DMSO) was mixed with the protein to the final concentration of 1 mM, while the final protein concentration is 19 mg/ml. The PEG/Ion Crystallization Screening kit (Hampton Research) was used for the initial screens of the complex crystals. Hanging drop vapor diffusion methods were used for the crystallization where equal volume (1.5 µl) of the complex and reservoir solution was mixed and equilibrated against the reservoir at 20° C. The baNadD-1_02 cocrystals were obtained in conditions that contain 0.2-0.25 M magnesium formate and 20%-24% PEG 3350. The baNadD-1_02_1 complex crystals were obtained from 0.2M potassium formate and 20% PEG 3350. Both crystals were cryoprotected in solutions that contained an increased concentration of PEG 3350 (40%) and original components of the reservoir and frozen in liquid propane. The baNadD-1_02_3 complex formed crystals in 0.2 M potassium citrate and 20% PEG 3350, and the crystal was frozen in the cryoprotectant containing original components of the reservoir supplemented with 10% DMSO and flash frozen in liquid nitrogen.

The X-ray diffraction data of the baNadD-1_02 complex crystal was collected at beamline 19BM, Advanced Photon Source, Argonne National Laboratory, whereas the data for baNadD-1_02_1 and baNadD-1_02_3 crystals were collected in-house on a Rigaku FRE rotating anode X-ray generator equipped with Osmic focusing device and RAMS IV++ image plate detector. The data were further processed using HKL3000 software[430].

Both the baNadD-1_02 and baNadD-1_02_1 complexes were crystallized in the $P2_12_12$ space group, isomorphous to the crystals of baNadD-3_02 complex reported recently[414]. Therefore, the model of the baNadD-3_02 (pdb code 3hfj), excluding ligand and solvent molecules was used as the initial model for the refinement of both new complexes using the program Refmac of the CCP4 package[431-433]. The solution of baNadD-1_02_3 complex was found by the molecular replacement method of Phaser[434] using apo baNadD as the starting model. Model inspection and adjustment was performed with Coot[435]. The electron densities for compound 1_02, 1_02_1 and 1_02_03 were clearly visible in the early stage of the refinement. The PRODRG server[436] was used to generate the models for the compounds to be included in the complex structure. Final rounds of refinements were performed using PHENIX[437, 438] and the model geometry was monitored by Molprobity[439]. The crystal data and refinement statistics of these complexes are list in Table 14. The coordinates have been deposited in the Protein Data Bank[440] with accession codes 3MLA, 3MLB, and 3MMX.

Enzyme Inhibition Assay

A general phosphate detection assay method using Malachite Green reagent was adapted to measure the activity of NaMN adenylyltransferase[414]. Briefly, the byproduct of NadD catalyzed reaction, inorganic pyrophosphate (PPi), was hydrolysed by inorganic pyrophosphatase and the resulting orthophosphate was detected by the Malachite Green dye. The reaction mixture contained 2.3 nM ecNadD (or 1.2 nM baNadD) in 100 mM Hepes, pH 7.5 buffer, 0.2 mM ATP, 0.07 or 0.2 mM NaMN, 10 mM $MgCl_2$, 0.1 mg/ml Bovine Serum Albumin, 0.2 U inorganic pyrophosphatase. Appropriate amount of inhibitors were added to the reaction mixture to assess their effect on enzyme activity. After preincubation of the enzyme with the compounds for 5 min at room temperature, the reaction was started by adding NaMN substrate. The reaction was quenched with two volumes of Malachite Green Reagent in 1.2 M sulfuric acid prepared as described by Cogan et al.[441]. After 20-30 min incubation to allow for complex/color formation, the absorbance was measured at 620 nm. To account for possible contribution of free phosphate and/or pyrophosphate (present in the sample or released due to non-specific hydrolysis of ATP) as well as of background absorbance (color) of the tested compounds, parallel reactions were run for each experimental point without addition of NadD enzymes, and their $OD_{620}$ values were subtracted from the measurements of enzyme activity in respective samples. Reaction in the presence of 2% DMSO but without inhibitor served as the positive control.

For $IC_{50}$ determination, the initial rate of the enzymatic reaction was measured at fixed NaMN and ATP concentrations (equal to two-fold $K_m$ values) in the absence and presence of various concentrations of inhibitors. The $IC_{50}$ value was determined by plotting the rates versus inhibitor concentration and fitting to the equation (I) using GRAPHPAD PRISM®.

$$v_i = v_0/(1 + [I]/IC_{50}) \quad (1)$$

$v_0$ and $v_i$ represent initial rates in the absence and presence of inhibitors at concentration [I].

Chemistry

Proton NMR spectra were recorded on Varian 500 MHz FT NMR spectrometers. Mass spectra were recorded on a LCQ mass spectrometer (Finnigan MAT, San Jose, Calif.). Element analyses were performed by Atlantic Mircolab, Inc. (Norcross, Ga.). Flash column chromatography was performed using Silica Gel 60 (230-400 mesh) from Thomas Scientific (Swedesboro, N.J.). Analytical thin layer chromatography (TLC) was performed on precoated glass backed plates from Analtech Inc. (Newark, Del.) (TLC uniplates, Silica gel GHLF, 250μ). Plates were visualized using ultraviolet, iodine vapors, phosphomolybdic acid or ninhydrin. Compound 1 was available from commercial supplier. The purity of the compounds, as determined by GCMS, was ≥95%.

Figure 15:
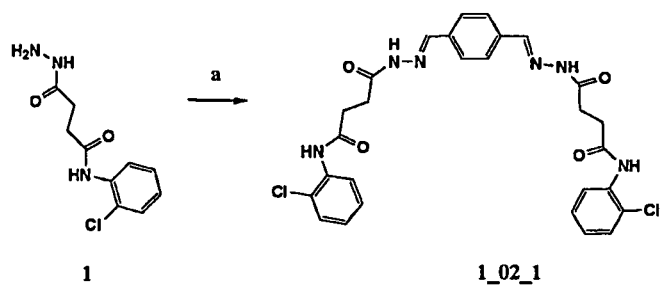
FIG. 15. Scheme 1. Synthesis of compound 1_02_1

Synthesis of N-(2-Chloro-phenyl)-3-(4-{[3-(2-chloro-phenylcarbamoyl)-propionyl]-hydrazonomethyl}-benzylidene-hydrazinocarbonyl)-propionamide (1_02_1, Scheme 1) (FIG. 15).

Benzene-1,4-dicarbaldehyde (0.01 g, 0.07 mmol) and N-(2-Chloro-phenyl)-3-hydrazinocarbonyl-propionamide 1 (0.036 g, 0.14 mmol) in ethanol (5 mL) were heated to reflux for 2 h. After cooling to room temperature, the precipitate was filtered off and washed with ethanol to give 1_02_1 as a pale white solid (0.03 g, 69%). $^1$H NMR (500 MHz, DMSO-d6) 12.31 (2H, s), 8.21 (2H, s), 7.94 (4H, s), 7.60-8.20 (8H, br); MS Anal. Mol. Wt. 580.14 (604.2 M+Na). Elemental Analysis Calculated for C28H26Cl2N6O4 0.4H2O: C, 57.13; H, 4.58; N, 14.27. Found: C, 57.36; H, 4.49; N, 14.00.

Figure 16:
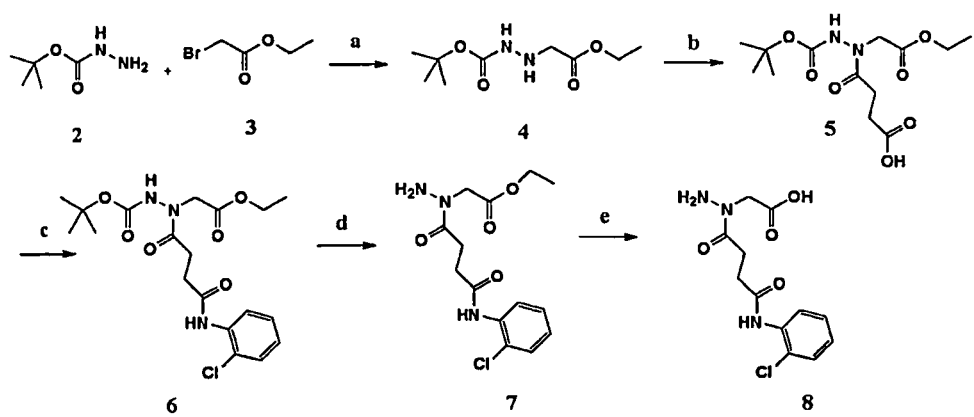
FIG. 16. Scheme 2. Synthesis of Compound 8 {N-[3-(2-Chloro-phenylcarbamoyl)-propionyl]hydrazino}-acetic acid FIG. 17. Scheme 3. Synthesis of 1_02_2 and 1_02_03

Synthesis of (N'-tert-Butoxycarbonyl-hydrazino)-acetic acid ethyl ester (4, Scheme 2) (FIG. 16)

Ethyl bromoacetate 3 (6.97 mL, 62.8 mmol) was added to a stirred solution of tert-butylcarbazate 2 (24.9 g, 188.6 mmol) in water (25 mL) at room temperature. The mixture was stirred for 30 min. Water layer was then extracted with ethyl acetate (3×). Ethyl acetate extracts were pooled together and washed with brine. Ethyl acetate was evaporated under vacuum to get crude product which was purified by flash column chromatography using hexane:ethyl acetate (70:30) as an eluent (yield 70%). $^1$H NMR (500 MHz, CDCl$_3$) 1.28 (3H, CH$_2$—CH$_3$, t), 1.45 (9H, C—CH$_3$, s), 3.64 (2H, NH—CH$_2$—CO, s), 4.20 (2H, CH$_2$CH$_3$, q); MS Anal. Mol. Wt. 218.25 (M+1).

Synthesis of 4-(N'-tert-Butoxycarbonyl-N-ethoxycarbonylmethyl-hydrazino)-4-oxo-butyric acid (5, Scheme 2) (FIG. 16)

Into a solution of (N'-tert-Butoxycarbonyl-hydrazino)-acetic acid ethyl ester 4 (1.85 g, 18.5 mmol) in DMF (30 mL) was added succinic anhydride (4.84 g, 22.2 mmol) and the mixture was stirred at 75° C. for 18 h. DMF was evaporated and the crude mixture was purified by flash column chromatography using hexane:ethylacetate (1% acetic acid) as an eluent (yield 50%). $^1$H NMR (500 MHz, CDCl$_3$) 1.28 (3H, CH$_2$—CH$_3$, t), 1.48 (9H, C—CH$_3$, s), 2.55-3.00 (6H, NH—CH$_2$—CO, N—CH$_2$—CH$_2$—CO, m), 4.20 (2H, CH$_2$CH$_3$, q); MS Anal. Mol. Wt. 318.25 (M−1).

Synthesis of {N'-tert-Butoxycarbonyl-N-[3-(2-chloro-phenylcarbamoyl)-propionyl]-hydrazino}-acetic acid ethyl ester (6, Scheme 2) (FIG. 16)

Into a mixture of compound 5, HBTU and DIPEA in DMF was added 2-chloroaniline and the solution was stirred for 48 h. DMF was evaporated under vacuum and the mixture was dissolved in ethyl acetate and washed with water (2×), 1M $KHSO_4$ (2×) and water (2×). Ethyl acetate was then evaporated to get crude compound which was purified by flash column chromatography using hexane:ethyl acetate (50:50) as an eluent (yield 38%). NMR (500 MHz, $CDCl_3$) 1.27 (3H, $CH_2$—$CH_3$, t), 1.48 (9H, C—$CH_3$, s), 2.58-3.06 (6H, NH—$CH_2$—CO, N—$CH_2$—$CH_2$—CO, m), 4.20 (2H, $CH_2CH_3$, q), 7.01 (1H, ArH, t), 7.22-7.27 (1H, ArH, m) 7.34 (1H, ArH, d), 8.06 (1H, ArNH, s), 8.33 (1H, ArH, d); MS Anal. Mol. Wt. 427.88 (M+23).

Synthesis of {N-[3-(2-Chloro-phenylcarbamoyl)-propionyl]-hydrazino}-acetic acid ethyl ester (7, Scheme 2) (FIG. 16)

Compound 6 (0.3 g, 0.7 mmol) was dissolved in 5 mL of 20% TFA in dichloromethane and the solution was stirred for 1 h. TFA was then evaporated under vacuum and the crude mixture was purified by flash column chromatography using ethyl acetate as an eluent (yield 87%). $^1$H NMR (500 MHz, $CDCl_3$) 1.27 (3H, $CH_2$—$CH_3$, t), 2.75 (2H, N—$CH_2$—$CH_2$—CO, t), 3.11 (2H, N—$CH_2$—$CH_2$—CO, t), 4.20 (2H, $CH_2CH_3$, q), 4.36 (2H, NH—$CH_2$—CO, s), 7.00 (1'-1, ArH, t), 7.23 (1H, ArH, t) 7.33 (1H, ArH, d) 8.24-8.40 (2H, ArNH, ArH, m); MS Anal. Mol. Wt. 327.76 (M+1).

Synthesis of {N-[3-(2-Chloro-phenylcarbamoyl)-propionyl]-hydrazino}-acetic acid (8)

Compound 7 was dissolved in 10 mL ethanol followed by addition of 1.2 mL of 1N NaOH. The mixture was stirred for 1 h. Ethanol was then evaporated under vacuum to obtain crude compound which was dissolved in water and the solution was neutralized using 1N HCl. Evaporation of the water followed by separation of salt by precipitation in ethanol yielded compound 8 (yield 82%) which was used without any purification for next step. NMR (500 MHz, $CD_3OD$) 2.50-3.21 (4H, N—$CH_2$—$CH_2$—CO, m), 4.18-4.44 (2H, NH—$CH_2$—CO, m), 7.14 (1H, ArH, t), 7.27 (1H, ArH, t) 7.43 (1H, ArH, d) 7.78 (1H, ArH, s); MS Anal. Mol. Wt. 299.07 (M+1).

Figure 17:
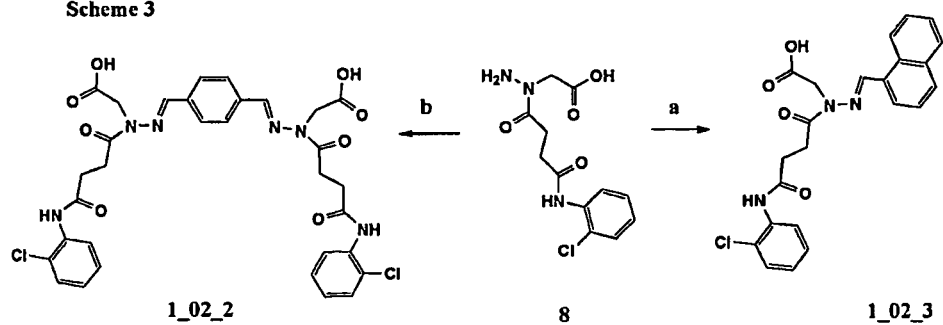

Synthesis of {N'-(4-{Carboxymethyl-[3-(2-chloro-phenylcarbamoyl)-propionyl]-hydrazonomethyl}-benzylidene)-N-[3-(2-chloro-phenylcarbamoyl)-propionyl]-hydrazino}-acetic acid (1_02_2, Scheme 3) (FIG. 17)

Benzene-1,4-dicarbaldehyde (0.006 g, 0.05 mmol) and compound 8 (0.032 g, 0.10 mmol) in ethanol (5 mL) were heated to reflux for 12 h. After cooling to room temperature, the precipitate was filtered off and washed with ethanol to give 1_02_2 as a pale white solid (0.015 g, yield 44%). $^1$H NMR (500 MHz, DMSO-d6) 2.72 (4H, N—$CH_2$—$CH_2$—CO, t), 3.15 (4H, N—$CH_2$—$CH_2$—CO, t), 4.52 (4H, NH—$CH_2$—CO, s), 7.15 (2H, ArH, t), 7.29 (2H, ArH, t), 7.47 (2H, ArH, d) 7.65-7.77 (6H, ArH, m); 9.56 (2H, Ar—CH=N); MS Anal. Mol. Wt. 696.15 (M–2).

Synthesis of {N-[3-(2-Chloro-phenylcarbamoyl)-propionyl]-N'-naphthalen-1-ylmethylene-hydrazino}-acetic acid (1_02_3, Scheme 3) (FIG. 17)

naphthalene-1-carbaldehyde (0.015 g, 0.10 mmol) and compound 8 (0.031 g, 0.10 mmol) in ethanol (5 mL) were heated to reflux for 12 h. After cooling to room temperature, the precipitate was filtered off and washed with ethanol to give 1_02_3 as a pale white solid (0.02 g, yield 47%). $^1$H NMR (500 MHz, DMSO-d6) 2.64 (1H, N—$CH_2$—$CH_2$—CO, t), 2.79 (1H, N—$CH_2$—$CH_2$—CO, t), 3.17 (1H, N—$CH_2$—$CH_2$—CO, t), 3.23 (1H, N—$CH_2$—$CH_2$—CO, t), 4.89-4.97 (2H, NH—$CH_2$—CO, m), 7.17 (1H, ArH, t), 7.31 (1H, ArH, t), 7.48 (1H, ArH, d) 7.56-7.68 (3H, ArH, m), 7.75 (1H, ArH, d), 7.96-8.04 (3H, ArH, m), 8.50 (1H, ArNH, s), 8.70 (1H, ArH, t), 9.56 (2H, Ar—CH=N); MS Anal. Mol. Wt. 437.11 (M–1).

Other compounds may be synthesized in a similar manner as Scheme 2 (FIG. 16) by replacing the chemical precursors, for example, replacing the 2-chloroanaline of Scheme 2 with an unsubstituted aniline group or an aniline group substituted with at least one group X selected from halogen, hydroxy and alkyl.

REFERENCES

All patents and publications mentioned in this specification are indicative of the level of those skilled in the art to which the invention pertains. All patents and publications herein are incorporated by reference to the same extent as if each individual publication was specifically and individually indicated as having been incorporated by reference in its entirety.

1. McDevitt, D., and Rosenberg, M. (2001). Exploiting genomics to discover new antibiotics. Trends Microbiol 9, 611-617.
2. Osterman, A. L., and Begley, T. P. (2007). A subsystems-based approach to the identification of drug targets in bacterial pathogens. Prog Drug Res 64, 131, 133-170.
3. Gerdes, S. Y., Scholle, M. D., D'Souza, M., Bernal, A., Baev, M. V., Farrell, M., Kurnasov, O. V., Daugherty, M. D., Mseeh, F., Polanuyer, B. M., Campbell, J. W., Anantha, S., Shatalin, K. Y., Chowdhury, S. A., Fonstein, M. Y., and Osterman, A. L. (2002). From genetic footprinting to antimicrobial drug targets: examples in cofactor biosynthetic pathways. J Bacteriol 184, 4555-4572.
4. Sassetti, C. M., Boyd, D. H., and Rubin, E. J. (2003). Genes required for mycobacterial growth defined by high density mutagenesis. Mol Microbiol 48, 77-84.
5. Chen, L., Petrelli, R., Felczak, K., Gao, G., Bonnac, L., Yu, J. S., Bennett, E. M., and Pankiewicz, K. W. (2008). Nicotinamide adenine dinucleotide based therapeutics. Curr Med Chem 15, 650-670.
6. Khan, J. A., Forouhar, F., Tao, X., and Tong, L. (2007). Nicotinamide adenine dinucleotide metabolism as an attractive target for drug discovery. Expert Opin Ther Targets 11, 695-705.
7. Lau, C., Niere, M., and Ziegler, M. (2009). The NMN/NaMN adenylyltransferase (NMNAT) protein family. Front Biosci 14, 410-431.
8. Magni, G., Di Stefano, M., Orsomando, G., Raffaelli, N., and Ruggieri, S. (2009). NAD(P) Biosynthesis Enzymes as Potential Targets for Selective Drug Design. Curr Med Chem 16, 1372-1390.
9. Sorci, L., Martynowski, D., Rodionov, D. A., Eyobo, Y., Zogaj, X., Klose, K. E., Nikolaev, E. V., Magni, G., Zhang, H., and Osterman, A. L. (2009). Nicotinamide mononucleotide synthetase is the key enzyme for an alternative route of NAD biosynthesis in *Francisella tularensis*. Proc Natl Acad Sci USA 106, 3083-3088.
10. Velu, S. E., Cristofoli, W. A., Garcia, G. J., Brouillette, C. G., Pierson, M. C., Luan, C. H., DeLucas, L. J., and Brouillette, W. J. (2003). Tethered dimers as NAD synthetase inhibitors with antibacterial activity. J Med Chem 46, 3371-3381.
11. Velu, S. E., Luan, C. H., Delucas, L. J., Brouillette, C. G., and Brouillette, W. J. (2005). Tethered dimer inhibitors of NAD synthetase: parallel synthesis of an aryl-substituted SAR library. J Comb Chem 7, 898-904.
12. Velu, S. E., Mou, L., Luan, C. H., Yang, Z. W., DeLucas, L. J., Brouillette, C. G., and Brouillette, W. J. (2007). Antibacterial nicotinamide adenine dinucleotide synthetase inhibitors: amide- and ether-linked tethered dimers with alpha-amino acid end groups. J Med Chem 50, 2612-2621.
13. Bonnac, L., Chen, L., Pathak, R., Gao, G., Ming, Q., Bennett, E., Felczak, K., Kullberg, M., Patterson, S. E., Mazzola, F., Magni, G., and Pankiewicz, K. W. (2007). Probing binding requirements of NAD kinase with modified substrate (NAD) analogues. Bioorg Med Chem Lett 17, 1512-1515.
14. Poncet-Montange, G., Assairi, L., Arold, S., Pochet, S., and Labesse, G. (2007). NAD kinases use substrate-assisted catalysis for specific recognition of NAD. J Biol Chem 282, 33925-33934.
15. Zhou, T., Kurnasov, O., Tomchick, D. R., Binns, D. D., Grishin, N. V., Marquez, V. E., Osterman, A. L., and Zhang, H. (2002). Structure of human nicotinamide/nicotinic acid mononucleotide adenylyltransferase. Basis for the dual substrate specificity and activation of the oncolytic agent tiazofurin. J Biol Chem 277, 13148-13154.
16. Gerdes, S., Edwards, R., Kubal, M., Fonstein, M., Stevens, R., and Osterman, A. (2006). Essential genes on metabolic maps. Curr Opin Biotechnol 17, 448-456.
17. Boshoff, H. I., Xu, X., Tahlan, K., Dowd, C. S., Pethe, K., Camacho, L. R., Park, T. H., Yun, C. S., Schnappinger, D., Ehrt, S., Williams, K. J., and Barry, C. E., 3rd (2008). Biosynthesis and recycling of nicotinamide cofactors in *mycobacterium tuberculosis*. An essential role for NAD in nonreplicating bacilli. J. Biol Chem 283, 19329-19341.
18. Gerlach, G., and Reidl, J. (2006). NAD+ utilization in Pasteurellaceae: simplification of a complex pathway. J Bacteriol 188, 6719-6727.
19. Zhang, H., Zhou, T., Kurnasov, O., Cheek, S., Grishin, N. V., and Osterman, A. (2002). Crystal structures of *E. coli* nicotinate mononucleotide adenylyltransferase and its complex with deamido-NAD. Structure 10, 69-79.
20. Yoon, H. J., Kim, H. L., Mikami, B., and Suh, S. W. (2005). Crystal structure of nicotinic acid mononucleotide adenylyltransferase from *Pseudomonas aeruginosa* in its Apo and substrate-complexed forms reveals a fully open conformation. J Mol Biol 351, 258-265.
21. Lu, S., Smith, C. D., Yang, Z., Pruett, P. S., Nagy, L., McCombs, D., Delucas, L. J., Brouillette, W. J., and Brouillette, C. G. (2008). Structure of nicotinic acid mononucleotide adenylyltransferase from *Bacillus anthracis*. Acta Crystallogr Sect F Struct Biol Cryst Commun 64, 893-898.
22. Olland, A. M., Underwood, K. W., Czerwinski, R. M., Lo, M. C., Aulabaugh, A., Bard, J., Stahl, M. L., Somers, W. S., Sullivan, F. X., and Chopra, R (2002). Identification, characterization, and crystal structure of *Bacillus subtilis* nicotinic acid mononucleotide adenylyltransferase. J Biol Chem 277, 3698-3707.
23. Han, S., Forman, M. D., Loulakis, P., Rosner, M. H., Xie, Z., Wang, H., Danley, D. E., Yuan, W., Schafer, J., and Xu, Z. (2006). Crystal structure of nicotinic acid mononucleotide adenylyltransferase from Staphyloccocus aureus: structural basis for NaAD interaction in functional dimer. J Mol Biol 360, 814-825.
24. Sershon, V. C., Santarsiero, B. D., and Mesecar, A. D. (2009). Kinetic and X-ray structural evidence for negative cooperativity in substrate binding to nicotinate mononucleotide adenylyltransferase (NMAT) from *Bacillus anthracis*. J Mol Biol 385, 867-888.
25. Sorci, L., Cimadamore, F., Scotti, S., Petrelli, R., Cappellacci, L., Franchetti, P., Orsomando, G., and Magni, G. (2007). Initial-rate kinetics of human NMN-adenylyltransferases: substrate and metal ion specificity, inhibition by products and multisubstrate analogues, and isozyme contributions to NAD+ biosynthesis. Biochemistry 46, 4912-4922.
26. Berger, F., Lau, C., Dahlmann, M., and Ziegler, M. (2005). Subcellular compartmentation and differential catalytic properties of the three human nicotinamide mononucleotide adenylyltransferase isoforms. J Biol Chem 280, 36334-36341.
27. Magni, G., Orsomando, G., Raffelli, N., and Ruggieri, S. (2008). Enzymology of mammalian NAD metabolism in health and disease. Front Biosci 13, 6135-6154.
28. Kurnasov, O. V., Polanuyer, B. M., Ananta, S., Sloutsky, R., Tam, A., Gerdes, S. Y., and Osterman, A. L. (2002). Ribosylnicotinamide Kinase Domain of NadR Protein: Identification and Implications in NAD Biosynthesis. J Bacteriol 184, 6906-6917.
29. Cogan, E. B., Birrell, G. B., and Griffith, O. H. (1999). A Robotics-Based Automated Assay for Inorganic and Organic Phosphates. Analytical Biochemistry 271, 29-35.
30. Butina, D. (1999). Unsupervised Data Base Clustering Based on Daylight's Fingerprint and Tanimoto Similarity: A Fast and Automated Way To Cluster Small and Large Data Sets. J. Chem. Inf. Comput. Sci. 39, 747-750.
31. Godden, J. W., Stahura, F. L., and Bajorath, J. (2005). Anatomy of fingerprint search calculations on structurally diverse sets of active compounds. J Chem Inf Model 45, 1812-1819.
32. Coan, K. E., and Shoichet, B. K. (2007). Stability and equilibria of promiscuous aggregates in high protein milieus. Mol Biosyst 3, 208-213.
33. Shoichet, B. K. (2006). Screening in a spirit haunted world. Drug Discov Today 11, 607-615.
34. Moro, W. B., Yang, Z., Kane, T. A., Brouillette, C. G., and Brouillette, W. J. (2009). Virtual screening to identify lead inhibitors for bacterial NAD synthetase (NADs). Bioorg Med Chem Lett 19, 2001-2005.
35. Garavaglia, S., D'Angelo, I., Emanuelli, M., Carnevali, F., Pierella, F., Magni, G., and Rizzi, M. (2002). Structure of human NMN adenylyltransferase. A key nuclear enzyme for NAD homeostasis. J Biol Chem 277, 8524-8530.
36. Zhang, X., Kurnasov, O. V., Karthikeyan, S., Grishin, N. V., Osterman, A. L., and Zhang, H. (2003). Structural characterization of a human cytosolic NMN/NaMN adenylyltransferase and implication in human NAD biosynthesis. J Biol Chem 278, 13503-13511.
37. Krumrine, J., Raubacher, F., Brooijmans, N., and Kuntz, I. (2003). Principles and methods of docking and ligand design. Methods Biochem Anal 44, 443-476.
38. Kuntz, I. D., Blaney, J. M., Oatley, S. J., Langridge, R., and Ferrin, T. E. (1982). A geometric approach to macromolecule-ligand interactions. J Mol Biol 161, 269-288.

39. Huang, N., Nagarsekar, A., Xia, G., Hayashi, J., and MacKerell, A. D., Jr. (2004). Identification of non-phosphate-containing small molecular weight inhibitors of the tyrosine kinase p56 Lck SH2 domain via in silico screening against the pY+3 binding site. J Med Chem 47, 3502-3511.
40. Zhong, S., Macias, A. T., and MacKerell, A. D., Jr. (2007). Computational identification of inhibitors of protein-protein interactions. Curr Top Med Chem 7, 63-82.
41. Ewing, T. J. A., and Kuntz, I. D. (1997). Critical evaluation of search algorithms for automated molecular docking and database screening. In Journal of Computational Chemistry, Volume 18. pp. 1175-1189.
42. Pan, Y., Huang, N., Cho, S., and MacKerell, A. D., Jr. (2003). Consideration of molecular weight during compound selection in virtual target-based database screening. J Chem Inf Comput Sci 43, 267-272.
43. Lyon, R. P., and Atkins, W. M. (2002). Kinetic characterization of native and cysteine 112-modified glutathione S-transferase A1-1: reassessment of nonsubstrate ligand binding. Biochemistry 41, 10920-10927.
44. Baba, T., Ara, T., Hasegawa, M., Takai, Y., Okumura, Y., Baba, M., Datsenko, K. A., Tomita, M., Wanner, B. L., and Mori, H. (2006). Construction of *Escherichia coli* K-12 in-frame, single-gene knockout mutants: the Keio collection. Mol Syst Biol 2, 2006 0008.
45. Kitagawa, M., Ara, T., Arifuzzaman, M., loka-Nakamichi, T., Inamoto, E., Toyonaga, H., and Mori, H. (2005). Complete set of ORF clones of *Escherichia coli* ASKA library (a complete set of *E. coli* K-12 ORF archive): unique resources for biological research. DNA Res 12, 291-299.
46. Firsov, A. A., Lubenko, I. Y., Portnoy, Y. A., Zinner, S. H., and Vostrov, S. N. (2001). Relationships of the area under the curve/MIC ratio to different integral endpoints of the antimicrobial effect: gemifloxacin pharmacodynamics in an in vitro dynamic model. Antimicrob Agents Chemother 45, 927-931.
47. Rodionov, D. A., Hebbeln, P., Eudes, A., ter Beek, J., Rodionova, I. A., Erkens, G. B., Slotboom, D. J., Gelfand, M. S., Osterman, A. L., Hanson, A. D., and Eitinger, T. (2009). A novel class of modular transporters for vitamins in prokaryotes. J Bacteriol 191, 42-51.
48. Otwinowski, Z., and Minor, W. (1997). [20] Processing of X-ray diffraction data collected in oscillation mode. In Methods in Enzymology, Volume 276. (Academic Press), pp. 307-326.
49. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998). Crystallography & NMR system: A new software suite for macromolecular structure determination. Acta Crystallogr D Biol Crystallogr 54, 905-921.
50. Vagin, A., and Teplyakov, A. (2000). An approach to multi-copy search in molecular replacement. Acta Crystallogr D Biol Crystallogr 56, 1622-1624.
51. Murshudov, G. N., Vagin, A. A., and Dodson, E. J. (1997). Refinement of macromolecular structures by the maximum-likelihood method. Acta Crystallogr D Biol Crystallogr 53, 240-255.
52. Collaborative Computational Project, N. (1994). The CCP4 suite: programs for protein crystallography. Acta Crystallogr D Biol Crystallogr 50, 760-763.
53. Lovell, S. C., Davis, I. W., Arendall, W. B., 3rd, de Bakker, P. I., Word, J. M., Prisant, M. G., Richardson, J. S., and Richardson, D. C. (2003). Structure validation by Calpha geometry: phi,psi and Cbeta deviation. Proteins 50, 437-450.

S1. Zhang, H., Zhou, T., Kurnasov, O., Cheek, S., Grishin, N. V., and Osterman, A. (2002). Crystal structures of *E. coli* nicotinate mononucleotide adenylyltransferase and its complex with deamido-NAD. Structure 10, 69-79.
S2. Brooks, B. R., Bruccoler, R. E., Olafson, B. D., States, D. J., Swaminathan, S., and Karplus, M. (1983). CHARMM: A program for macromolecular energy, minimization, and dynamics calculations. Journal of Computational Chemistry 4, 187-217.
S3. MacKerell, A. D., Jr., B. Brooks, C. L. Brooks, III, L. Nilsson, B. Roux, Y. Won, and M. Karplus. (1998). CHARMM: The Energy Function and its Parameterization with an Overview of the Program. In Encyclopedia of Computational Chemistry. (P.v.R. Schleyer, N. L. Allinger, J. Clark, P. A. Gasteiger, H. F. Kollman, I. Schaefer and P. R. Schreiner, eds.). pp. 271-277, John Wiley & Sons: Chichester.
S4. Jorgensen, W. L., Chandrasekhar, J., Madura, J. D., Impey, R. W., and Klein, M. L. (1983). Comparison of simple potential functions for simulating liquid water. The Journal of Chemical Physics 79, 926-935.
S5. Feller, S. E., Zhang, Y., Pastor, R. W., and Brooks, B. R. (1995). Constant pressure molecular dynamics simulation: The Langevin piston method. The Journal of Chemical Physics 103, 4613-4621.
S6. Ryckaert, J.-P., Ciccotti, G., and Berendsen, H. J. C. (1977). Numerical integration of the cartesian equations of motion of a system with constraints: molecular dynamics of n-alkanes. Journal of Computational Physics 23, 327-341.
S7. Kelley, L. A., Gardner, S. P., and Sutcliffe, M. J. (1996). An automated approach for clustering an ensemble of NMR-derived protein structures into conformationally related subfamilies. Protein Eng 9, 1063-1065.
S8. Butina, D. (1999). Unsupervised Data Base Clustering Based on Daylight's Fingerprint and Tanimoto Similarity: A Fast and Automated Way To Cluster Small and Large Data Sets. J. Chem. Inf. Comput. Sci. 39, 747-750.
S9. Godden, J. W., Stahura, F. L., and Bajorath, J. (2005). Anatomy of fingerprint search calculations on structurally diverse sets of active compounds. J Chem Inf Model 45, 1812-1819.
S10. Furci, L. M., Lopes, P., Eakanunkul, S., Zhong, S., MacKerell, A. D., Jr., and Wilks, A. (2007). Inhibition of the bacterial heme oxygenases from *Pseudomonas aeruginosa* and *Neisseria meningitidis*: novel antimicrobial targets. J Med Chem 50, 3804-3813.
S11. Lipinski, C. A. (2000). Drug-like properties and the causes of poor solubility and poor permeability. J Pharmacol Toxicol Methods 44, 235-249.
S12. Oprea, T. I., Davis, A. M., Teague, S. J., and Leeson, P. D. (2001). Is there a difference between leads and drugs? A historical perspective. J Chem Inf Comput Sci 41, 1308-1315.
A14. Sorci, L.; Pan, Y.; Eyobo, Y.; Rodionova, I.; Huang, N.; Kurnasov, O.; Zhong, S.; MacKerell, A. D., Jr.; Zhang, H.; Osterman, A. L., Targeting NAD biosynthesis in bacterial pathogens: Structure-based development of inhibitors of nicotinate mononucleotide adenylyltransferase NadD. Chem Biol 2009, 16, 849-861.
A15. Begley, T. P.; Kinsland, C.; Mehl, R. A.; Osterman, A.; Dorrestein, P., The biosynthesis of nicotinamide adenine dinucleotides in bacteria. *Vitam. Horm.* 2001, 61, 103-119.
A16. Mehl, R. A.; Kinsland, C.; Begley, T. P., Identification of the *Escherichia coli* nicotinic acid mononucleotide adenylyltransferase gene. *J Bacteriol* 2000, 182, 4372-4374.
A17. Zhang, H.; Zhou, T.; Kurnasov, O.; Cheek, S.; Grishin, N. V.; Osterman, A., Crystal structures of *E. coli* nicotinate mononucleotide adenylyltransferase and its complex with deamido-NAD. *Structure* 2002, 10, 69-79.

A18. Olland, A. M.; Underwood, K. W.; Czerwinski, R. M.; Lo, M. C.; Aulabaugh, A.; Bard, J.; Stahl, M. L.; Somers, W. S.; Sullivan, F. X.; Chopra, R., Identification, characterization, and crystal structure of *Bacillus subtilis* nicotinic acid mononucleotide adenylyltransferase. *J Biol Chem* 2002, 277, 3698-3707.

A19. Yoon, H. J.; Kim, H. L.; Mikami, B.; Suh, S. W., Crystal structure of nicotinic acid mononucleotide adenylyltransferase from *Pseudomonas aeruginosa* in its Apo and substrate-complexed forms reveals a fully open conformation. *J Mol Biol* 2005, 351, 258-265.

A20. Han, S.; Forman, M. D.; Loulakis, P.; Rosner, M. H.; Xie, Z.; Wang, H.; Danley, D. E.; Yuan, W.; Schafer, J.; Xu, Z., Crystal structure of nicotinic acid mononucleotide adenylyltransferase from *Staphyloccocus aureus*: structural basis for NaAD interaction in functional dimer. *J Mol Biol* 2006, 360, 814-825.

A21. Lu, S.; Smith, C. D.; Yang, Z.; Pruett, P. S.; Nagy, L.; McCombs, D.; Delucas, L. J.; Brouillette, W. J.; Brouillette, C. G., Structure of nicotinic acid mononucleotide adenylyltransferase from *Bacillus anthracis*. *Acta Crystallogr Sect F Struct Biol Cryst Commun* 2008, 64, 893-898.

A22. Sershon, V. C.; Santarsiero, B. D.; Mesecar, A. D., Kinetic and X-ray structural evidence for negative cooperativity in substrate binding to nicotinate mononucleotide adenylyltransferase (NMAT) from *Bacillus anthracis*. *J Mol Biol* 2009, 385, 867-888.

A27. Ryll, T.; Wagner, R., Improved ion-pair high-performance liquid chromatographic method for the quantification of a wide variety of nucleotides and sugar-nucleotides in animal cells. *J Chromatogr* 1991, 570, 77-88.

A28. Tong, L.; Lee, S.; Denu, J. M., Hydrolase regulates NAD+ metabolites and modulates cellular redox. *J Biol Chem* 2009, 284, 11256-11266.

A29. Huang, N.; De Ingeniis, J.; Galeazzi, L.; Mancini, C.; Korostelev, Y. D.; Rakhmaminova, A. B.; Gelfand, M. S.; Rodionov, D. A.; Raffaelli, N.; Zhang, H., Structure and function of an ADP-ribose-dependent transcriptional regulator of NAD metabolism. *Structure* 2009, 17, 939-951.

A30. Minor, W.; Cymborowski, M.; Otwinowski, Z.; Chruszcz, M., HKL-3000: the integration of data reduction and structure solution—from diffraction images to an initial model in minutes. *Acta Crystallogr D Biol Crystallogr* 2006, 62, 859-866.

A31. Murshudov, G. N.; Vagin, A. A.; Dodson, E. J., Refinement of macromolecular structures by the maximum-likelihood method. *Acta Crystallogr. D Biol. Crystallogr.* 1997, 53, 240-255.

A32. Collaborative Computational Project Number 4. The CCP4 Suite: programs for protein crystallography. *Acta Crystallogr. D Biol. Crystallogr.* 1994, 50, 760-763.

A33. Potterton, E.; Briggs, P.; Turkenburg, M.; Dodson, E., A graphical user interface to the CCP4 program suite. *Acta Crystallogr D Biol Crystallogr* 2003, 59, 1131-1137.

A34. McCoy, A. J.; Grosse-Kunstleve, R. W.; Adams, P. D.; Winn, M. D.; Storoni, L. C.; Read, R. J., Phaser crystallographic software. *J. Appl. Cryst.* 2007, 40, 658-674.

A35. Emsley, P.; Cowtan, K., Coot: model-building tools for molecular graphics. *Acta Crystallogr. D Biol. Crystallogr.* 2004, 60, 2126-2132.

A36. Schuttelkopf, A. W.; van Aalten, D. M., PRODRG: a tool for high-throughput crystallography of protein-ligand complexes. *Acta Crystallogr D Biol Crystallogr* 2004, 60, 1355-1363.

A37. Adams, P. D.; Gopal, K.; Grosse-Kunstleve, R. W.; Hung, L. W.; Ioerger, T. R.; McCoy, A. J.; Moriarty, N. W.; Pai, R. K.; Read, R. J.; Romo, T. D.; Sacchettini, J. C.; Sauter, N. K.; Storoni, L. C.; Terwilliger, T. C., Recent developments in the PHENIX software for automated crystallographic structure determination. *J. Synchrotron. Radial.* 2004, 11, 53-55.

A38. Adams, P. D.; Grosse-Kunstleve, R. W.; Hung, L. W.; Ioerger, T. R.; McCoy, A. J.; Moriarty, N. W.; Read, R J.; Sacchettini, J. C.; Sauter, N. K.; Terwilliger, T. C., PHENIX: building new software for automated crystallographic structure determination. *Acta Crystallogr. D Biol. Crystallogr.* 2002, 58, 1948-1954.

A39. Davis, I. W.; Leaver-Fay, A.; Chen, V. B.; Block, J. N.; Kapral, G. J.; Wang, X.; Murray, L. W.; Arendall, W. B., 3rd; Snoeyink, J.; Richardson, J. S.; Richardson, D. C., MolProbity: all-atom contacts and structure validation for proteins and nucleic acids. *Nucleic Acids Res* 2007, 35, (Web Server issue), W375-383.

A40. Berman, H. M.; Westbrook, J.; Feng, Z.; Gilliland, G.; Bhat, T. N.; Weissig, H.; Shindyalov, I. N.; Bourne, P. E., The Protein Data Bank. *Nucleic Acids Res* 2000, 28, 235-242.

A41. Cogan, E. B.; Birrell, G. B.; Griffith, O. H., A Robotics-Based Automated Assay for Inorganic and Organic Phosphates. *Analytical Biochemistry* 1999, 271, 29-35.

Tables

TABLE 1

Inhibitor:

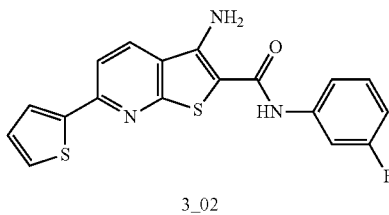

3_02

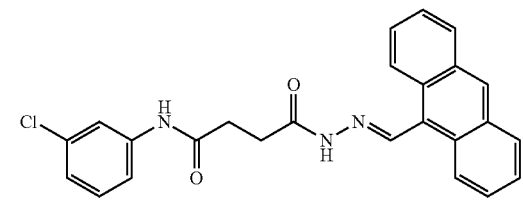 [SMILES: O=C(CCC(=O)Nc1cccc(Cl)c1)N/N=C/c1c2ccccc2cc2ccccc12]

1_02

| Substrate: | NaMN | | ATP | | NaMN | | ATP | |
|---|---|---|---|---|---|---|---|---|
| | $K_i$ (μM) | α | $K_i$ (μM) | α | $K_i$ (μM) | α | $K_i$ (μM) | α |
| baNadD | 18 ± 4 | 2.4 | 32 ± 5 | 5.5 | 9 ± 3 | 2.3 | 10 ± 2 | 2.9 |
| ecNadD | 25 ± 9 | 2.5 | 21 ± 9 | 2.4 | 8 ± 3 | 7.2 | 5 ± 1 | 7.1 |

TABLE 2

| Entry | Compound structure | IC$_{50}$$^a$, (μM) ecNadD | IC$_{50}$$^a$, (μM) baNadD$^c$ | MIC$_{50}$$^b$ (μM) E. coli | MIC$_{50}$$^b$ (μM) B. anth | MIC$_{50}$$^b$ (μM) B. subt |
|---|---|---|---|---|---|---|
| 3_05 | | 20 | 9 | 80 | 10 | 10 |
| 3_15 | | 51 | 12 | 160 | 10 | 10 |
| 3_02 | | 65 | 36 | 160 | 80 | 40 |
| 3_17 | | 170 | >200 | 80 | >160 | >160 |
| 1_03 | | 18 | 33 | >80 | 15$^d$ | 10 |
| 1_02 | | 15 | 25 | >80 | n.d. | n.d. |
| 3_23 | | >200 | 63 | 40 | 80 | 80 |

TABLE 2-continued

| Entry | Compound structure | IC$_{50}$$^a$ (μM) ecNadD | IC$_{50}$$^a$ (μM) baNadD$^c$ | MIC$_{50}$$^b$ (μM) E. coli | MIC$_{50}$$^b$ (μM) B. anth | MIC$_{50}$$^b$ (μM) B. subt |
|---|---|---|---|---|---|---|
| 15_11 | (structure) | 191 | 98 | <100$^c$ | NA | <50$^c$ |

TABLE 3

| protein | Complex state | PDB ID | residues-in-site |
|---|---|---|---|
| ecNadD | apo | 1k4k | GLY10, ASP109, SER180 |
|  | NaAD bound | 1k4m | HIS19, ARG46, ARG134 |
| hsNMNAT-1 | apo | 1kku | TYR55, ASP158, TRP169 |
|  | NAD bound | 1kqn | LYS57, ASP158, SER222 |
|  | NaAD bound | 1kqo | LYS57, ASP158, SER222 |
|  | TAD bound | 1kr2 | LYS57, ASP158, SER222 |
| baNadD | apo | 2qtm | ASN39, MET109, SER156 |
|  | NaMN bound | 2qtn | ASN39, MET109, SER156 |
|  | NaAD bound | 2qtr | LYS45, ASP108, SER156 |
|  | apo | 3dv2 | ILE21, ASN39, MET109 |
|  | NaAD bound | 3e27 | LYS45, ASP108, SER156 |

TABLE 4

| ID | E. Coli | B. anthracis | Human |
|---|---|---|---|
| 1_02 | −50.4 | −44.2 | −45.4 |
| 1_03 | −45.6 | −46.6 | −44.1 |
| 1_05 | −47.7 | −50.4 | −44.3 |
| 1_11 | −48.0 | −42.1 | −39.5 |
| 1_13 | −42.2 | −58.3 | −40.6 |
| 1_15 | −46.3 | −51.8 | −39.3 |
| 15_11 | −46.6 | −45.6 | −32.8 |
| 15_27 | −39.9 | −40.4 | −33.5 |
| 3_02 | −37.2 | −45.8 | −31.9 |
| 3_05 | −32.2 | −30.8 | −36.4 |
| 3_15 | −40.2 | −41.2 | −31.7 |
| 3_17 | −33.8 | −31.9 | −33.7 |
| 3_21 | −43.2 | −41.7 | −35.5 |
| 3_23 | −42.8 | −48.1 | −33.0 |
| 3_C11 | −39.5 | −44.2 | −37.1 |

TABLE 5

Interaction (E)

| ID | Electrostatic E. coli | Electrostatic B. anthracis | Electrostatic Human | Van der Waals E. coli | Van der Waals B. anthracis | Van der Waals Human |
|---|---|---|---|---|---|---|
| 1_02 | −11.6 | −17.9 | −16.8 | −47.6 | −42.9 | −39.6 |
| 1_03 | −15.3 | −16.7 | −14.1 | −38.3 | −41.9 | −39.3 |
| 1_05 | −14.5 | −19.5 | −17.2 | −41.3 | −45.1 | −38.1 |
| 1_11 | 1.4 | −2.0 | −2.5 | −45.3 | −40.0 | −37.6 |
| 1_13 | −14.1 | −13.0 | −13.0 | −36.0 | −53.5 | −35.8 |
| 1_15 | −11.9 | −13.2 | −15.1 | −41.2 | −46.8 | −31.9 |
| 15_11 | −10.0 | −12.1 | −11.4 | −40.5 | −40.2 | −28.0 |
| 15_27 | −11.2 | −11.8 | −11.3 | −35.8 | −37.3 | −28.4 |
| 3_02 | −16.6 | −22.0 | −17.0 | −39.0 | −43.2 | −29.7 |
| 3_05 | −18.4 | −19.0 | −19.9 | −28.6 | −30.2 | −32.8 |
| 3_15 | −19.0 | −16.8 | −20.1 | −40.3 | −40.4 | −27.1 |
| 3_17 | −17.2 | −15.2 | −16.3 | −36.5 | −35.9 | −29.8 |
| 3_21 | −16.5 | −18.8 | −16.2 | −37.0 | −37.2 | −31.2 |
| 3_23 | −14.8 | −18.6 | −20.0 | −42.6 | −48.1 | −29.2 |
| 3_C11 | −17.0 | −19.1 | −17.4 | −40.8 | −45.4 | −32.9 |

TABLE 6

Attractive vdW interaction energy

| ID | E. coli | B. anthracis | Human |
|---|---|---|---|
| 1_02 | −80.4 | −71.6 | −58.2 |
| 1_03 | −60.5 | −84.1 | −57.4 |
| 1_05 | −68.9 | −104.7 | −63.8 |
| 1_11 | −88.4 | −71.9 | −61.7 |
| 1_13 | −58.0 | −85.5 | −52.4 |
| 1_15 | −65.1 | −83.0 | −49.4 |
| 15_11 | −63.1 | −63.3 | −47.8 |
| 15_27 | −60.4 | −61.0 | −46.3 |
| 3_02 | −64.3 | −71.7 | −54.8 |
| 3_05 | −39.5 | −51.7 | −48.8 |
| 3_15 | −70.8 | −80.8 | −42.7 |
| 3_17 | −71.8 | −83.5 | −51.0 |
| 3_21 | −61.7 | −75.5 | −48.1 |
| 3_23 | −76.2 | −81.6 | −43.3 |
| 3_C11 | −80.9 | −89.8 | −49.9 |

TABLE 7

| Data sets | baNadD•product | baNadD•3_02 |
|---|---|---|
| Data Statistics |  |  |
| Space group | P2$_1$2$_1$2$_1$ | P2$_1$2$_1$2 |
| Unit cell (Å) | a = 41.8, b = 137.41, c = 143.97 | a = 88.79, b = 97.53, c = 44.30 |
| Resolution (Å) | 50-2.2 | 50-2.0 |
| Total observations | 157926 | 113171 |
| Unique Reflections | 43353 | 26467 |
| Completeness (outer shell) (%) | 98.8 (89.9) | 99.9 (100.0) |
| R$_{sym}$ (outer shell) | 0.085 (0.555) | 0.037 (0.279) |
| I/δ (outer shell) | 15.9 (2.0) | 36.8 (5.4) |
| Refinement |  |  |
| R$_{work}$$^b$ | 0.206 | 0.205 |
| R$_{free}$$^c$ | 0.276 | 0.266 |
| r.m.s.d bond length (Å) | 0.011 | 0.012 |

TABLE 7-continued

| Data sets | baNadD•product | baNadD•3_02 |
|---|---|---|
| r.m.s.d bond angle (°) | 1.49 | 1.44 |
| Protein atoms | 6196 | 3102 |
| Water molecules | 494 | 309 |
| Ligand atoms | 180 | 53 |
| Average B-factors (Å2) | | |
| Protein | 32.4 | 28.0 |
| ligands | 24.4 | 41.1 |
| water | 39.9 | 34.4 |
| Ramachandran Plot | | |
| Favored region (%) | 97.0 | 98.7 |
| Allowed region (%) | 99.3 | 100.0 |

TABLE 8

| # | VENDOR | ID | STRUCTURE | INHIBITION E. coli | INHIBITION B. anthracis |
|---|---|---|---|---|---|
| 001 | SPECSNET | AG-205/ 32429038 (X10) | 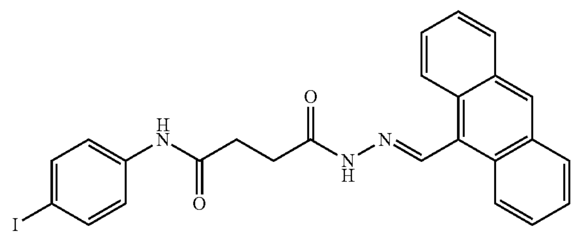 [SMILES: O=C(CCC(=O)Nc1ccc(I)cc1)N/N=C/c1c2ccccc2cc2ccccc12] | 79% | 88% |
| 002 | MAYBRIDGE | RDR00325 | 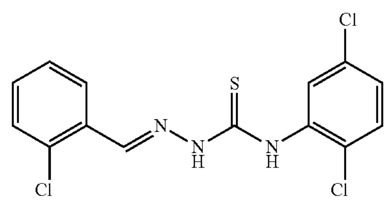 [SMILES: S=C(N/N=C/c1ccccc1Cl)Nc1cc(Cl)ccc1Cl] | 76% | 85% |
| 003 | SPECSNET; | AM-807/ 13614404 (C11) | 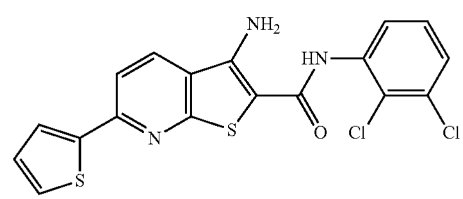 [SMILES: Nc1c(C(=O)Nc2cccc(Cl)c2Cl)sc2nc(-c3cccs3)ccc12] | 73% | 40% |
| 004 | CHEMDIV | 8004-8936 | 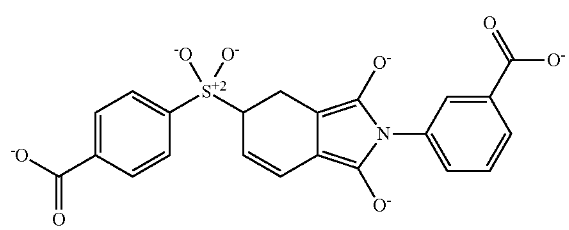 | 71% | 44% |
| 005 | MAYBRIDGE | SEW02074 | 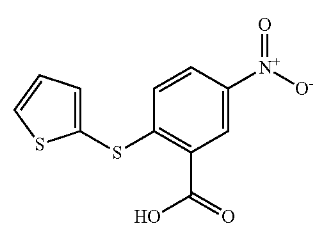 [SMILES: O=C(O)c1cc([N+](=O)[O-])ccc1Sc1cccs1] | 71% | 44% |
| 006 | SPECSNET | AN-829/ 13539519 | 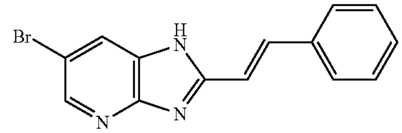 [SMILES: Brc1cnc2nc(/C=C/c3ccccc3)[nH]c2c1] | 62% | 34% |

TABLE 8-continued
| # | VENDOR | ID | STRUCTURE | INHIBITION | |
|---|---|---|---|---|---|
| | | | | E. coli | B. anthracis |
| 007 | CHEMBRIDGE | 6766541 | 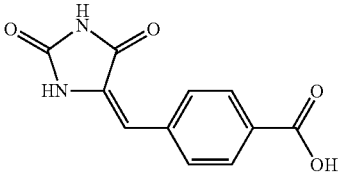 [SMILES: O=C1NC(=O)/C(=C\c2ccc(C(=O)O)cc2)N1] | 54% | 34% |
| 008 | SPECSNET | AG-690/ 11635622 | 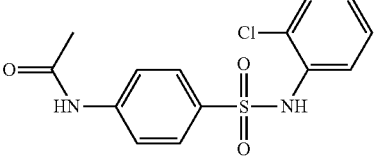 | 47% | 0% |
| 009 | SPECSNET | AK-968/ 15608936 | 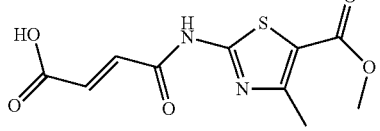 | 45% | 0% |
| 010 | CHEMDIV | 5186-0398 | 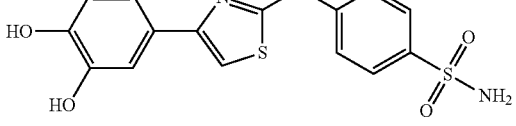 | 32% | 89% |
| 011 | CHEMBRIDGE | 5537105 | 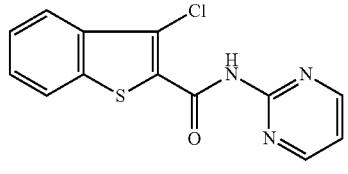 [SMILES: O=C(Nc1ncccn1)c1sc2ccccc2c1Cl] | 31% | 0% |
| 012 | SPECSNET | AG-690/ 36106009 | 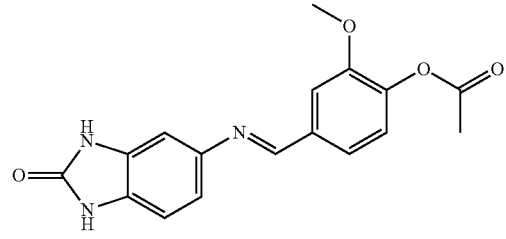 [SMILES: COc1cc(/C=N/c2ccc3[nH]c(=O)[nH]c3c2)ccc1OC(C)=O] | 30% | 0% |
| 013 | SPECSNET | AE-484/ 32881023 | 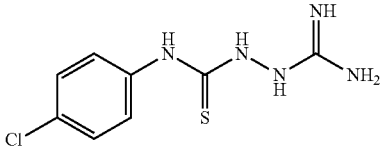 [SMILES: N=C(N)NNC(=S)Nc1ccc(Cl)cc1] | 30% | 0% |
| 014 | SPECSNET | AN-023/ 12769011 | 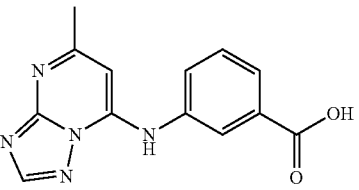 [SMILES: Cc1cc(Nc2cccc(C(=O)O)c2)n2ncnc2n1] | 30% | 0% |

TABLE 8-continued

| # | VENDOR | ID | STRUCTURE | INHIBITION | |
|---|---|---|---|---|---|
| | | | | E. coli | B. anthracis |
| 015 | CHEMDIV | C285-0040 (12B) | 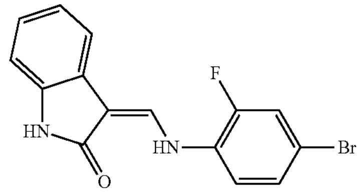 [SMILES: O=C1Nc2ccccc2/C1=C/Nc1ccc(Br)cc1F] | 29% | 57% |
| 016 | NANOSYN | NS2925 | 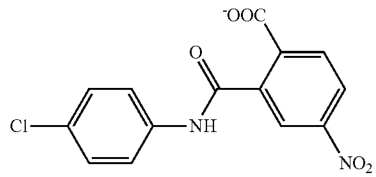 | 29% | 75% |
| 017 | CHEMBRIDGE | 5528186 | 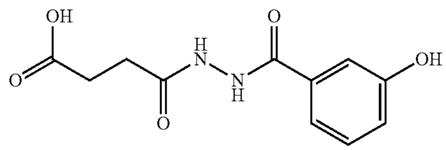 [SMILES: O=C(O)CCC(=O)NNC(=O)c1cccc(O)c1] | 27% | 0% |
| 018 | SPECSNET | AK-918/ 14550057 | 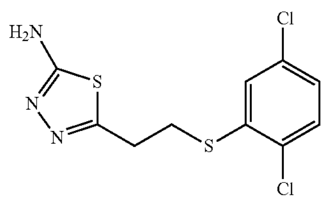 [SMILES: Nc1nnc(CCSc2cc(Cl)ccc2Cl)s1] | 27% | 0% |
| 019 | MAYBRIDGE | CD05223 | 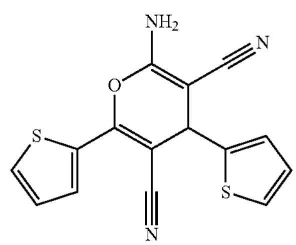 [SMILES: N#CC1=C(N)OC(c2cccs2)=C(C#N)C1c1cccs1] | 26% | 27% |
| 020 | SPECSNET | AK-918/ 11592005 | 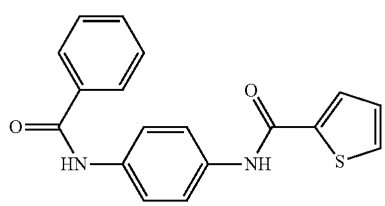 [SMILES: O=C(Nc1ccc(NC(=O)c2cccs2)cc1)c1ccccc1] | 26% | 0% |
| 021 | CHEMBRIDGE | 5707857 | 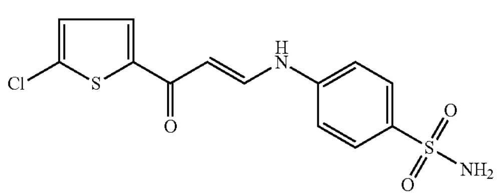 [SMILES: NS(=O)(=O)c1ccc(N/C=C/C(=O)c2ccc(Cl)s2)cc1] | 24% | 79% |
| 022 | CHEMBRIDGE | 5652726 | 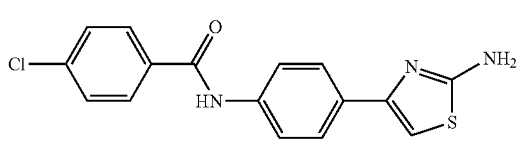 [SMILES: Nc1nc(-c2ccc(NC(=O)c3ccc(Cl)cc3)cc2)cs1] | 24% | 31% |

TABLE 8-continued

| # | VENDOR | ID | STRUCTURE | INHIBITION | |
|---|---|---|---|---|---|
| | | | | E. coli | B. anthracis |
| 023 | SPECSNET | AG-205/ 13109249 | 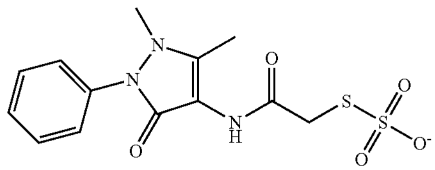 [SMILES: Cc1c(NC(=O)CSS(=O)(=O)[O-])c(=O)n(-c2ccccc2)n1C] | 24% | 34% |
| 024 | CHEMBRIDGE | 5238675 | 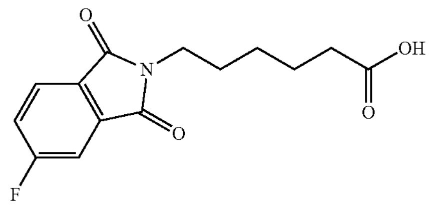 [SMILES: O=C(O)CCCCCN1C(=O)c2ccc(F)cc2C1=O] | 23% | 0% |
| 025 | MAYBRIDGE | 312870 | 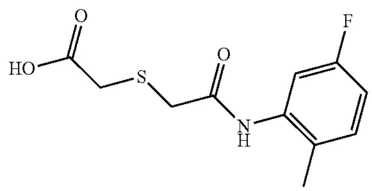 [SMILES: Cc1ccc(F)cc1NC(=O)CSCC(=O)O] | 23% | 55% |
| 026 | CHEMBRIDGE | 6874722 | 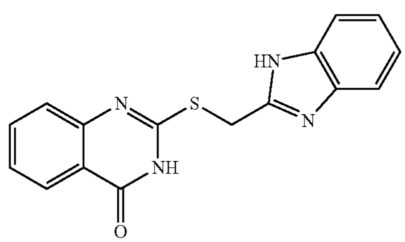 [SMILES: O=c1[nH]c(SCc2nc3ccccc3[nH]2)nc2ccccc12] | 23% | 0% |
| 027 | SPECSNET | AG-690/ 36281062 | 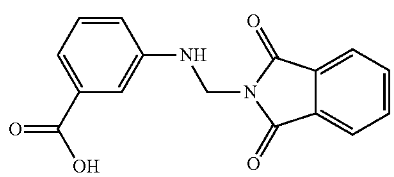 [SMILES: O=C(O)c1cccc(NCN2C(=O)c3ccccc3C2=O)c1] | 23% | 0% |
| 028 | CHEMBRIDGE | 5798694 | 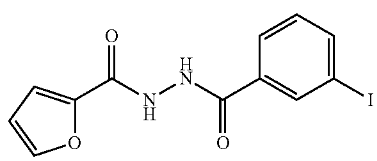 [SMILES: O=C(NNC(=O)c1ccco1)c1cccc(I)c1] | 23% | 7% |
| 029 | SPECSNET | AN-919/ 15527107 | 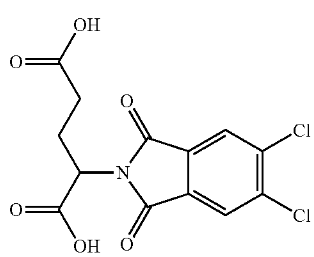 [SMILES: O=C(O)CCC(C(=O)O)N1C(=O)c2cc(Cl)c(Cl)cc2C1=O] | 22% | 0% |

TABLE 8-continued

| # | VENDOR | ID | STRUCTURE | INHIBITION | |
|---|--------|-----|-----------|------------|---|
|   |        |     |           | E. coli | B. anthracis |
| 030 | CHEMBRIDGE | 5654059 (C3) | 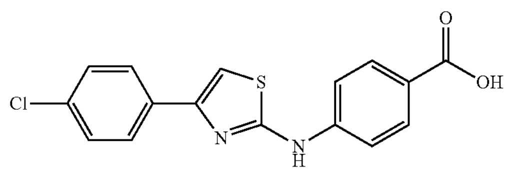 [SMILES: O=C(O)c1ccc(Nc2nc(-c3ccc(Cl)cc3)cs2)cc1] | 22% | 28% |
| 031 | CHEMDIV | C612-0726 | 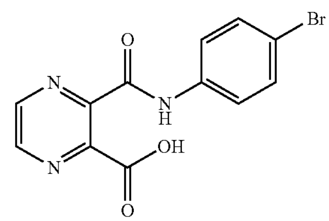 [SMILES: O=C(O)c1nccnc1C(=O)Nc1ccc(Br)cc1] | 21% | 4% |
| 032 | SPECSNET | AN-465/ 42768143 | 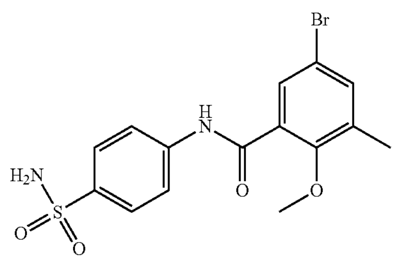 [SMILES: COc1c(C)cc(Br)cc1C(=O)Nc1ccc(S(N)(=O)=O)cc1] | 21% | 8% |
| 033 | CHEMBRIDGE | 5232616 | 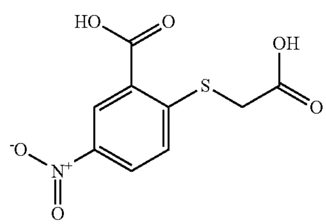 | 21% | 0% |
| 034 | CHEMDIV | 2023-0056 | 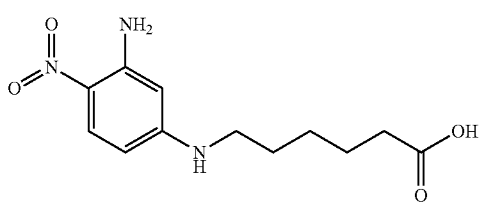 [SMILES: Nc1cc(NCCCCCC(=O)O)ccc1[N+](=O)[O-]] | 21% | 1% |
| 035 | CHEMBRIDGE | 7916939 | 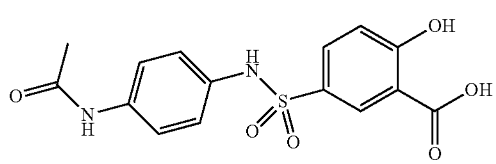 [SMILES: CC(=O)Nc1ccc(NS(=O)(=O)c2ccc(O)c(C(=O)O)c2)cc1] | 20% | 0% |
| 036 | SPECSNET | AN-652/ 41376266 | 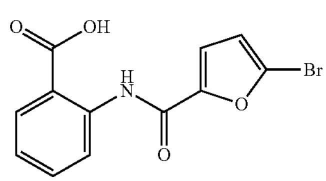 [SMILES: O=C(Nc1ccccc1C(=O)O)c1ccc(Br)o1] | 20% | 0% |

TABLE 8-continued

| # | VENDOR | ID | STRUCTURE | INHIBITION | |
|---|---|---|---|---|---|
| | | | | E. coli | B. anthracis |
| 037 | CHEMBRIDGE | 5376889 | 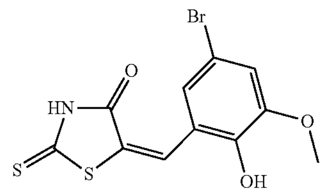 [SMILES: COc1cc(Br)cc(/C=C2/SC(=S)NC2=O)c1O] | 20% | 0% |
| 038 | CHEMBRIDGE | 5357363 | 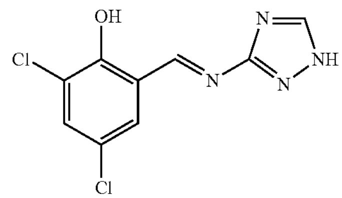 [SMILES: Oc1c(Cl)cc(Cl)cc1/C=N/c1nc[nH]n1] | 20% | 0% |
| 039 | SPECSNET | AF-399/ 15030248 | 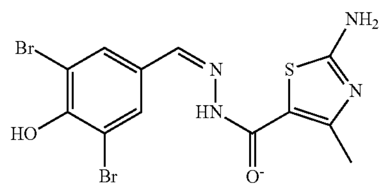 | 20% | 0% |
| 040 | CHEMBRIDGE | 5380358 | 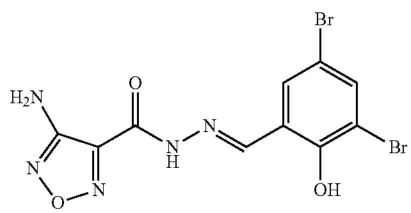 [SMILES: Nc1nonc1C(=O)N/N=C/c1cc(Br)cc(Br)c1O] | 19% | 20% |
| 041 | SPECSNET | AG-690/ 33347062 | 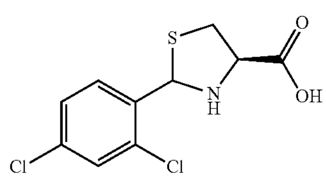 [SMILES: O=C(O)[C@@H]1CSC(c2ccc(Cl)cc2Cl)N1] | 19% | 39% |
| 042 | CHEMDIV | 8013-2042 | 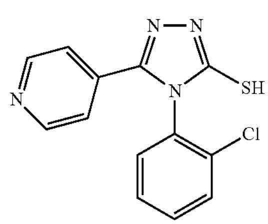 [SMILES: Sc1nnc(-c2ccncc2)n1-c1ccccc1Cl] | 19% | n.d. |
| 043 | CHEMBRIDGE | 5231111 | 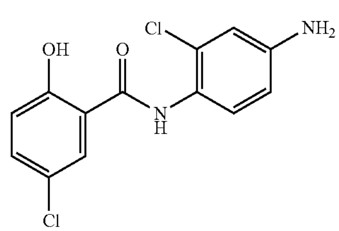 [SMILES: Nc1ccc(NC(=O)c2cc(Cl)ccc2O)c(Cl)c1] | 18% | 2% |

TABLE 8-continued
| # | VENDOR | ID | STRUCTURE | INHIBITION | |
|---|---|---|---|---|---|
| | | | | E. coli | B. anthracis |
| 044 | CHEMBRIDGE | 5349303 | 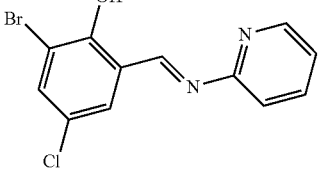 | 17% | 0% |
| 045 | CHEMBRIDGE | 6862662 | 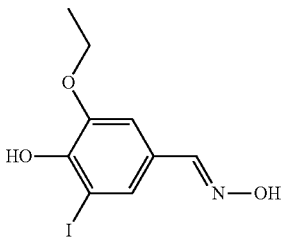 | 17% | 0% |
| 046 | CHEMBRIDGE | 6431895 | 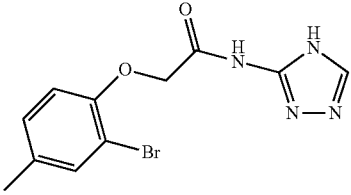 [SMILES: Cc1ccc(OCC(=O)Nc2nnc[nH]2)c(Br)c1] | 17% | 71% |
| 047 | SPECSNET | AM-807 43276008 | 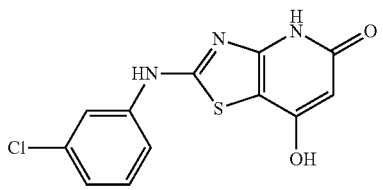 [SMILES: O=c1cc(O)c2sc(Nc3cccc(Cl)c3)nc2[nH]1] | 17% | 0% |
| 048 | CHEMBRIDGE | 6604853 | 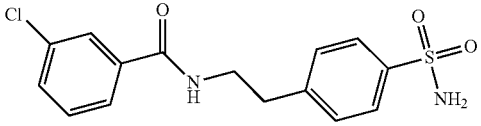 [SMILES: NS(=O)(=O)c1ccc(CCNC(=O)c2cccc(Cl)c2)cc1] | 16% | 14% |
| 049 | CHEMBRIDGE | 6604802 | 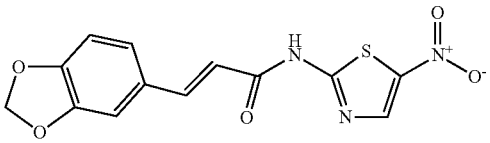 [SMILES: O=C(/C=C/c1ccc2c(c1)OCO2)Nc1ncc([N+](=O)[O-])s1] | 16% | 10% |
| 050 | SPECSNET | AF-399/ 15337214 | 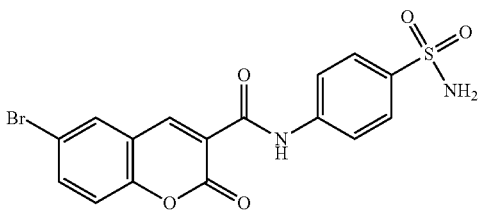 [SMILES: NS(=O)(=O)c1ccc(NC(=O)c2cc3cc(Br)ccc3oc2=O)cc1] | 16% | 38% |
| 051 | CHEMBRIDGE | 5604747 | 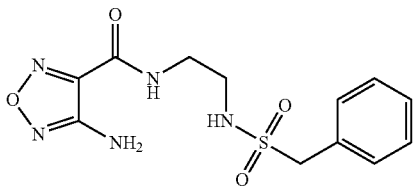 [SMILES: Nc1nonc1C(=O)NCCNS(=O)(=O)Cc1ccccc1] | 16% | 0% |

TABLE 8-continued

| # | VENDOR | ID | STRUCTURE | INHIBITION | |
|---|---|---|---|---|---|
| | | | | E. coli | B. anthracis |
| 052 | SPECSNET | AI-204/ 42879139 | 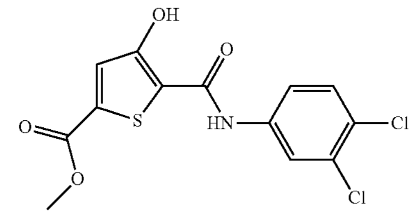 [SMILES: COC(=O)c1cc(O)c(C(=O)Nc2ccc(Cl)c(Cl)c2)s1] | 16% | 24% |
| 053 | SPECSNET | AJ-292/ 42284839 | 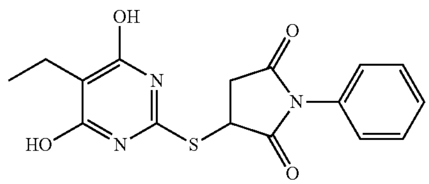 [SMILES: CCc1c(O)nc(SC2CC(=O)N(c3ccccc3)C2=O)nc1O] | 16% | 0% |
| 054 | CHEMBRIDGE | 7921220 | 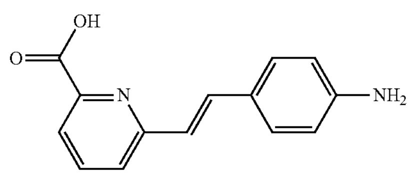 [SMILES: Nc1ccc(/C=C/c2cccc(C(=O)O)n2)cc1] | 15% | 27% |
| 055 | CHEMBRIDGE | 6419730 | 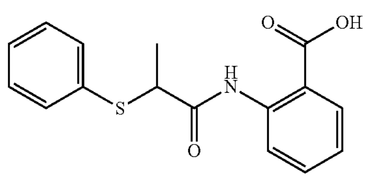 [SMILES: CC(Sc1ccccc1)C(=O)Nc1ccccc1C(=O)O] | 15% | 15% |
| 056 | SPECSNET | AF-826/ 30391019 | N.A. | 15% | 57% |
| 057 | CHEMBRIDGE | 6127069 | 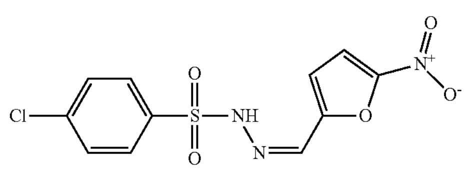 [SMILES: O=[N+]([O-])c1ccc(/C=N\NS(=O)(=O)c2ccc(Cl)cc2)o1] | 15% | 28% |
| 058 | CHEMBRIDGE | 7751796 | 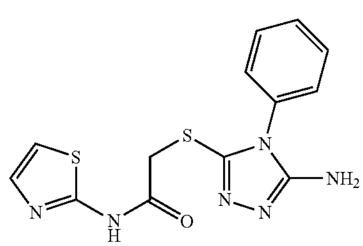 [SMILES: Nc1nnc(SCC(=O)Nc2nccs2)n1-c1ccccc1] | 15% | 0% |
| 059 | CHEMBRIDGE | 7936757 | 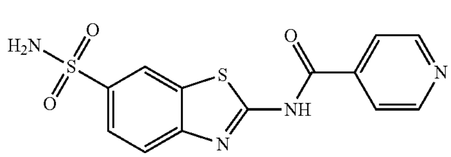 [SMILES: NS(=O)(=O)c1ccc2nc(NC(=O)c3ccncc3)sc2c1] | 15% | 0% |

TABLE 8-continued

| # | VENDOR | ID | STRUCTURE | INHIBITION | |
|---|---|---|---|---|---|
| | | | | E. coli | B. anthracis |
| 060 | CHEMBRIDGE | 5486578 | 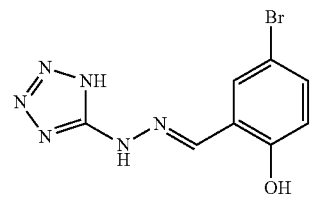 [SMILES: Oc1ccc(Br)cc1/C=N/Nc1nnn[nH]1] | 15% | 0% |
| 061 | CHEMBRIDGE | 5477578 | 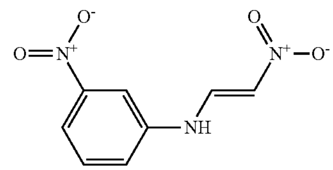 [SMILES: O=[N+]([O-])/C=C/Nc1cccc([N+](=O)[O-])c1] | 14% | 0% |
| 062 | CHEMBRIDGE | 5486271 | 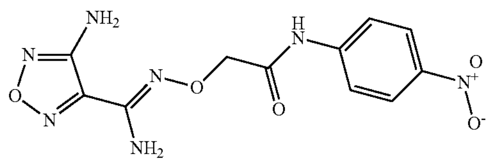 | 14% | 0% |
| 063 | CHEMDIV | 2083-0368 | 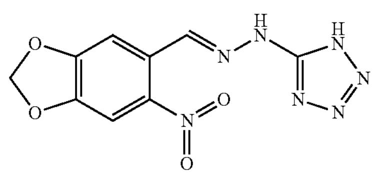 [SMILES: O=[N+]([O-])c1cc2c(cc1/C=N/Nc1nnn[nH]1)OCO2] | 14% | 81% |
| 064 | CHEMDIV | 8008-0603 | 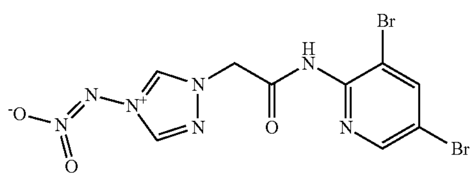 | 14% | 24% |
| 065 | CHEMBRIDGE | 7662712 | 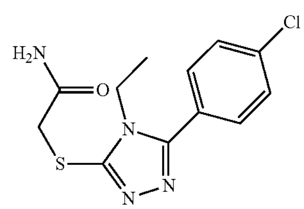 [SMILES: CCn1c(SCC(N)=O)nnc1-c1ccc(Cl)cc1] | 14% | 0% |
| 066 | CHEMDIV | 2113-0094 | 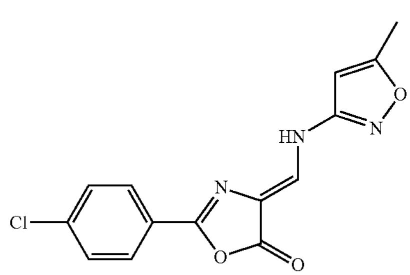 [SMILES: Cc1cc(N/C=C2\N=C(c3ccc(Cl)cc3)OC2=O)no1] | 13% | 80% |

TABLE 8-continued

| # | VENDOR | ID | STRUCTURE | INHIBITION | |
|---|---|---|---|---|---|
| | | | | E. coli | B. anthracis |
| 067 | CHEMBRIDGE | 5185703 | 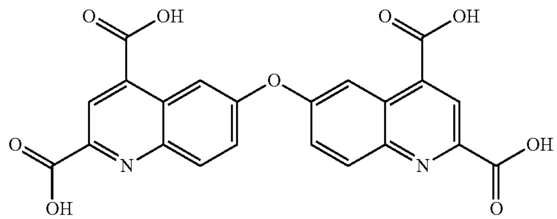 [SMILES: O=C(O)c1cc(C(=O)O)c2cc(Oc3ccc4nc(C(=O)O)cc(C(=O)O)c4c3)ccc2n1] | 13% | 1% |
| 068 | CHEMBRIDGE | 6049863 | 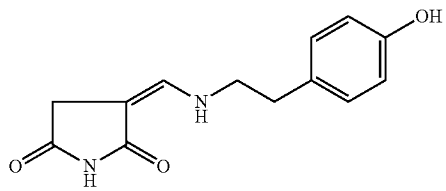 [SMILES: O=C1C/C(=C/NCCc2ccc(O)cc2)C(=O)N1] | 13% | 10% |
| 069 | CHEMBRIDGE | 6347634 | 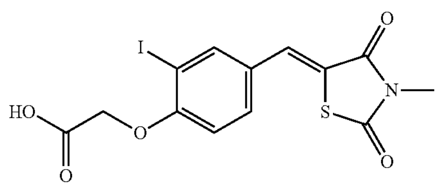 [SMILES: CN1C(=O)S/C(=C\c2ccc(OCC(=O)O)c(I)c2)C1=O] | 13% | 7% |
| 070 | CHEMBRIDGE | 5680859 | 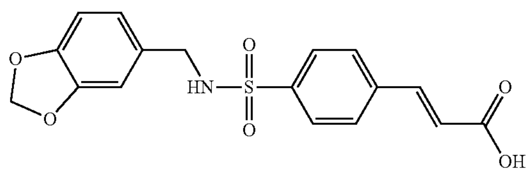 [SMILES: O=C(O)/C=C/c1ccc(S(=O)(=O)NCc2ccc3c(c2)OCO3)cc1] | 13% | 5% |
| 071 | CHEMBRIDGE | 5917405 | 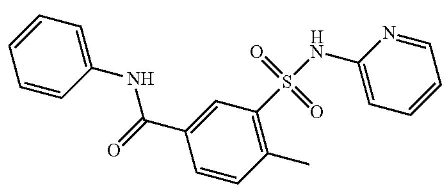 [SMILES: Cc1ccc(C(=O)Nc2ccccc2)cc1S(=O)(=O)Nc1ccccn1] | 12% | 7% |
| 072 | SPECSNET | AH-034/ 32474010 | 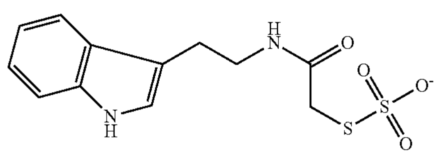 [SMILES: O=C(CSS(=O)(=O)[O-])NCCc1c[nH]c2ccccc12] | 12% | 0% |
| 073 | CHEMBRIDGE | 7425408 | 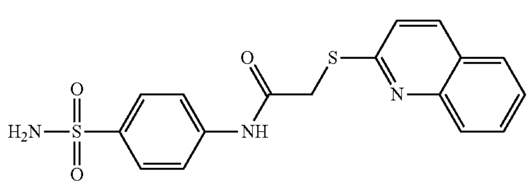 [SMILES: NS(=O)(=O)c1ccc(NC(=O)CSc2ccc3ccccc3n2)cc1] | 12% | 0% |
| 074 | CHEMBRIDGE | 5160262 | 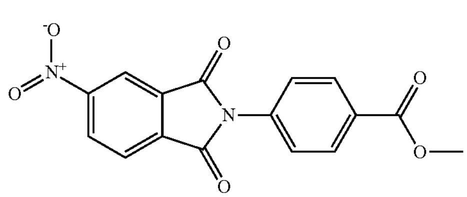 | 12% | 0% |

TABLE 8-continued

| # | VENDOR | ID | STRUCTURE | INHIBITION E. coli | B. anthracis |
|---|---|---|---|---|---|
| 075 | CHEMBRIDGE | 5914228 | 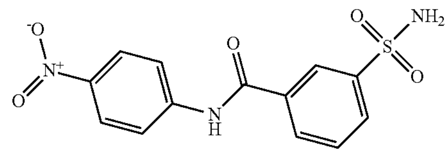 | 12% | 3% |
| 076 | CHEMBRIDGE | 5227209 | 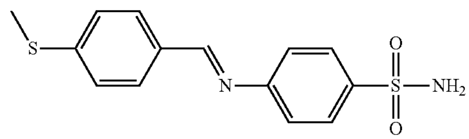 [SMILES: CSc1ccc(/C=N/c2ccc(S(N)(=O)=O)cc2)cc1] | 12% | 0% |
| 077 | SPECSNET | AG-205/ 36696020 | 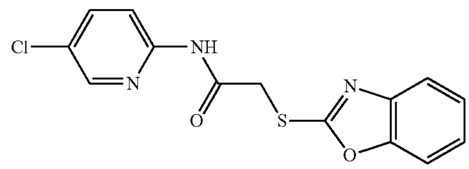 [SMILES: O=C(CSc1nc2ccccc2o1)Nc1ccc(Cl)cn1] | 12% | 0% |
| 078 | CHEMBRIDGE | 5173154 | 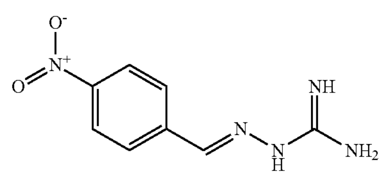 [SMILES: N=C(N)N/N=C/c1ccc([N+](=O)[O-])cc1] | 12% | 0% |
| 079 | CHEMBRIDGE | 5237216 | 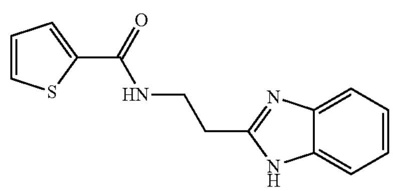 [SMILES: O=C(NCCc1nc2ccccc2[nH]1)c1cccs1] | 12% | 0% |
| 080 | CHEMBRIDGE | 5539186 | 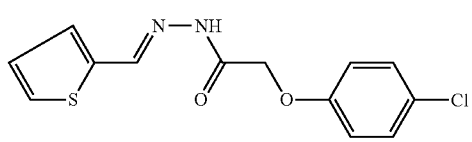 [SMILES: O=C(COc1ccc(Cl)cc1)N/N=C/c1cccs1] | 11% | 24% |
| 081 | CHEMBRIDGE | 5549749 | 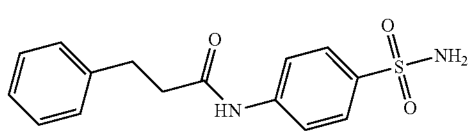 [SMILES: NS(=O)(=O)c1ccc(NC(=O)CCc2ccccc2)cc1] | 11% | 0% |
| 082 | MAYBRIDGE | DFP00019 | 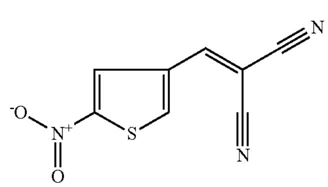 | 11% | 58% |
| 083 | CHEMBRIDGE | 7876010 | 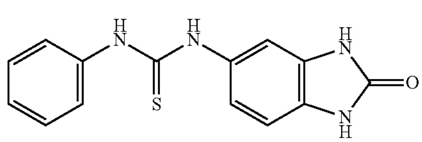 [SMILES: O=c1[nH]c2ccc(NC(=S)Nc3ccccc3)cc2[nH]1] | 11% | 0% |

TABLE 8-continued

| # | VENDOR | ID | STRUCTURE | INHIBITION | |
|---|---|---|---|---|---|
| | | | | E. coli | B. anthracis |
| 084 | CHEMBRIDGE | 7798274 | 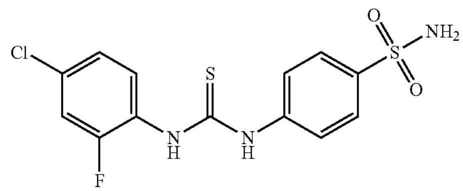 [SMILES: NS(=O)(=O)c1ccc(NC(=S)Nc2ccc(Cl)cc2F)cc1] | 11% | 0% |
| 085 | CHEMBRIDGE | 7528598 | 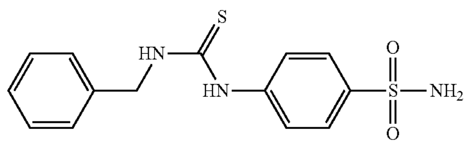 [SMILES: NS(=O)(=O)c1ccc(NC(=S)NCc2ccccc2)cc1] | 11% | 0% |
| 086 | CHEMBRIDGE | 7731718 | 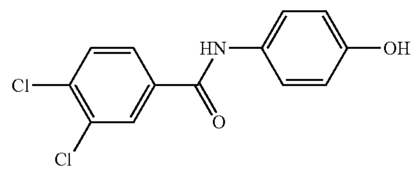 [SMILES: O=C(Nc1ccc(O)cc1)c1ccc(Cl)c(Cl)c1] | 11% | 0% |
| 087 | CHEMBRIDGE | 5213908 | 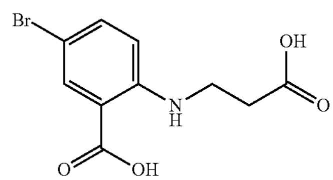 [SMILES: O=C(O)CCNc1ccc(Br)cc1C(=O)O] | 11% | 0% |
| 088 | CHEMBRIDGE | 7914818 | 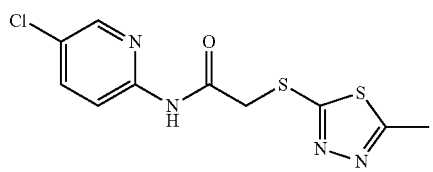 [SMILES: Cc1nnc(SCC(=O)Nc2ccc(Cl)cn2)s1] | 11% | 0% |
| 089 | SPECSNET | AE-848/ 33208046 | 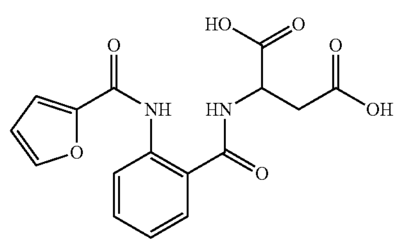 [SMILES: O=C(O)CC(NC(=O)c1ccccc1NC(=O)c1ccco1)C(=O)O] | 10% | 37% |
| 090 | CHEMBRIDGE | 7785233 | 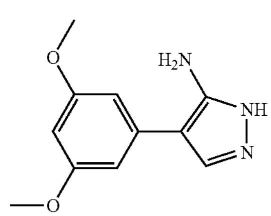 [SMILES: COc1cc(OC)cc(-c2cn[nH]c2N)c1] | 10% | 0% |
| 091 | CHEMBRIDGE | 7805704 | 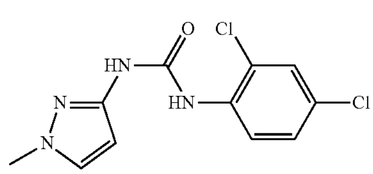 [SMILES: Cn1ccc(NC(=O)Nc2ccc(Cl)cc2Cl)n1] | 10% | 0% |

TABLE 8-continued
| # | VENDOR | ID | STRUCTURE | INHIBITION | |
|---|---|---|---|---|---|
| | | | | E. coli | B. anthracis |
| 092 | CHEMBRIDGE | 5269569 | 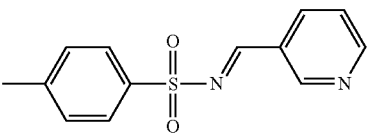 [SMILES: Cc1ccc(S(=O)(=O)/N=C/c2cccnc2)cc1] | 10% | 0% |
| 093 | CHEMBRIDGE | 5334483 | 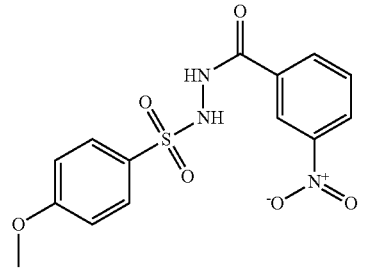 | 10% | 0% |
| 094 | CHEMBRIDGE | 7593154 | 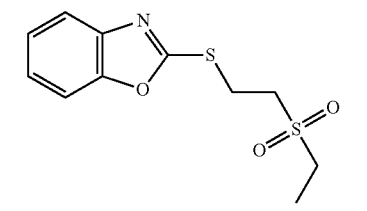 [SMILES: CCS(=O)(=O)CCSc1nc2ccccc2o1] | 10% | 0% |
| 095 | CHEMBRIDGE | 7502373 | 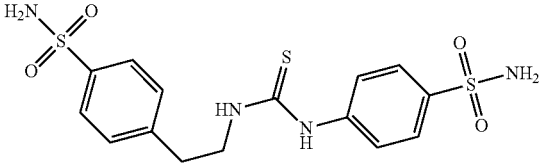 [SMILES: NS(=O)(=O)c1ccc(CCNC(=S)Nc2ccc(S(N)(=O)=O)cc2)cc1] | 10% | 0% |
| 096 | SPECSNET | AK-968/ 15359755 | N.A. | 10% | 25% |
| 097 | CHEMBRIDGE | 6160561 | 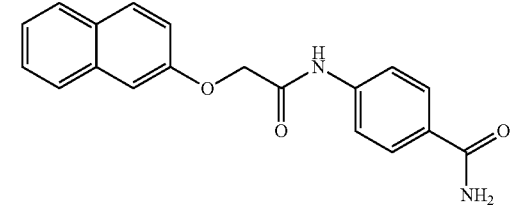 [SMILES: NC(=O)c1ccc(NC(=O)COc2ccc3ccccc3c2)cc1] | 10% | 63% |
| 098 | CHEMBRIDGE | 6381497 | 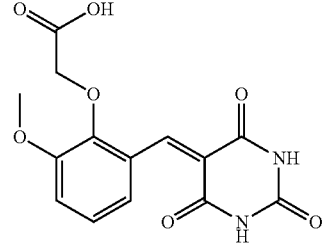 [SMILES: COc1cccc(C=C2C(=O)NC(=O)NC2=O)c1OCC(=O)O] | 10% | 13% |
| 099 | CHEMBRIDGE | 6592110 | 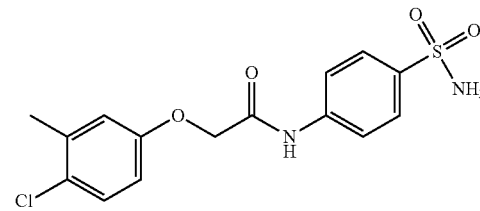 | 10% | 2% |

TABLE 8-continued

| # | VENDOR | ID | STRUCTURE | INHIBITION | |
|---|---|---|---|---|---|
| | | | | E. coli | B. anthracis |
| 100 | CHEMBRIDGE | 7661577 | 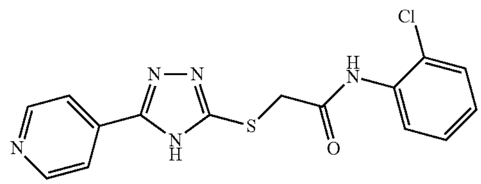 [SMILES: O=C(CSc1nnc(-c2ccncc2)[nH]1)Nc1ccccc1Cl] | 9% | 0% |
| 101 | CHEMBRIDGE | 7447806 | 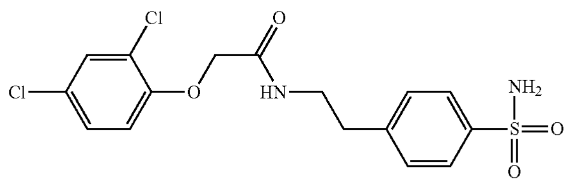 [SMILES: NS(=O)(=O)c1ccc(CCNC(=O)COc2ccc(Cl)cc2Cl)cc1] | 9% | 0% |
| 102 | CHEMBRIDGE | 5728173 | 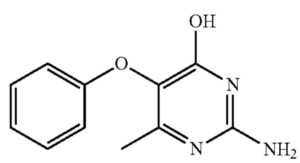 [SMILES: Cc1nc(N)nc(O)c1Oc1ccccc1] | 9% | 6% |
| 103 | CHEMBRIDGE | 7907251 | 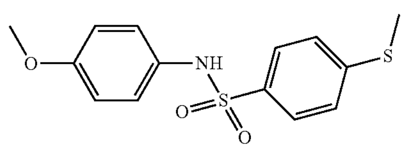 | 9% | 0% |
| 104 | CHEMBRIDGE | 5925415 | 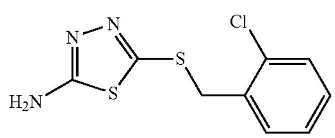 [SMILES: Nc1nnc(SCc2ccccc2Cl)s1] | 9% | 29% |
| 105 | CHEMBRIDGE | 6652134 | 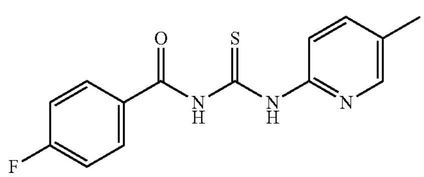 [SMILES: Cc1ccc(NC(=S)NC(=O)c2ccc(F)cc2)nc1] | 9% | 51% |
| 106 | SPECSNET | AR-360/42760781 | 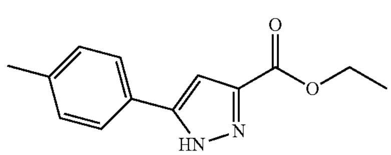 [SMILES: CCOC(=O)c1cc(-c2ccc(C)cc2)[nH]n1] | 9% | 0% |
| 107 | CHEMBRIDGE | 5548185 | 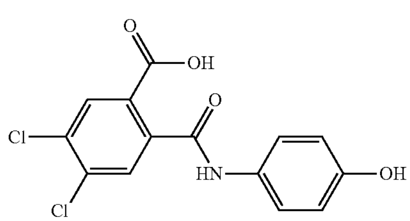 [SMILES: O=C(O)c1cc(Cl)c(Cl)cc1C(=O)Nc1ccc(O)cc1] | 9% | 0% |

TABLE 8-continued

| # | VENDOR | ID | STRUCTURE | INHIBITION | |
|---|---|---|---|---|---|
| | | | | E. coli | B. anthracis |
| 108 | CHEMBRIDGE | 7682880 | 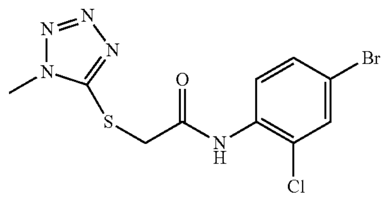 [SMILES: Cn1nnnc1SCC(=O)Nc1ccc(Br)cc1Cl] | 9% | 0% |
| 109 | CHEMBRIDGE | 5798423 | 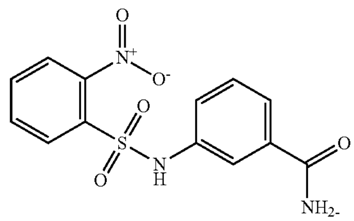 | 9% | 8% |
| 110 | CHEMBRIDGE | 7883375 | 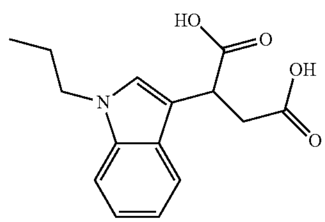 [SMILES: CCCn1cc(C(CC(=O)O)C(=O)O)c2ccccc21] | 9% | 0% |
| 111 | CHEMBRIDGE | 5679270 | 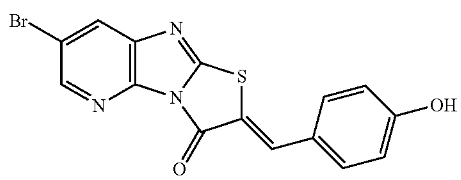 [SMILES: O=c1/c(=C/c2ccc(O)cc2)sc2nc3cc(Br)cnc3n12] | 9% | 6% |
| 112 | SPECSNET | AC-907/ 34131053 | 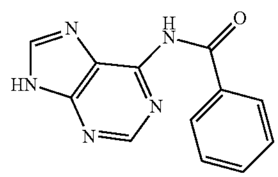 [SMILES: O=C(Nc1ncnc2[nH]cnc12)c1ccccc1] | 8% | 0% |
| 113 | CHEMBRIDGE | 6111462 | 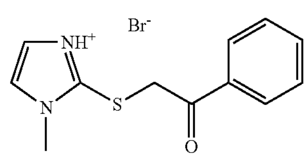 [SMILES: Cn1cc[nH+]c1SCC(=O)c1ccccc1 ; [Br-]] | 8% | 12% |
| 114 | CHEMBRIDGE | 5553328 | 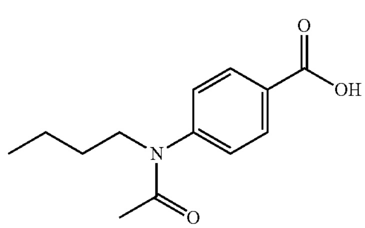 [SMILES: CCCCN(C(C)=O)c1ccc(C(=O)O)cc1] | 8% | 0% |

TABLE 8-continued

| # | VENDOR | ID | STRUCTURE | INHIBITION E. coli | INHIBITION B. anthracis |
|---|--------|----|-----------|--------|-------------|
| 115 | SPECSNET | AG-690/ 15432542 | 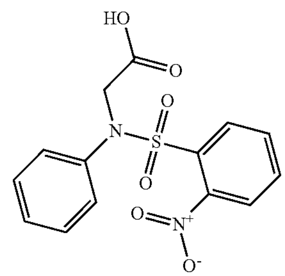 [SMILES: O=C(O)CN(c1ccccc1)S(=O)(=O)c1ccccc1[N+](=O)[O-]] | 8% | 0% |
| 116 | SPECSNET | AN-465/ 14952181 | 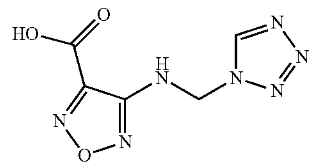 [SMILES: O=C(O)c1nonc1NCn1cnnn1] | 8% | 5% |
| 117 | SPECSNET | AK-968/ 37166199 | 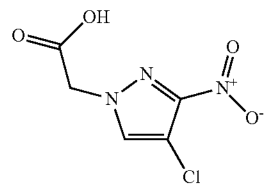 [SMILES: O=C(O)Cn1cc(Cl)c([N+](=O)[O-])n1] | 8% | 14% |
| 118 | CHEMBRIDGE | 5323892 | 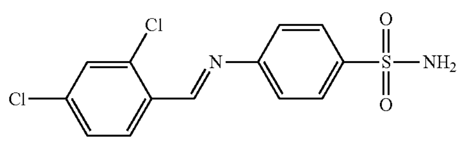 [SMILES: NS(=O)(=O)c1ccc(/N=C/c2ccc(Cl)cc2Cl)cc1] | 8% | 0% |
| 119 | CHEMBRIDGE | 5115114 | 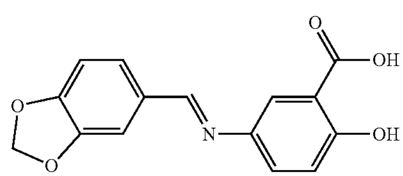 [SMILES: O=C(O)c1cc(/N=C/c2ccc3c(c2)OCO3)ccc1O] | 8% | 0% |
| 120 | CHEMBRIDGE | 5117115 | 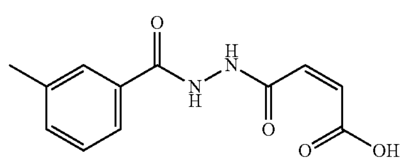 [SMILES: Cc1cccc(C(=O)NNC(=O)/C=C\C(=O)O)c1] | 8% | 0% |
| 121 | CHEMBRIDGE | 7791534 | 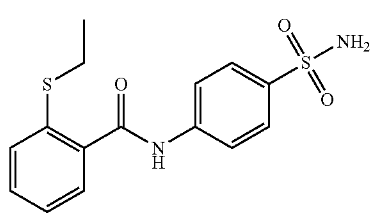 [SMILES: CCSc1ccccc1C(=O)Nc1ccc(S(N)(=O)=O)cc1] | 8% | 0% |

TABLE 8-continued

| # | VENDOR | ID | STRUCTURE | INHIBITION | |
|---|---|---|---|---|---|
| | | | | E. coli | B. anthracis |
| 122 | CHEMBRIDGE | 6081374 | 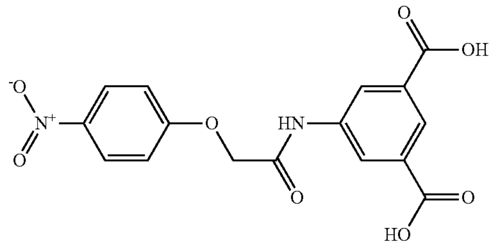 | 7% | 6% |
| 123 | CHEMBRIDGE | 7299424 | 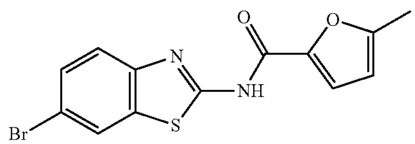 [SMILES: Cc1ccc(C(=O)Nc2nc3ccc(Br)cc3s2)o1] | 7% | 0% |
| 124 | CHEMBRIDGE | 7024854 | 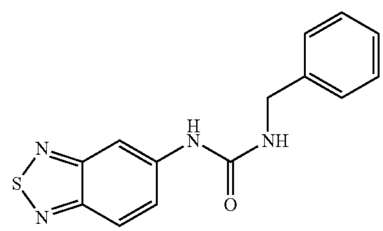 [SMILES: O=C(NCc1ccccc1)Nc1ccc2nsnc2c1] | 7% | 0% |
| 125 | CHEMBRIDGE | 7270409 | 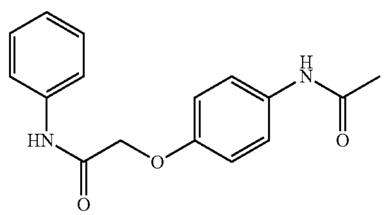 [SMILES: CC(=O)Nc1ccc(OCC(=O)Nc2ccccc2)cc1] | 7% | 0% |
| 126 | CHEMBRIDGE | 6480574 | 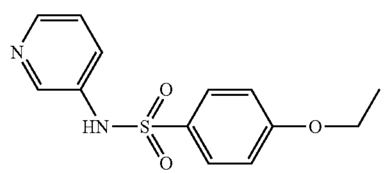 [SMILES: CCOc1ccc(S(=O)(=O)Nc2cccnc2)cc1] | 7% | 22% |
| 127 | CHEMDIV | 4553-3701 | 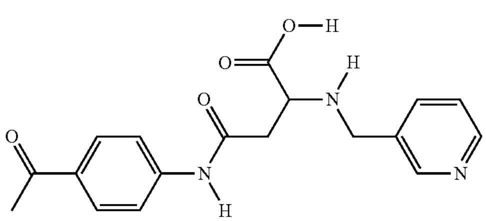 [SMILES: CC(=O)c1ccc(NC(=O)CC(NCc2cccnc2)C(=O)O)cc1] | 7% | 59% |
| 128 | CHEMBRIDGE | 7845106 | 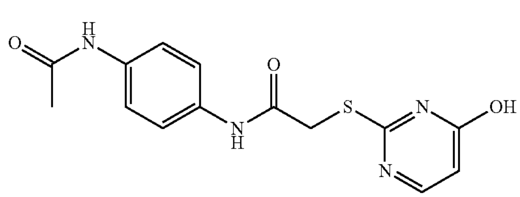 [SMILES: CC(=O)Nc1ccc(NC(=O)CSc2nccc(O)n2)cc1] | 7% | 0% |
| 129 | SPECSNET | AH-487/42193471 | 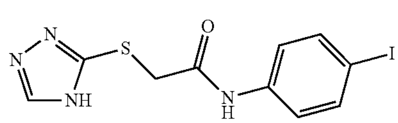 [SMILES: O=C(CSc1nnc[nH]1)Nc1ccc(I)cc1] | 7% | 0% |

TABLE 8-continued

| # | VENDOR | ID | STRUCTURE | INHIBITION E. coli | B. anthracis |
|---|---|---|---|---|---|
| 130 | MAYBRIDGE | NRB00686 | 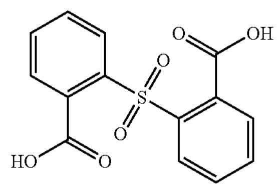 [SMILES: O=C(O)c1ccccc1S(=O)(=O)c1ccccc1C(=O)O] | 7% | 28% |
| 131 | CHEMBRIDGE | 5227097 | 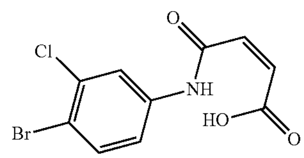 [SMILES: O=C(O)/C=C\C(=O)Nc1ccc(Br)c(Cl)c1] | 7% | 0% |
| 132 | CHEMBRIDGE | 5320808 | 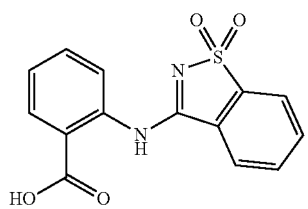 [SMILES: O=C(O)c1ccccc1NC1=NS(=O)(=O)c2ccccc21] | 6% | 25% |
| 133 | MAYBRIDGE | SP00001 | N.A. | 6% | 38% |
| 134 | CHEMBRIDGE | 5186398 | 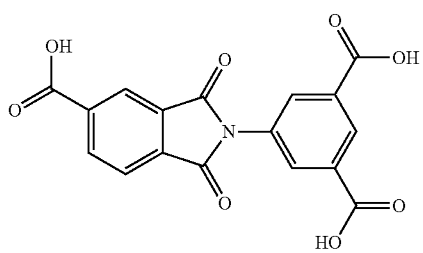 [SMILES: O=C(O)c1cc(C(=O)O)cc(N2C(=O)c3ccc(C(=O)O)cc3C2=O)c1] | 6% | 0% |
| 135 | CHEMBRIDGE | 5201899 | 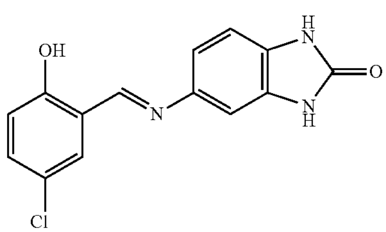 [SMILES: O=c1[nH]c2ccc(/N=C/c3cc(Cl)ccc3O)cc2[nH]1] | 6% | 10% |
| 136 | SPECSNET | AG-690/ 40246195 | 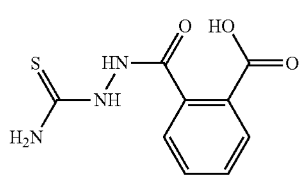 [SMILES: NC(=S)NNC(=O)c1ccccc1C(=O)O] | 6% | 64% |
| 137 | CHEMBRIDGE | 6734700 | 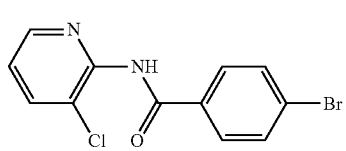 [SMILES: O=C(Nc1ncccc1Cl)c1ccc(Br)cc1] | 6% | 7% |

TABLE 8-continued

| # | VENDOR | ID | STRUCTURE | INHIBITION E. coli | INHIBITION B. anthracis |
|---|---|---|---|---|---|
| 138 | CHEMBRIDGE | 5934320 | 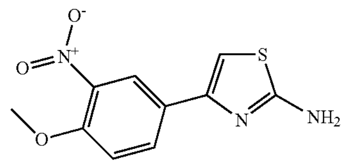 [SMILES: COc1ccc(-c2csc(N)n2)cc1[N+](=O)[O-]] | 6% | 54% |
| 139 | CHEMBRIDGE | 7876477 | 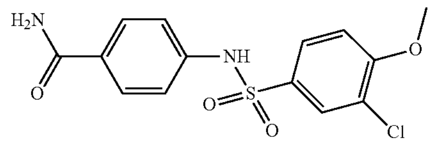 [SMILES: COc1ccc(S(=O)(=O)Nc2ccc(C(N)=O)cc2)cc1Cl] | 6% | 0% |
| 140 | CHEMBRIDGE | 7929927 | 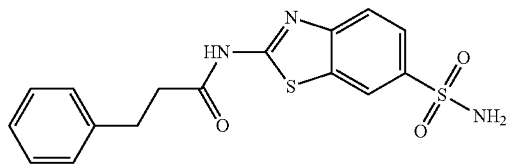 [SMILES: NS(=O)(=O)c1ccc2nc(NC(=O)CCc3ccccc3)sc2c1] | 6% | 0% |
| 141 | MAYBRIDGE | CC18401 | 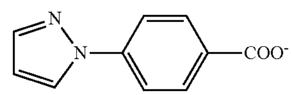 | 6% | 17% |
| 142 | CHEMBRIDGE | 5175596 | 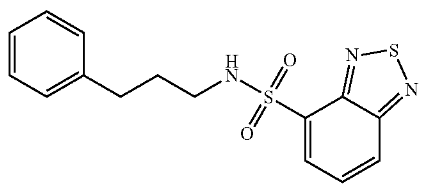 [SMILES: O=S(=O)(NCCCc1ccccc1)c1cccc2nsnc12] | 6% | 0% |
| 143 | CHEMBRIDGE | 5621555 | 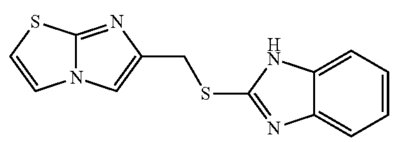 [SMILES: c1ccc2[nH]c(SCc3cn4ccsc4n3)nc2c1] | 6% | 2% |
| 144 | CHEMBRIDGE | 6449068 | 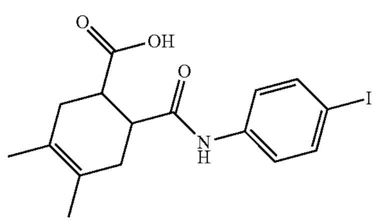 [SMILES: CC1=C(C)CC(C(=O)Nc2ccc(I)cc2)C(C(=O)O)C1] | 6% | 65% |
| 145 | SPECSNET | AN-988/ 42879152 | 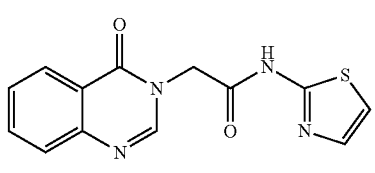 [SMILES: O=C(Cn1cnc2ccccc2c1=O)Nc1nccs1] | 6% | 0% |
| 146 | CHEMBRIDGE | 5907193 | 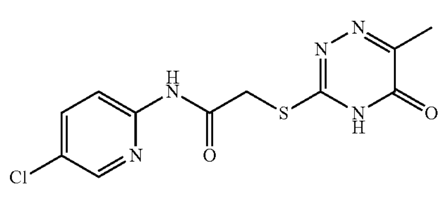 [SMILES: Cc1nnc(SCC(=O)Nc2ccc(Cl)cn2)[nH]c1=O] | 5% | 11% |

TABLE 8-continued
| # | VENDOR | ID | STRUCTURE | INHIBITION | |
|---|---|---|---|---|---|
| | | | | E. coli | B. anthracis |
| 147 | CHEMDIV | 2181-0361 | 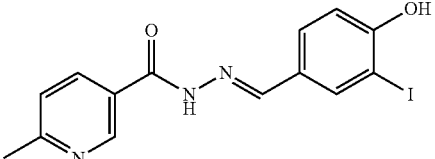 | 5% | 12% |
| 148 | MAYBRIDGE | KM08231 | 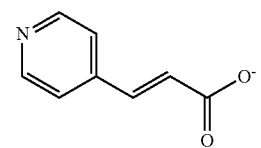 | 5% | 4% |
| 149 | CHEMBRIDGE | 7744903 | 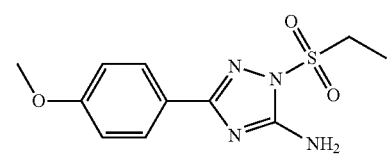 | 5% | 0% |
| 150 | SPECSNET | AN-465/ 42887914 | 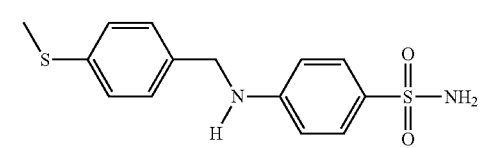 [SMILES: CSc1ccc(CNc2ccc(S(N)(=O)=O)cc2)cc1] | 5% | 0% |
| 151 | SPECSNET | AQ-911/ 42464333 | 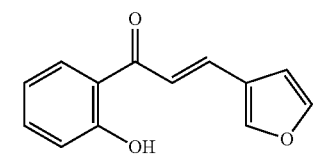 [SMILES: O=C(/C=C/c1ccoc1)c1ccccc1O] | 5% | 0% |
| 152 | CHEMBRIDGE | 5221975 | 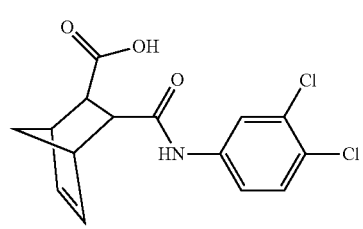 [SMILES: O=C(O)C1C2C=CC(C2)C1C(=O)Nc1ccc(Cl)c(Cl)c1] | 5% | 0% |
| 153 | CHEMBRIDGE | 6999589 | 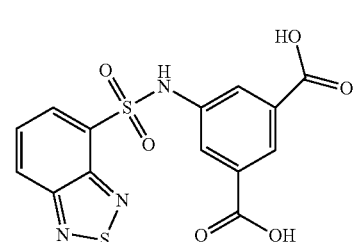 | 5% | 0% |
| 154 | CHEMBRIDGE | 7693552 | 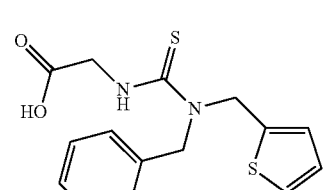 | 5% | 0% |

TABLE 8-continued

| # | VENDOR | ID | STRUCTURE | INHIBITION | |
|---|--------|-----|-----------|------------|---|
| | | | | E. coli | B. anthracis |
| 155 | CHEMDIV | 3820-2901 | 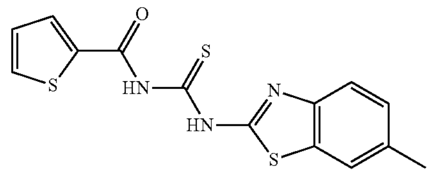 [SMILES: Cc1ccc2nc(NC(=S)NC(=O)c3cccs3)sc2c1] | 5% | 26% |
| 156 | SPECSNET | AA-516/ 25012123 | 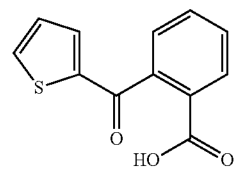 [SMILES: O=C(O)c1ccccc1C(=O)c1cccs1] | 5% | 22% |
| 157 | SPECSNET | AN-465/ 42888516 | 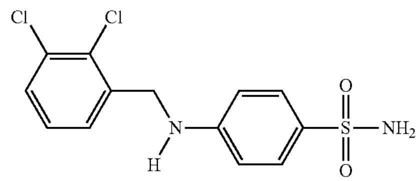 [SMILES: NS(=O)(=O)c1ccc(NCc2cccc(Cl)c2Cl)cc1] | 5% | 0% |
| 158 | MAYBRIDGE | KM02656 | 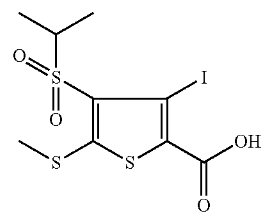 [SMILES: CSc1sc(C(=O)O)c(I)c1S(=O)(=O)C(C)C] | 4% | 36% |
| 159 | NANOSYN | NS33821 | 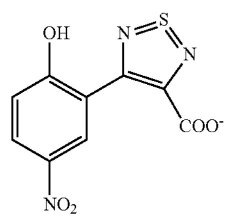 | 4% | 1% |
| 160 | SPECSNET | AG-690/ 13508068 | 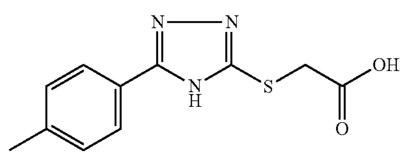 [SMILES: Cc1ccc(-c2nnc(SCC(=O)O)[nH]2)cc1] | 4% | 0% |
| 161 | MAYBRIDGE | SEW00351 | 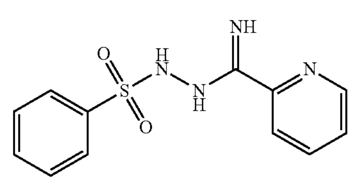 [SMILES: N=C(NNS(=O)(=O)c1ccccc1)c1ccccn1] | 4% | 68% |
| 162 | CHEMDIV | 0783-0142 | 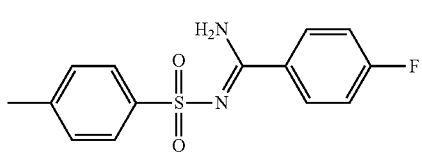 [SMILES: Cc1ccc(S(=O)(=O)/N=C(\N)c2ccc(F)cc2)cc1] | 4% | 0% |

TABLE 8-continued

| # | VENDOR | ID | STRUCTURE | INHIBITION | |
|---|---|---|---|---|---|
| | | | | E. coli | B. anthracis |
| 163 | CHEMBRIDGE | 6229693 | 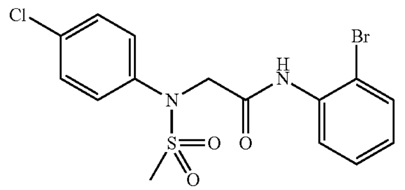 [SMILES: CS(=O)(=O)N(CC(=O)Nc1ccccc1Br)c1ccc(Cl)cc1] | 4% | 54% |
| 164 | CHEMDIV | 4585-0016 | 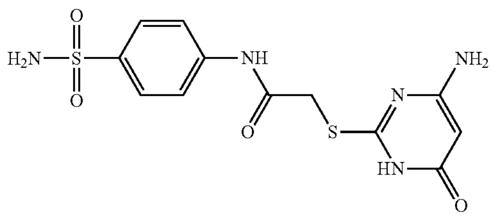 [SMILES: Nc1cc(=O)[nH]c(SCC(=O)Nc2ccc(S(N)(=O)=O)cc2)n1] | 4% | 32% |
| 165 | CHEMBRIDGE | 5467380 | 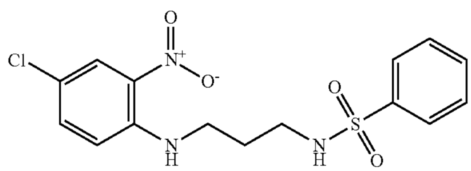 [SMILES: O=[N+]([O-])c1cc(Cl)ccc1NCCCNS(=O)(=O)c1ccccc1] | 4% | 0% |
| 166 | CHEMBRIDGE | 5227796 | 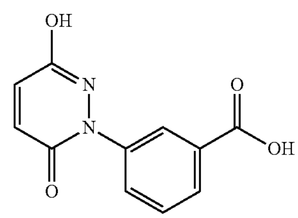 [SMILES: O=C(O)c1cccc(-n2nc(O)ccc2=O)c1] | 4% | 19% |
| 167 | SPECSNET | AF-399/ 15335566 | 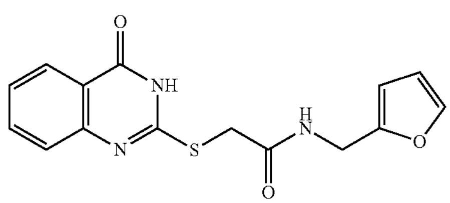 [SMILES: O=C(CSc1nc2ccccc2c(=O)[nH]1)NCc1ccco1] | 4% | 0% |
| 168 | SPECSNET | AG-690/ 15444484 | 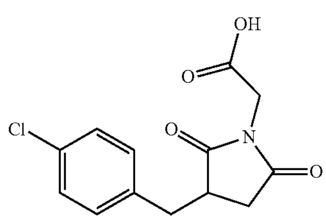 [SMILES: O=C(O)CN1C(=O)CC(Cc2ccc(Cl)cc2)C1=O] | 3% | 0% |
| 169 | CHEMBRIDGE | 7842136 | 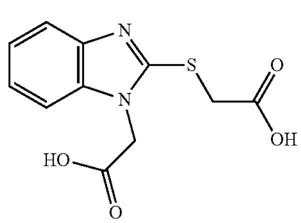 [SMILES: O=C(O)CSc1nc2ccccc2n1CC(=O)O] | 3% | 0% |

TABLE 8-continued

| # | VENDOR | ID | STRUCTURE | INHIBITION E. coli | INHIBITION B. anthracis |
|---|---|---|---|---|---|
| 170 | CHEMBRIDGE | 7697135 | 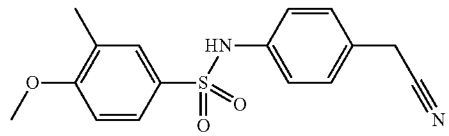 [SMILES: COc1ccc(S(=O)(=O)Nc2ccc(CC#N)cc2)cc1C] | 3% | 0% |
| 171 | SPECSNET | AK-968/ 41026368 | 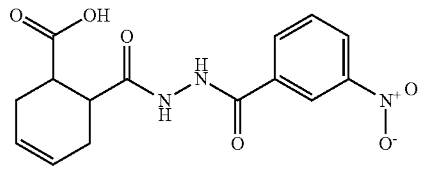 | 3% | 24% |
| 172 | SPECSNET | AN-989/ 14834030 | 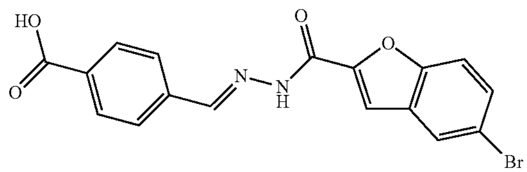 [SMILES: O=C(O)c1ccc(/C=N/NC(=O)c2cc3cc(Br)ccc3o2)cc1] | 3% | 32% |
| 173 | CHEMBRIDGE | 7741517 | 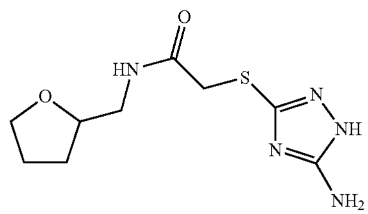 [SMILES: Nc1nc(SCC(=O)NCC2CCCO2)n[nH]1] | 3% | 0% |
| 174 | SPECSNET | AG-205/ 32366049 | 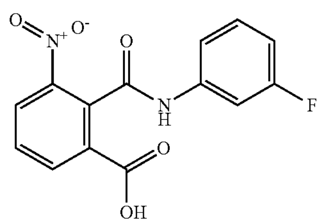 | 3% | 11% |
| 175 | CHEMBRIDGE | 7579538 | 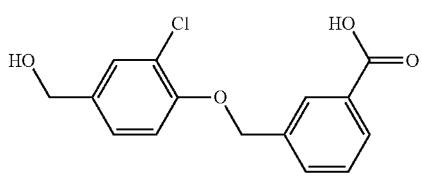 [SMILES: O=C(O)c1cccc(COc2ccc(CO)cc2Cl)c1] | 3% | 0% |
| 176 | SPECSNET | AN-465/ 15401042 | 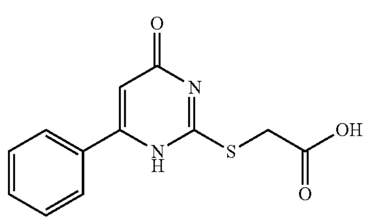 [SMILES: O=C(O)CSc1nc(=O)cc(-c2ccccc2)[nH]1] | 3% | 0% |
| 177 | CHEMDIV | 8006-2677 | 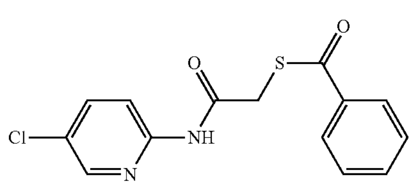 [SMILES: O=C(CSC(=O)c1ccccc1)Nc1ccc(Cl)cn1] | 3% | 21% |

TABLE 8-continued

| # | VENDOR | ID | STRUCTURE | INHIBITION E. coli | B. anthracis |
|---|--------|-----|-----------|---------|-------------|
| 178 | CHEMBRIDGE | 7842469 | 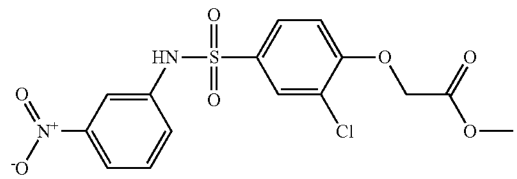 | 3% | 0% |
| 179 | SPECSNET | AO-080/ 42479871 | 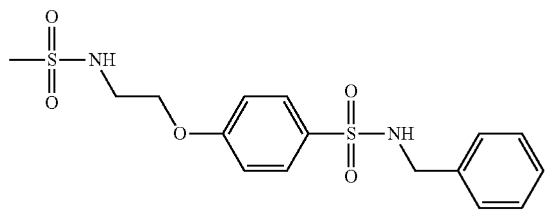 [SMILES: CS(=O)(=O)NCCOc1ccc(S(=O)(=O)NCc2ccccc2)cc1] | 3% | 0% |
| 180 | CHEMDIV | 5983-3833 | 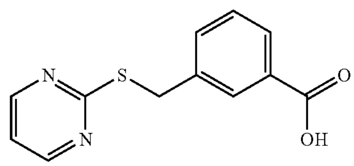 [SMILES: O=C(O)c1cccc(CSc2ncccn2)c1] | 3% | 15% |
| 181 | CHEMBRIDGE | 6047550 | 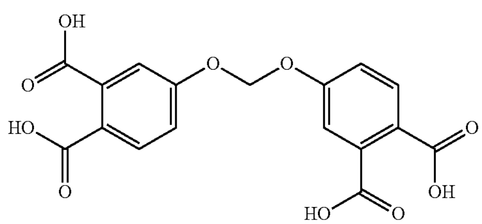 [SMILES: O=C(O)c1ccc(OCOc2ccc(C(=O)O)c(C(=O)O)c2)cc1C(=O)O] | 3% | 56% |
| 182 | CHEMDIV | 1889-3325 | 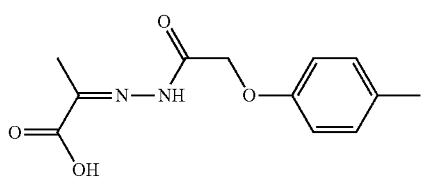 [SMILES: CC(=NNC(=O)COc1ccc(C)cc1)C(=O)O] | 3% | 14% |
| 183 | CHEMDIV | 7213-0565 | 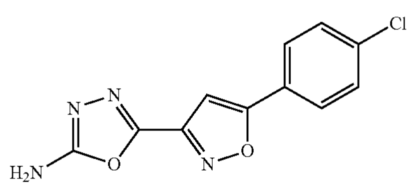 [SMILES: Nc1nnc(-c2cc(-c3ccc(Cl)cc3)on2)o1] | 3% | 7% |
| 184 | CHEMBRIDGE | 6723183 | 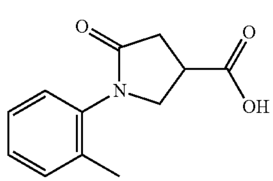 [SMILES: Cc1ccccc1N1CC(C(=O)O)CC1=O] | 2% | 16% |

TABLE 8-continued

| # | VENDOR | ID | STRUCTURE | INHIBITION | |
|---|--------|-----|-----------|------------|-----|
| | | | | E. coli | B. anthracis |
| 185 | NANOSYN | NS8477 | 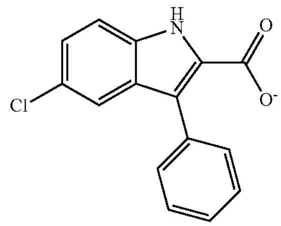 [SMILES: O=C([O-])c1[nH]c2ccc(Cl)cc2c1-c1ccccc1] | 2% | 40% |
| 186 | CHEMDIV | 1831-0153 | 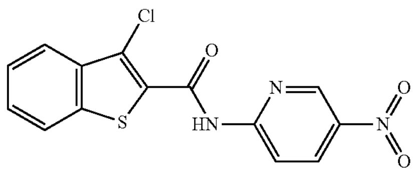 [SMILES: O=C(Nc1ccc([N+](=O)[O-])cn1)c1sc2ccccc2c1Cl] | 2% | 9% |
| 187 | CHEMBRIDGE | 7633313 | 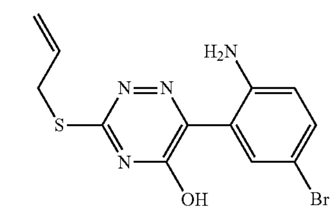 [SMILES: C=CCSc1nnc(-c2cc(Br)ccc2N)c(O)n1] | 2% | 0% |
| 188 | CHEMBRIDGE | 7316103 | 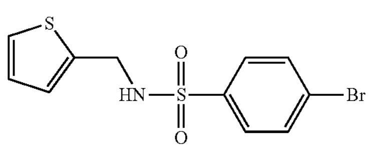 [SMILES: O=S(=O)(NCc1cccs1)c1ccc(Br)cc1] | 1% | 0% |
| 189 | CHEMDIV | 2389-1926 | 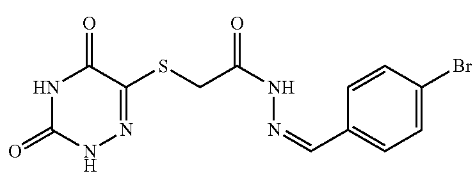 [SMILES: O=C(CSc1n[nH]c(=O)[nH]c1=O)N/N=C\c1ccc(Br)cc1] | 1% | 0% |
| 190 | SPECSNET | AQ-360/41615677 | 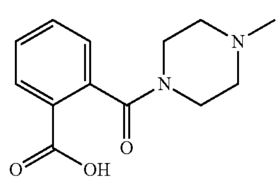 [SMILES: CN1CCN(C(=O)c2ccccc2C(=O)O)CC1] | 1% | 0% |
| 191 | MAYBRIDGE | SEW05479 | 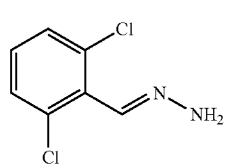 [SMILES: N/N=C/c1c(Cl)cccc1Cl] | 1% | 5% |

TABLE 8-continued
| # | VENDOR | ID | STRUCTURE | INHIBITION E. coli | INHIBITION B. anthracis |
|---|---|---|---|---|---|
| 192 | SPECSNET | AG-690/ 15439214 | 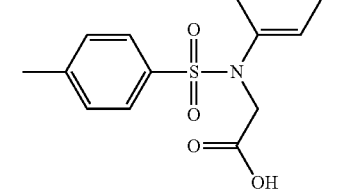 | 1% | 0% |
| 193 | CHEMBRIDGE | 5220945 | 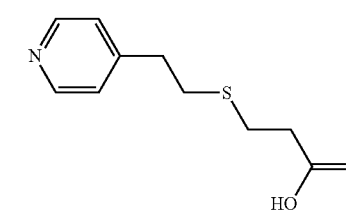 | 1% | 18% |
| 194 | CHEMDIV | 4361-0771 | 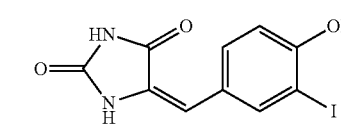 | 1% | 62% |
| 195 | CHEMBRIDGE | 5571553 | 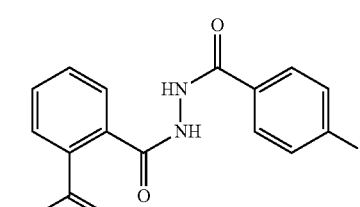 | 1% | 0% |
| 196 | CHEMDIV | C563-0504 | 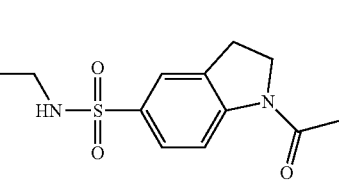 | 1% | 52% |
| 197 | CHEMBRIDGE | 6341126 | 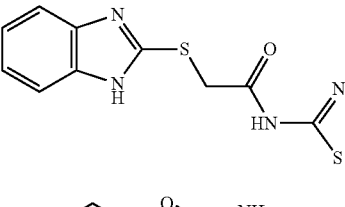 | 0% | 34% |
| 198 | CHEMDIV | 3966-3528 | 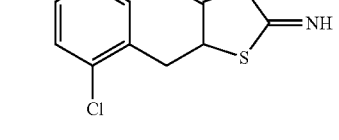 | 0% | 7% |
| 199 | SPECSNET | AQ-390/ 14195074 | 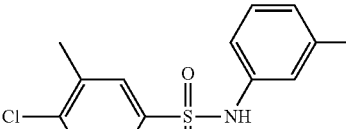 | 0% | 0% |

TABLE 8-continued

| # | VENDOR | ID | STRUCTURE | INHIBITION | |
|---|---|---|---|---|---|
| | | | | E. coli | B. anthracis |
| 200 | CHEMBRIDGE | 6048997 | 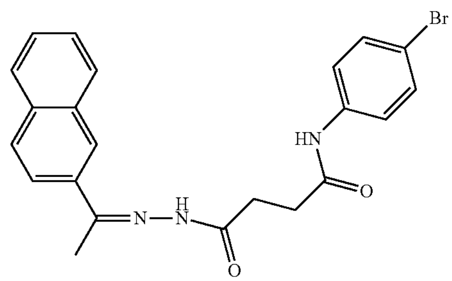 [SMILES: CC(=NNC(=O)CCC(=O)Nc1ccc(Br)cc1)c1ccc2ccccc2c1] | 0% | 76% |
| 201 | CHEMDIV | 5618-4578 | 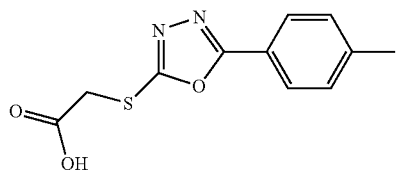 [SMILES: Cc1ccc(-c2nnc(SCC(=O)O)o2)cc1] | 0% | 25% |
| 202 | MAYBRIDGE | BTB00374 | 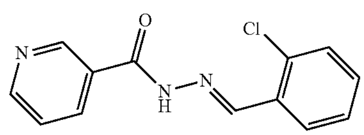 [SMILES: O=C(N/N=C/c1ccccc1Cl)c1cccnc1] | 0% | 32% |
| 203 | CHEMBRIDGE | 7800297 | 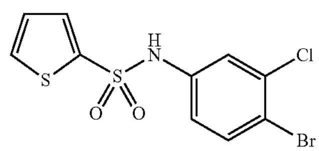 [SMILES: O=S(=O)(Nc1ccc(Br)c(Cl)c1)c1cccs1] | 0% | 0% |
| 204 | CHEMDIV | 0285-0072 | 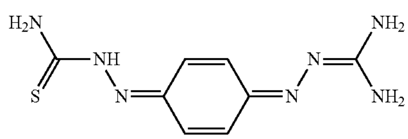 [SMILES: NC(=S)NN=C1C=CC(=NN=C(N)N)C=C1] | 0% | 0% |
| 205 | CHEMDIV | 5024-0069 | 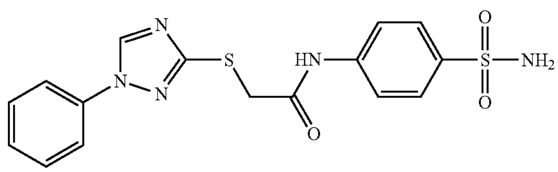 [SMILES: NS(=O)(=O)c1ccc(NC(=O)CSc2ncn(-c3ccccc3)n2)cc1] | 0% | 40% |
| 206 | CHEMDIV | 5743-0118 | 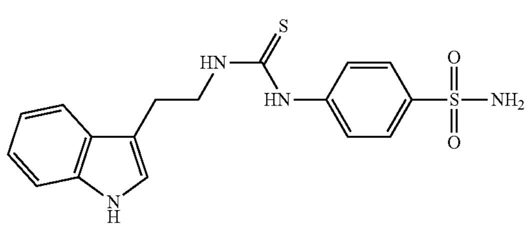 [SMILES: NS(=O)(=O)c1ccc(NC(=S)NCCc2c[nH]c3ccccc23)cc1] | 0% | 25% |
| 207 | CHEMDIV | 2216-0001 | 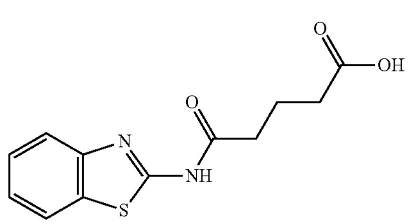 [SMILES: O=C(O)CCCC(=O)Nc1nc2ccccc2s1] | 0% | 7% |

TABLE 8-continued

| # | VENDOR | ID | STRUCTURE | INHIBITION | |
|---|--------|-----|-----------|-----------|---|
| | | | | E. coli | B. anthracis |
| 208 | CHEMBRIDGE | 7207373 | 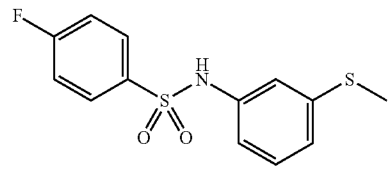 [SMILES: CSc1cccc(NS(=O)(=O)c2ccc(F)cc2)c1] | 0% | 0% |
| 209 | CHEMBRIDGE | 7729104 | 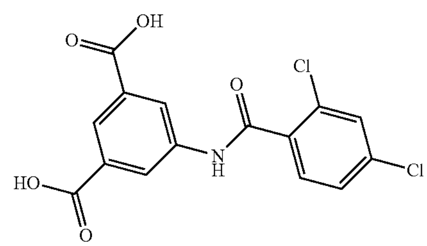 [SMILES: O=C(O)c1cc(NC(=O)c2ccc(Cl)cc2Cl)cc(C(=O)O)c1] | 0% | 0% |
| 210 | CHEMDIV | 8012-2515 | N.A. | 0% | 0% |
| 211 | CHEMDIV | 2112-0007 | 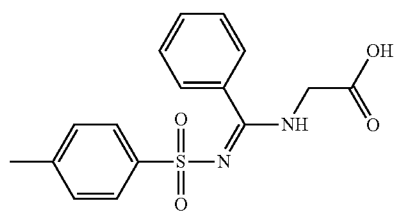 [SMILES: Cc1ccc(S(=O)(=O)/N=C(/NCC(=O)O)c2ccccc2)cc1] | 0% | 42% |
| 212 | CHEMBRIDGE | 6658496 | 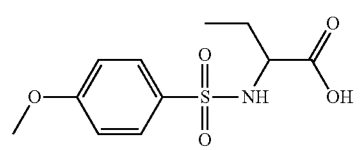 [SMILES: CCC(NS(=O)(=O)c1ccc(OC)cc1)C(=O)O] | 0% | 32% |
| 213 | CHEMBRIDGE | 6181516 | 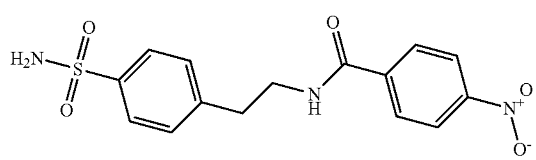 | 0% | 54% |
| 214 | CHEMDIV | 1636-0418 | 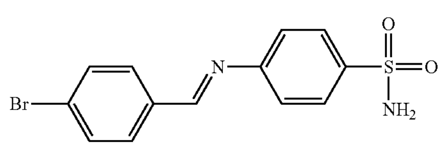 [SMILES: NS(=O)(=O)c1ccc(/N=C/c2ccc(Br)cc2)cc1] | 0% | 0% |
| 215 | CHEMDIV | 3453-1439 | N.A. | 0% | 9% |
| 216 | CHEMDIV | 5186-0454 | 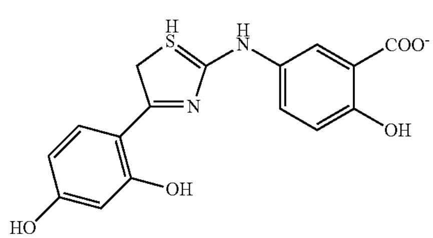 | 0% | 35% |

TABLE 8-continued

| # | VENDOR | ID | STRUCTURE | INHIBITION | |
|---|--------|-----|-----------|------------|--|
| | | | | E. coli | B. anthracis |
| 217 | CHEMDIV | C301-2383 | 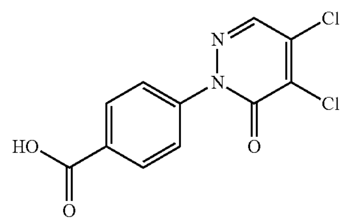 [SMILES: O=C(O)c1ccc(-n2ncc(Cl)c(Cl)c2=O)cc1] | 0% | 0% |
| 218 | CHEMDIV | 7009-0719 | 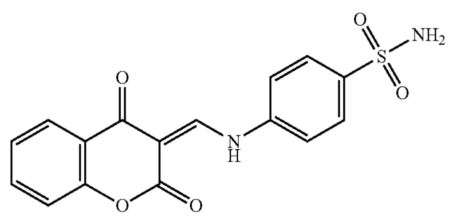 [SMILES: NS(=O)(=O)c1ccc(N/C=C2\C(=O)Oc3ccccc3C2=O)cc1] | 0% | 0% |
| 219 | CHEMDIV | 3583-1608 | 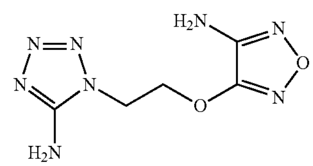 [SMILES: Nc1nonc1OCCn1nnnc1N] | 0% | 12% |
| 220 | CHEMDIV | 7009-0720 | 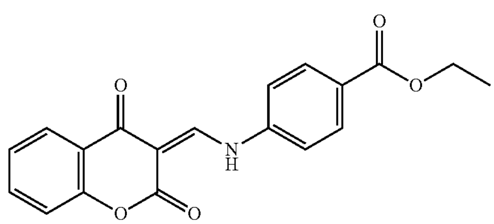 [SMILES: CCOC(=O)c1ccc(N/C=C2\C(=O)Oc3ccccc3C2=O)cc1] | 0% | 0% |
| 221 | CHEMBRIDGE | 6464120 | 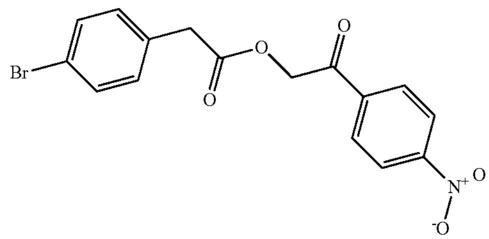 | 0% | 57% |
| 222 | SPECSNET | AN-329/ 43211385 | 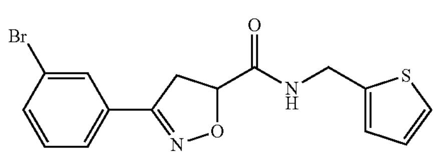 [SMILES: O=C(NCc1cccs1)C1CC(c2cccc(Br)c2)=NO1] | 0% | 0% |
| 223 | CHEMBRIDGE | 5232480 | 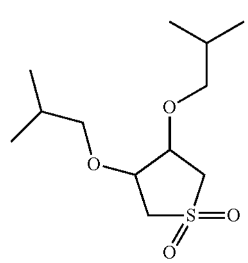 [SMILES: CC(C)COC1CS(=O)(=O)CC1OCC(C)C] | 0% | 20% |

TABLE 8-continued

| # | VENDOR | ID | STRUCTURE | INHIBITION E. coli | INHIBITION B. anthracis |
|---|---|---|---|---|---|
| 224 | CHEMDIV | 8015-2343 | 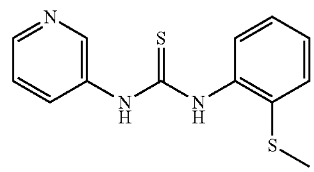 [SMILES: CSc1ccccc1NC(=S)Nc1cccnc1] | 0% | 0% |
| 225 | CHEMBRIDGE | 6154949 | 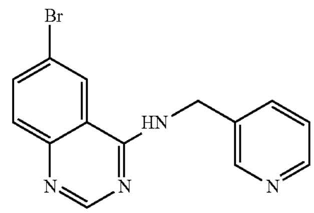 [SMILES: Brc1ccc2ncnc(NCc3cccnc3)c2c1] | 0% | 55% |
| 226 | CHEMDIV | 8009-1988 | N.A. | 0% | 0% |
| 227 | CHEMDIV | 1611-4019 | 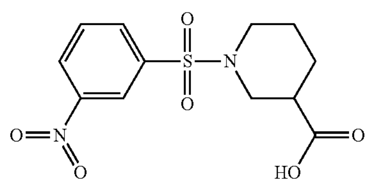 [SMILES: O=C(O)C1CCCN(S(=O)(=O)c2cccc([N+](=O)[O-])c2)C1] | 0% | 0% |
| 228 | CHEMDIV | 5330-0093 | 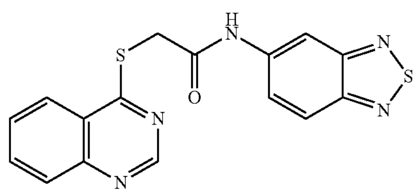 [SMILES: O=C(CSc1ncnc2ccccc12)Nc1ccc2nsnc2c1] | 0% | 28% |
| 229 | CHEMDIV | 8008-7015 | 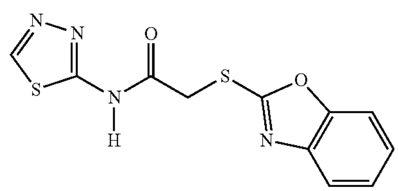 [SMILES: O=C(CSc1nc2ccccc2o1)Nc1nncs1] | 0% | 0% |
| 230 | CHEMDIV | 1218-2052 | 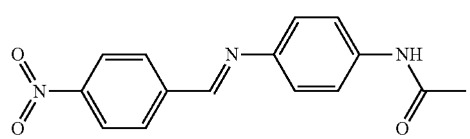 [SMILES: CC(=O)Nc1ccc(/N=C/c2ccc([N+](=O)[O-])cc2)cc1] | 0% | 0% |
| 231 | CHEMDIV | 6456-0640 | 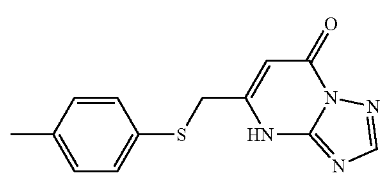 [SMILES: Cc1ccc(SCc2cc(=O)n3ncnc3[nH]2)cc1] | 0% | 0% |
| 232 | CHEMDIV | 3448-4094 | 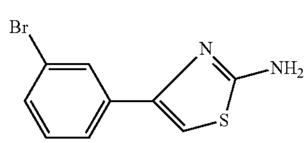 [SMILES: Nc1nc(-c2cccc(Br)c2)cs1] | 0% | 12% |

TABLE 8-continued
| # | VENDOR | ID | STRUCTURE | INHIBITION | |
|---|--------|-----|-----------|------------|---|
| | | | | E. coli | B. anthracis |
| 233 | CHEMDIV | 8013-2525 | 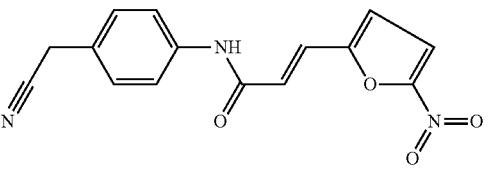 [SMILES: N#CCc1ccc(NC(=O)/C=C/c2ccc([N+](=O)[O-])o2)cc1] | 0% | 8% |
| 234 | CHEMDIV | 3616-0014 | 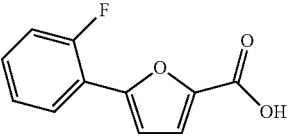 [SMILES: O=C(O)c1ccc(-c2ccccc2F)o1] | 0% | 0% |
| 235 | CHEMDIV | 7296-3325 | 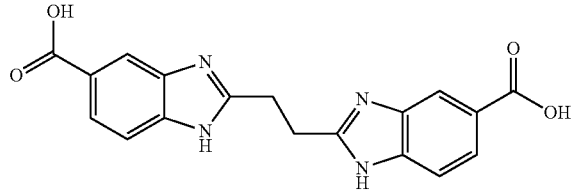 [SMILES: O=C(O)c1ccc2[nH]c(CCc3nc4cc(C(=O)O)ccc4[nH]3)nc2c1] | 0% | 0% |
| 236 | CHEMBRIDGE | 7518597 | 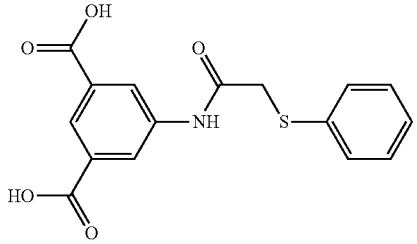 [SMILES: O=C(CSc1ccccc1)Nc1cc(C(=O)O)cc(C(=O)O)c1] | 0% | 0% |
| 237 | CHEMBRIDGE | 7942923 | 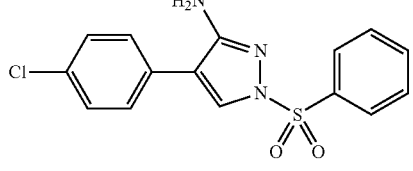 | 0% | 0% |
| 238 | CHEMDIV | 6049-1958 | 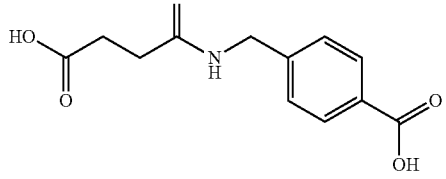 | 0% | 14% |
| 239 | CHEMDIV | 3552-0822 | 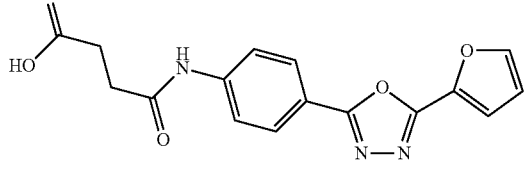 | 0% | 11% |
| 240 | CHEMDIV | 0917-0113 | 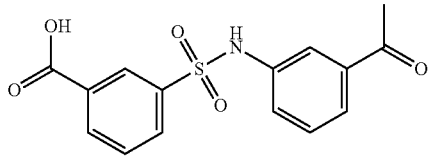 [SMILES: CC(=O)c1cccc(NS(=O)(=O)c2cccc(C(=O)O)c2)c1] | 0% | 0% |

TABLE 8-continued

| # | VENDOR | ID | STRUCTURE | INHIBITION | |
|---|---|---|---|---|---|
| | | | | E. coli | B. anthracis |
| 241 | CHEMBRIDGE | 5927580 | 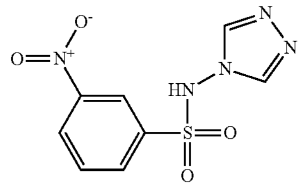 [SMILES: O=[N+]([O-])c1cccc(S(=O)(=O)Nn2cnnc2)c1] | 0% | 59% |
| 242 | CHEMDIV | 3098-0089 | 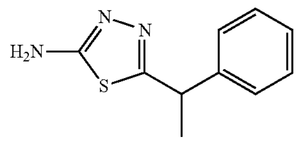 | 0% | 18% |
| 243 | CHEMDIV | C515-2290 | 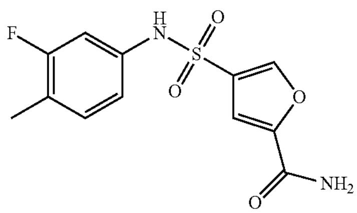 [SMILES: Cc1ccc(NS(=O)(=O)c2coc(C(N)=O)c2)cc1F] | 0% | 0% |
| 244 | SPECSNET | AN-329/ 41508710 | 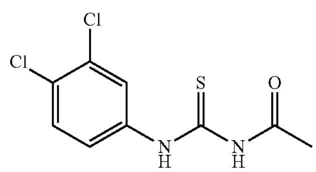 | 0% | 0% |
| 245 | CHEMBRIDGE | 7827373 | 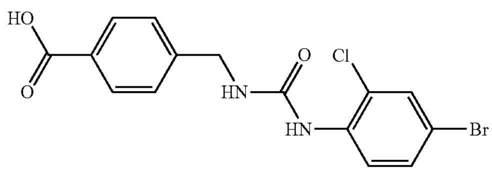 [SMILES: O=C(NCc1ccc(C(=O)O)cc1)Nc1ccc(Br)cc1Cl] | 0% | 0% |
| 246 | CHEMBRIDGE | 5321518 | 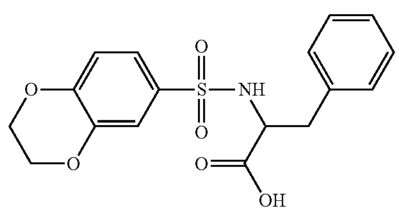 [SMILES: O=C(O)C(Cc1ccccc1)NS(=O)(=O)c1ccc2c(c1)OCCO2] | 0% | 0% |
| 247 | CHEMDIV | 4227-2396 | 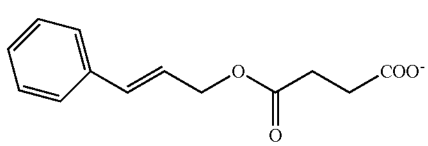 | 0% | 18% |
| 248 | CHEMDIV | 2806-0043 | 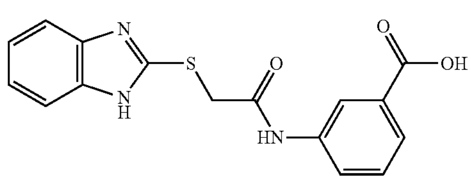 [SMILES: O=C(CSc1nc2ccccc2[nH]1)Nc1cccc(C(=O)O)c1] | 0% | 4% |

TABLE 8-continued

| # | VENDOR | ID | STRUCTURE | INHIBITION | |
|---|---|---|---|---|---|
| | | | | E. coli | B. anthracis |
| 249 | CHEMDIV | 7163-0256 | 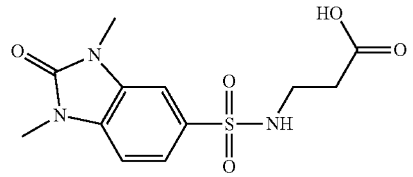 [SMILES: Cn1c(=O)n(C)c2cc(S(=O)(=O)NCCC(=O)O)ccc21] | 0% | 1% |
| 250 | CHEMDIV | 8003-6180 | 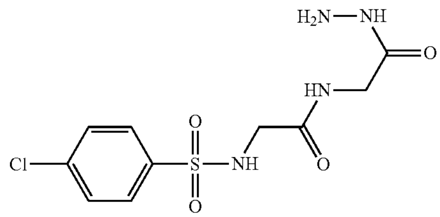 [SMILES: NNC(=O)CNC(=O)CNS(=O)(=O)c1ccc(Cl)cc1] | 0% | 0% |
| 251 | CHEMDIV | 8005-2585 | 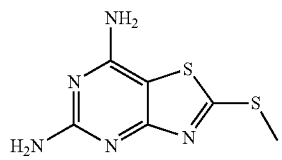 | 0% | 0% |
| 252 | CHEMDIV | 0568-0761 | 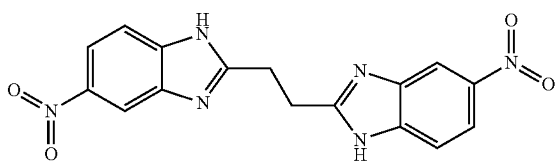 [SMILES: O=[N+]([O-])c1ccc2[nH]c(CCc3nc4cc([N+](=O)[O-])ccc4[nH]3)nc2c1] | 0% | 0% |
| 253 | CHEMDIV | 8005-8781 | 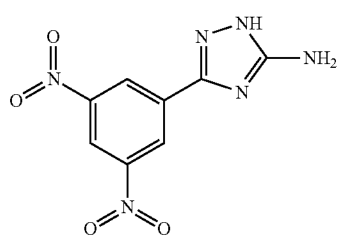 [SMILES: Nc1nc(-c2cc([N+](=O)[O-])cc([N+](=O)[O-])c2)n[nH]1] | 0% | 7% |
| 254 | SPECSNET | AO-476/43250140 | 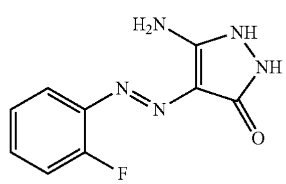 [SMILES: Nc1[nH][nH]c(=O)c1/N=N/c1ccccc1F] | 0% | 0% |
| 255 | CHEMDIV | 7199-0097 | 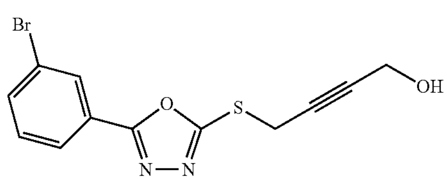 [SMILES: OCC#CCSc1nnc(-c2cccc(Br)c2)o1] | 0% | 0% |
| 256 | SPECSNET | AG-690/33357057 | 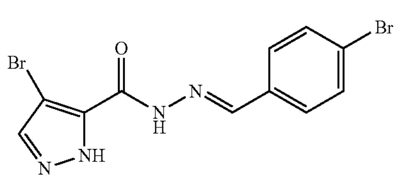 [SMILES: O=C(N/N=C/c1ccc(Br)cc1)c1[nH]ncc1Br] | 0% | 0% |

TABLE 8-continued

| # | VENDOR | ID | STRUCTURE | INHIBITION E. coli | INHIBITION B. anthracis |
|---|---|---|---|---|---|
| 257 | SPECSNET | AN-979/ 15013099 | N.A. | 0% | 36% |
| 258 | CHEMDIV | 8015-1564 | (structure) | 0% | 0% |
| 259 | CHEMDIV | 6114-0555 | (structure) | 0% | 0% |
| 260 | CHEMDIV | 8012-5863 | (structure) | 0% | 0% |
| 261 | CHEMDIV | 5297-0273 | (structure) | 0% | 24% |
| 262 | CHEMDIV | 2418-0562 | (structure) | 0% | 5% |
| 263 | CHEMDIV | 8010-8281 | (structure) | 0% | 0% |
| 264 | SPECSNET | AG-690/ 11635562 | (structure) | 0% | 0% |

… continued

TABLE 8-continued

| # | VENDOR | ID | STRUCTURE | INHIBITION E. coli | INHIBITION B. anthracis |
|---|---|---|---|---|---|
| 265 | CHEMDIV | C324-1252 | 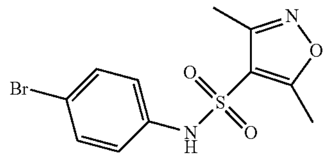 [SMILES: Cc1noc(C)c1S(=O)(=O)Nc1ccc(Br)cc1] | 0% | 4% |
| 266 | CHEMDIV | 0801-1033 | N.A. | 0% | 0% |
| 267 | CHEMDIV | 4896-3402 | 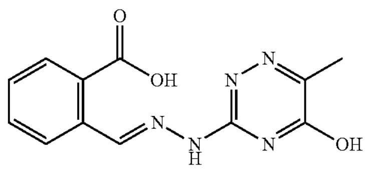 [SMILES: Cc1nnc(N/N=C/c2ccccc2C(=O)O)nc1O] | 0% | 4% |
| 268 | CHEMBRIDGE | 5469050 | 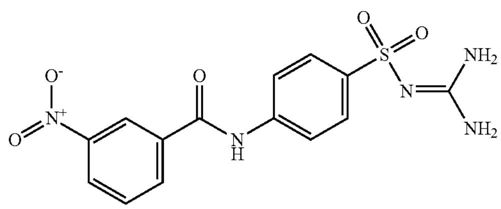 [SMILES: NC(N)=NS(=O)(=O)c1ccc(NC(=O)c2cccc([N+](=O)[O-])c2)cc1] | 0% | 0% |
| 269 | CHEMBRIDGE | 6676515 | 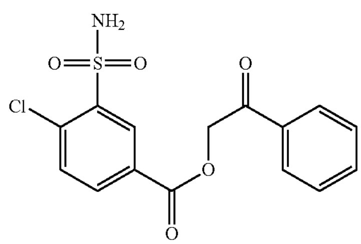 [SMILES: NS(=O)(=O)c1cc(C(=O)OCC(=O)c2ccccc2)ccc1Cl] | 0% | 22% |
| 270 | CHEMDIV | 3973-0479 | 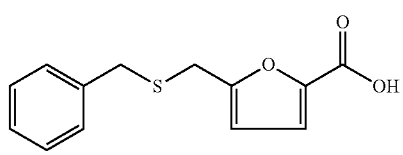 [SMILES: O=C(O)c1ccc(CSCc2ccccc2)o1] | 0% | 21% |
| 271 | CHEMDIV | C614-1037 | 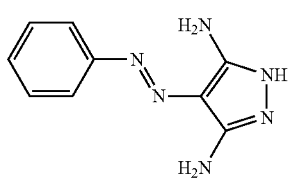 [SMILES: Nc1n[nH]c(N)c1/N=N/c1ccccc1] | 0% | n.d. |
| 272 | CHEMBRIDGE | 6615918 | 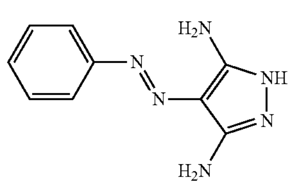 [SMILES: Nc1n[nH]c(N)c1/N=N/c1ccccc1] | 0% | 23% |
| 273 | CHEMDIV | 0242-0575 | N.A. | 0% | 0% |

TABLE 8-continued

| # | VENDOR | ID | STRUCTURE | INHIBITION | |
|---|---|---|---|---|---|
| | | | | E. coli | B. anthracis |
| 274 | CHEMDIV | 1482-0215 | 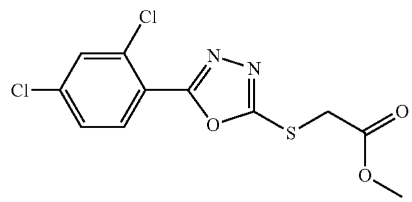 [SMILES: COC(=O)CSc1nnc(-c2ccc(Cl)cc2Cl)o1] | 0% | 0% |
| 275 | SPECSNET | AH-034/ 32472056 | 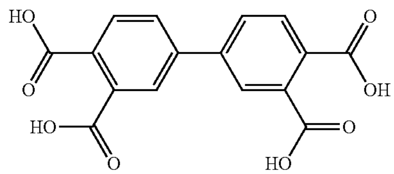 [SMILES: O=C(O)c1ccc(-c2ccc(C(=O)O)c(C(=O)O)c2)cc1C(=O)O] | 0% | 0% |
| 276 | CHEMDIV | C224-3335 | N.A. | 0% | 7% |
| 277 | CHEMDIV | 7177-0015 | 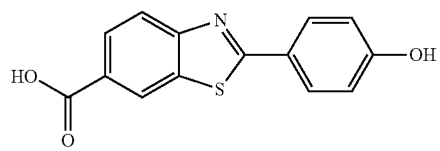 [SMILES: O=C(O)c1ccc2nc(-c3ccc(O)cc3)sc2c1] | 0% | 0% |
| 278 | CHEMDIV | 0144-0010 | 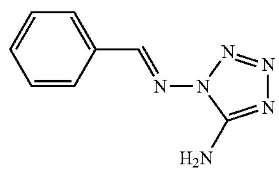 [SMILES: Nc1nnnn1/N=C/c1ccccc1] | 0% | 0% |
| 279 | CHEMDIV | 0703-6430 | 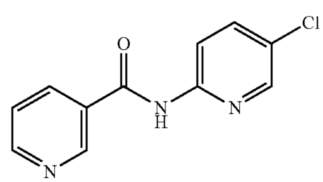 [SMILES: O=C(Nc1ccc(Cl)cn1)c1cccnc1] | 0% | 0% |
| 280 | SPECSNET | AN-988/ 40787809 | 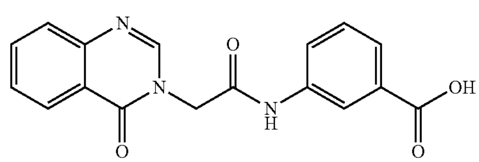 [SMILES: O=C(Cn1cnc2ccccc2c1=O)Nc1cccc(C(=O)O)c1] | 0% | 0% |
| 281 | CHEMDIV | 0368-0073 | N.A. | 0% | 0% |
| 282 | CHEMDIV | 0422-0031 | N.A. | 0% | 0% |
| 283 | SPECSNET | AN-329/ 40038407 | 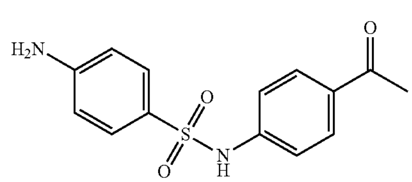 [SMILES: CC(=O)c1ccc(NS(=O)(=O)c2ccc(N)cc2)cc1] | 0% | 0% |
| 284 | CHEMDIV | C206-0915 | 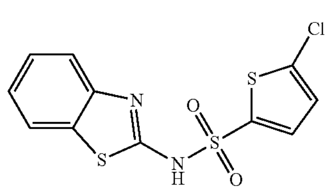 [SMILES: O=S(=O)(Nc1nc2ccccc2s1)c1ccc(Cl)s1] | 0% | 7% |

TABLE 8-continued

| # | VENDOR | ID | STRUCTURE | INHIBITION | |
|---|---|---|---|---|---|
| | | | | E. coli | B. anthracis |
| 285 | CHEMDIV | C224-4321 | 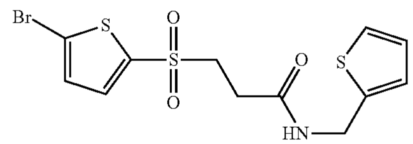 [SMILES: O=C(CCS(=O)(=O)c1ccc(Br)s1)NCc1cccs1] | 0% | n.d |
| 286 | SPECSNET | AG-690/ 40753590 | 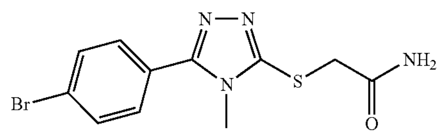 [SMILES: Cn1c(SCC(N)=O)nnc1-c1ccc(Br)cc1] | 0% | 0% |
| 287 | SPECSNET | AM-807/ 13614710 | 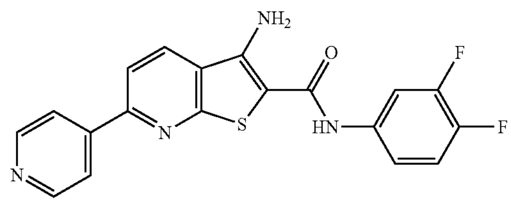 [SMILES: Nc1c(C(=O)Nc2ccc(F)c(F)c2)sc2nc(-c3ccncc3)ccc12] | 0% | 0% |
| 288 | CHEMBRIDGE | 5543949 | 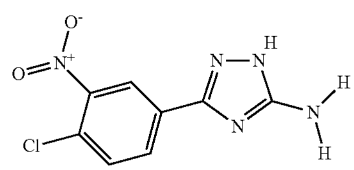 | 0% | 0% |
| 289 | CHEMDIV | C224-2785 | 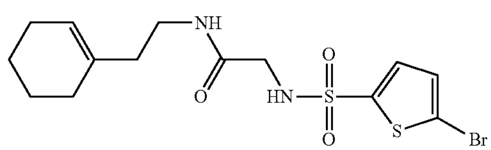 [SMILES: O=C(CNS(=O)(=O)c1ccc(Br)s1)NCCC1=CCCCC1] | 0% | 4% |
| 290 | CHEMBRIDGE | 7905975 | 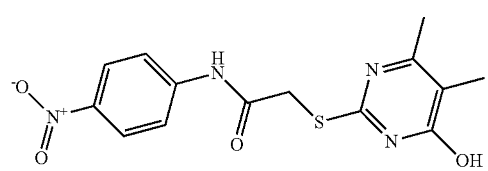 | 0% | 2% |
| 291 | CHEMDIV | 1813-1087 | 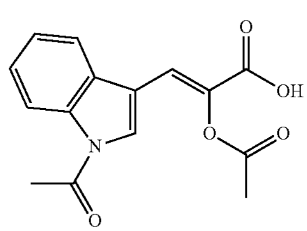 [SMILES: CC(=O)O/C(=C\c1cn(C(C)=O)c2ccccc12)C(=O)O] | 0% | 0% |
| 292 | CHEMDIV | 4694-0709 | 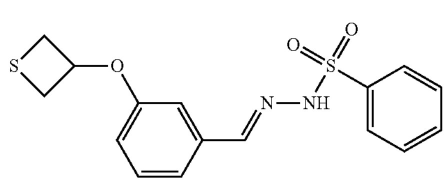 [SMILES: O=S(=O)(N/N=C/c1cccc(OC2CSC2)c1)c1ccccc1] | 0% | 0% |

TABLE 8-continued
| # | VENDOR | ID | STRUCTURE | INHIBITION | |
|---|---|---|---|---|---|
| | | | | E. coli | B. anthracis |
| 293 | CHEMBRIDGE | 5210723 | 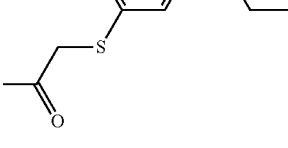 | 0% | 5% |
| 294 | SPECSNET | AG-670/ 09238023 | 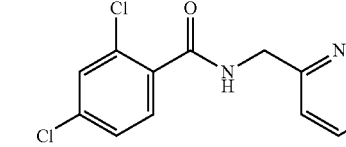 | 0% | 0% |
| 295 | SPECSNET | AG-670/ 34456007 | 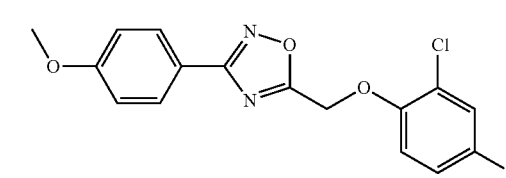 | 0% | 11% |
| 296 | CHEMBRIDGE | 5551093 | 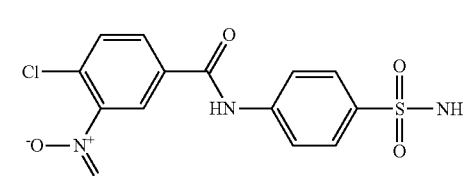 | 0% | 0% |
| 297 | CHEMDIV | C206-0874 | 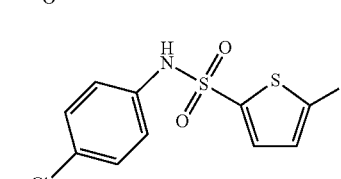 | 0% | 0% |
| 298 | SPECSNET | AG-690/ 40701147 | 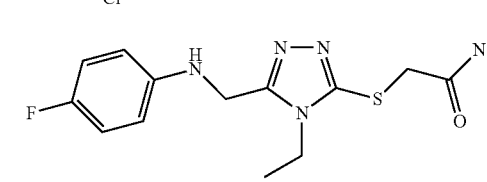 | 0% | 0% |
| 299 | CHEMDIV | 4951-1209 | 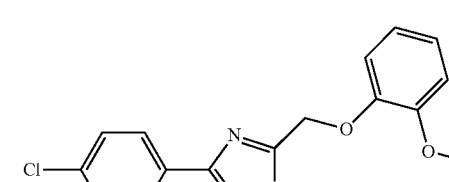 | 0% | 1% |
| 300 | SPECSNET | AN-329/ 11215878 | 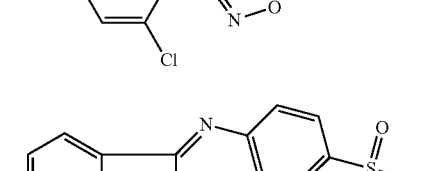 | 0% | 0% |

TABLE 8-continued
| # | VENDOR | ID | STRUCTURE | INHIBITION | |
|---|--------|-----|-----------|------------|---|
| | | | | E. coli | B. anthracis |
| 301 | CHEMDIV | C226-0504 | 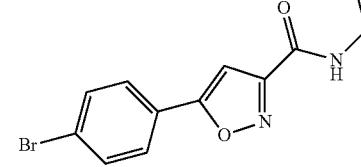 | 0% | 0% |
| 302 | SPECSNET | AG-690/ 11667663 | 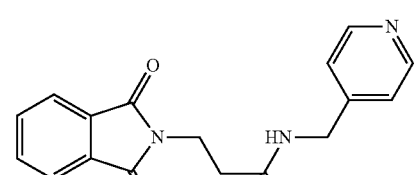 | 0% | 0% |
| 303 | SPECSNET | AE-848/ 33221011 | 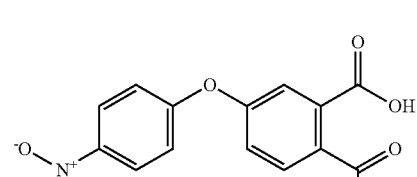 | 0% | 0% |
| 304 | SPECSNET | AN-329/ 41189553 | 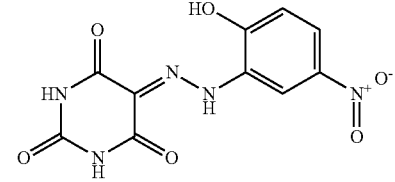 | 0% | 0% |
| 305 | SPECSNET | AK-968/ 12100046 | 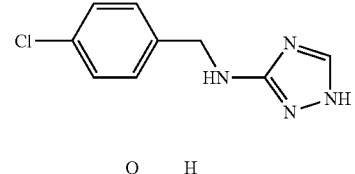 | 0% | 0% |
| 306 | SPECSNET | AN-652/ 41309302 | 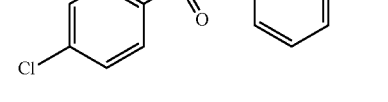 | 0% | 0% |
| 307 | SPECSNET | AO-081/ 41756354 | 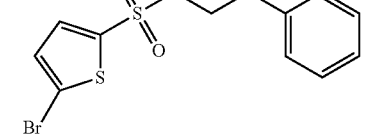 | 0% | 0% |

TABLE 9
| # | VENDOR | ID | STRUCTURE | INHIBITION (%) IC$_{50}$ (μM) | |
|---|---|---|---|---|---|
| | | | | *E. coli* | *B. anthracis* |
| 003 | SPECS | AM-807/ 13614404 (C11) | 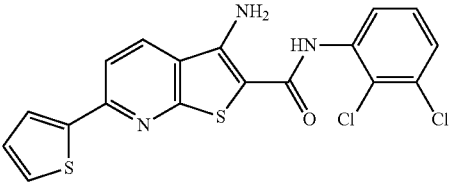 [SMILES: Nc1c(C(=O)Nc2cccc(Cl)c2Cl)sc2nc(-c3cccs3)ccc12] | 73% | 40% |
| 03_01 | CHEMDIV | 5350-0377 | 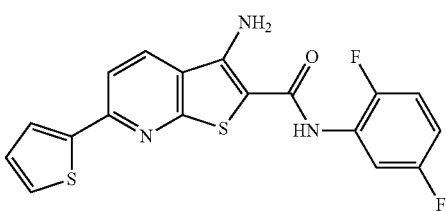 | 100% 25 | 100% 25 |
| 03_02 | CHEMDIV | 5350-0029 | 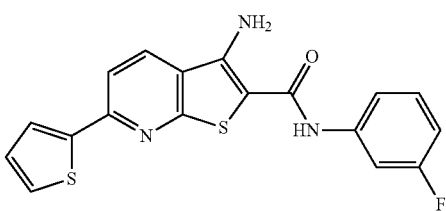 [SMILES: Nc1c(C(=O)Nc2cccc(F)c2)sc2nc(-c3cccs3)ccc12] | 98% 65 | 100% 36 |
| 03_03 | SPECS | AM-807/ 13614405 | 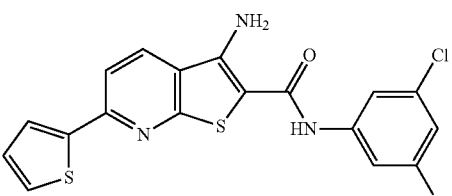 | 93% 64 | 90% 21 |
| 03_04 | SPECS | AM-807/ 3614701 | 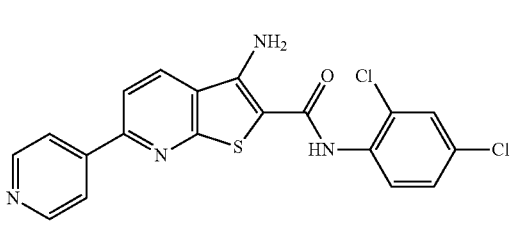 [SMILES: Nc1c(C(=O)Nc2ccc(Cl)cc2Cl)sc2nc(-c3ccncc3)ccc12] | 84% 21 | 79% 21 |
| 03_05 | SPECS | AM-807/ 13614315 | 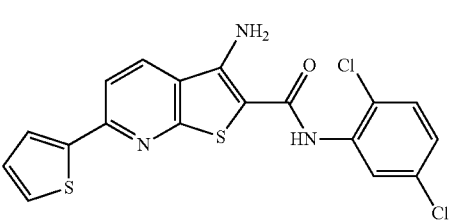 | 81% 20 | 90% 9 |
| 03_06 | SPECS | AM-807/ 13614765 | 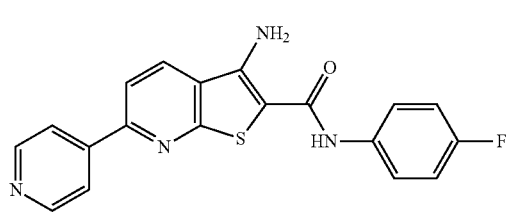 [SMILES: Nc1c(C(=O)Nc2ccc(F)cc2)sc2nc(-c3ccncc3)ccc12] | 80% >200 | 40% >200 |

TABLE 9-continued
| # | VENDOR | ID | STRUCTURE | INHIBITION (%) IC$_{50}$ (µM) | |
|---|---|---|---|---|---|
| | | | | *E. coli* | *B. anthracis* |
| 03_07 | CHEMDIV | 5350-0378 | 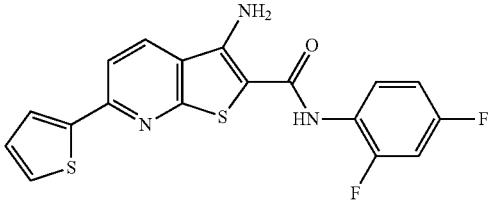 [SMILES: Nc1c(C(=O)Nc2ccc(F)cc2F)sc2nc(-c3cccs3)ccc12] | 69%<br>44 | 83%<br>18 |
| 03_08 | SPECS | AM-807/<br>13615709 | 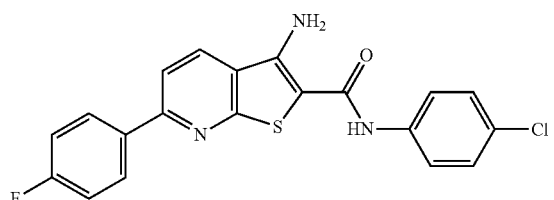 | 68%<br>>200 | 28%<br>>200 |
| 03_09 | CHEMBRIDGE | 7122170 | 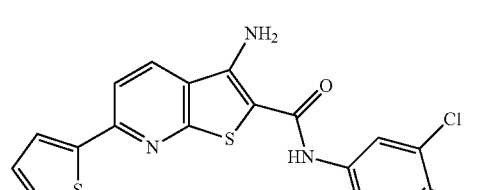 | 60% | 63% |
| 03_10 | SPECS | AM-807/<br>12740168 | 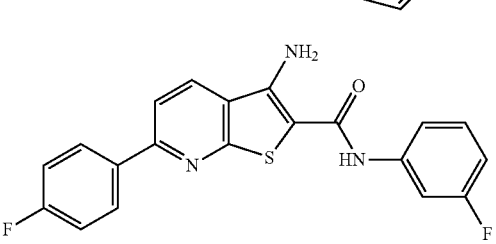 | 56% | 60% |
| 03_11 | SPECS | AM-807/<br>13614318 | 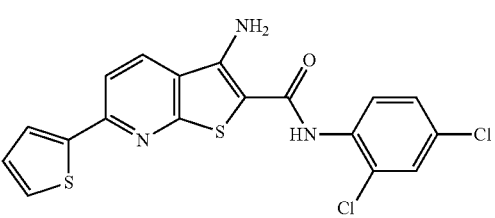 [SMILES: Nc1c(C(=O)Nc2ccc(Cl)cc2Cl)sc2nc(-c3cccs3)ccc12] | 54%<br>30 | 90%<br>13 |
| 03_12 | SPECS | AM-807/<br>13614391 | 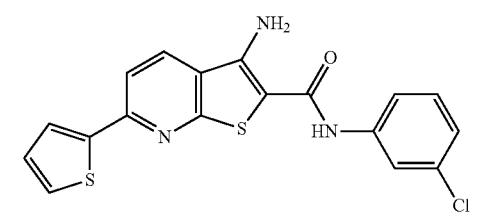 [SMILES: Nc1c(C(=O)Nc2cccc(Cl)c2)sc2nc(-c3cccs3)ccc12] | 53%<br>71 | 89%<br>15 |
| 03_13 | SPECS | AM-807/<br>13615660 | 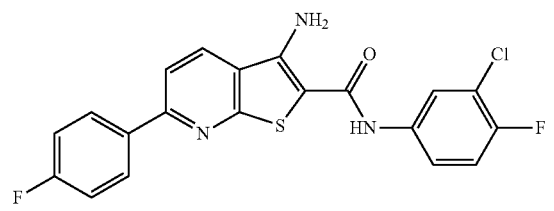 [SMILES: Nc1c(C(=O)Nc2ccc(F)c(Cl)c2)sc2nc(-c3ccc(F)cc3)ccc12] | 52% | 26% |

TABLE 9-continued

| # | VENDOR | ID | STRUCTURE | INHIBITION (%) IC$_{50}$ (μM) | |
|---|---|---|---|---|---|
| | | | | *E. coli* | *B. anthracis* |
| 03_14 | CHEMDIV | 5350-0016 | 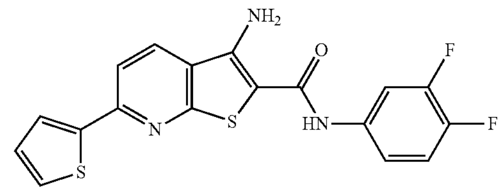 [SMILES: Nc1c(C(=O)Nc2ccc(F)c(F)c2)sc2nc(-c3cccs3)ccc12] | 46% 117 | 92% 38 |
| 03_15 | SPECS | AM-807/ 13614362 | 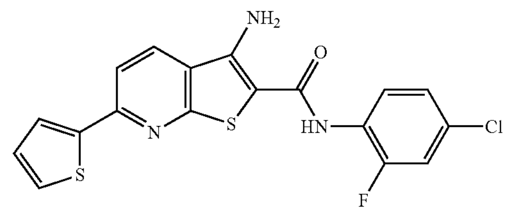 [SMILES: Nc1c(C(=O)Nc2ccc(Cl)cc2F)sc2nc(-c3cccs3)ccc12] | 46% 51 | 87% 12 |
| 03_16 | SPECS | AM-807/ 13615708 | 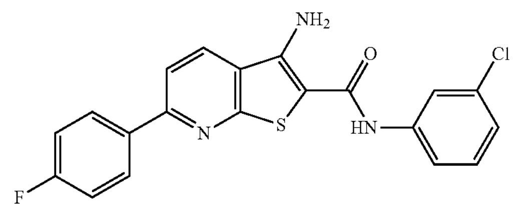 [SMILES: Nc1c(C(=O)Nc2cccc(Cl)c2)sc2nc(-c3ccc(F)cc3)ccc12] | 46% 50 | 83% 35 |
| 03_17 | SPECS | AM-807/ 13614744 | 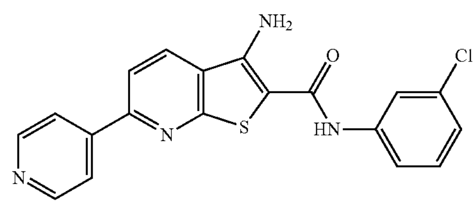 [SMILES: Nc1c(C(=O)Nc2cccc(Cl)c2)sc2nc(-c3ccncc3)ccc12] | 44% | 64% |
| 03_18 | SPECS | AM-807/ 13614342 | 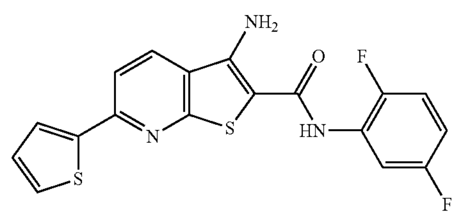 [SMILES: Nc1c(C(=O)Nc2cc(F)ccc2F)sc2nc(-c3cccs3)ccc12] | 41% 35 | 71% 14 |
| 03_19 | SPECS | AM-807/ 13615674 | 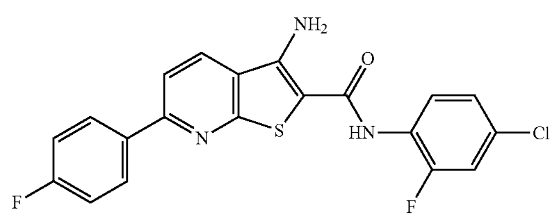 [SMILES: Nc1c(C(=O)Nc2ccc(Cl)cc2F)sc2nc(-c3ccc(F)cc3)ccc12] | 32% | 61% |
| 03_20 | SPECS | AM-807/ 14147089 | 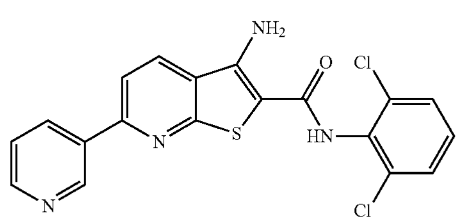 [SMILES: Nc1c(C(=O)Nc2c(Cl)cccc2Cl)sc2nc(-c3cccnc3)ccc12] | 24% >200 | 11% >200 |

TABLE 9-continued

| # | VENDOR | ID | STRUCTURE | INHIBITION (%) IC$_{50}$ (µM) | |
|---|---|---|---|---|---|
| | | | | *E. coli* | *B. anthracis* |
| 03_21 | CHEMBRIDGE | 7904181 | 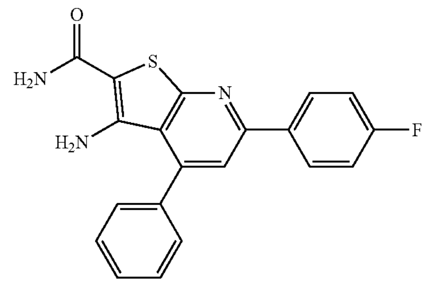 [SMILES: NC(=O)c1sc2nc(-c3ccc(F)cc3)cc(-c3ccccc3)c2c1N] | 22% | 58% |
| 03_22 | SPECS | AM-807/ 13614667 | 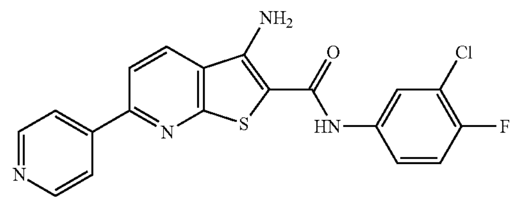 [SMILES: Nc1c(C(=O)Nc2ccc(F)c(Cl)c2)sc2nc(-c3ccncc3)ccc12] | 21% 100 | 83% 39 |
| 03_23 | SPECS | AM-807/ 13615675 | 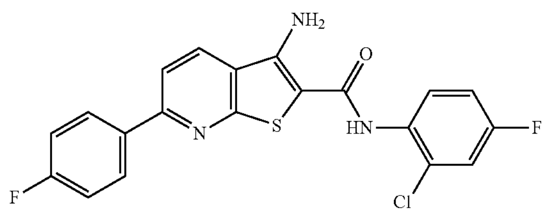 [SMILES: Nc1c(C(=O)Nc2ccc(F)cc2Cl)sc2nc(-c3ccc(F)cc3)ccc12] | 20% >200 | 75% 63 |
| 03_24 | SPECS | AM-807/ 13615668 | 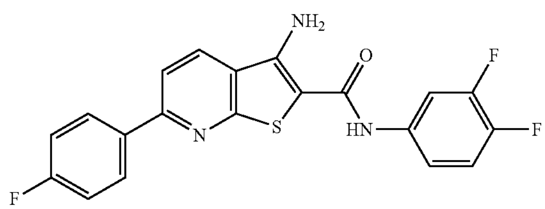 [SMILES: Nc1c(C(=O)Nc2ccc(F)c(F)c2)sc2nc(-c3ccc(F)cc3)ccc12] | 9% >200 | 5% >200 |
| 03_25 | SPECS | AM-807/ 12740165 | 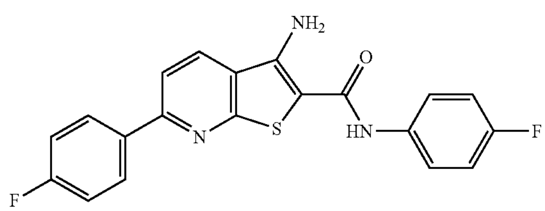 [SMILES: Nc1c(C(=O)Nc2ccc(F)cc2)sc2nc(-c3ccc(F)cc3)ccc12] | 8% | 1% |
| 03_26 | CHEMDIV | 5350-0047 | 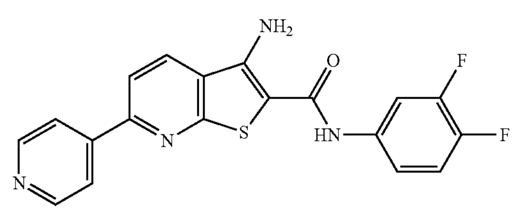 [SMILES: Nc1c(C(=O)Nc2ccc(F)c(F)c2)sc2nc(-c3ccncc3)ccc12] | 7% | 23% |
| 03_27 | SPECS | AM-807/ 13614751 | 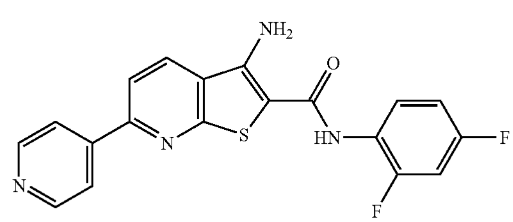 [SMILES: Nc1c(C(=O)Nc2ccc(F)cc2F)sc2nc(-c3ccncc3)ccc12] | 0% | 20% |

TABLE 9-continued

| # | VENDOR | ID | STRUCTURE | INHIBITION (%) IC$_{50}$ (µM) | |
|---|---|---|---|---|---|
| | | | | *E. coli* | *B. anthracis* |
| 03_28 | SPECS | AM-807/ 13614758 | 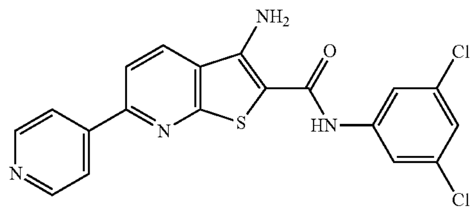 [SMILES: Nc1c(C(=O)Nc2cc(Cl)cc(Cl)c2)sc2nc(-c3ccncc3)ccc12] | 0% | 0% |
| 03_29 | SPECS | AM-807/ 13614745 | 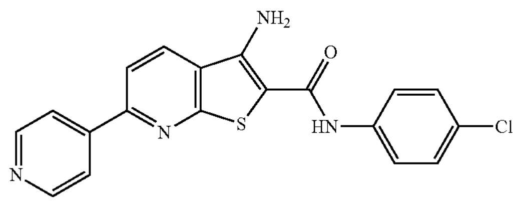 [SMILES: Nc1c(C(=O)Nc2ccc(Cl)cc2)sc2nc(-c3ccncc3)ccc12] | 0% | 0% |
| 001 | SPECSNET | AG-205/ 32429038 (X10) | 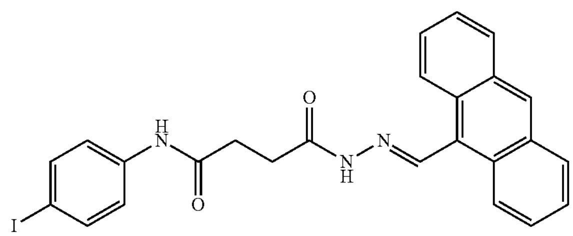 [SMILES: O=C(CCC(=O)Nc1ccc(I)cc1)N/N=C/c1c2ccccc2cc2ccccc12] | 79% 15 | 88% 21 |
| 01_01 | CHEMDIV | 8005-4955 | 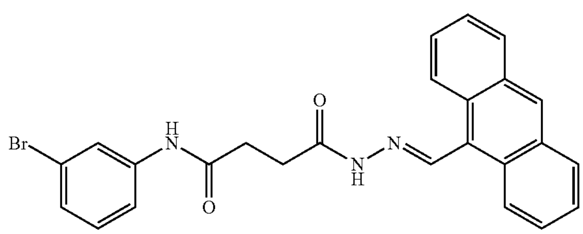 [SMILES: O=C(CCC(=O)Nc1cccc(Br)c1)N/N=C/c1c2ccccc2cc2ccccc12] | 90% 6 | 81% 4 |
| 01_02 | CHEMDIV | 8003-9695 | 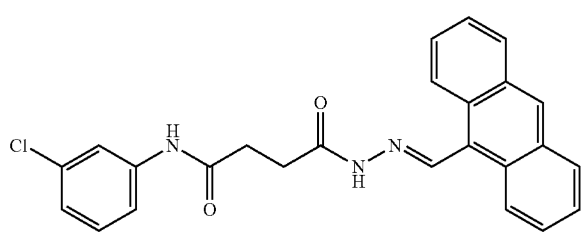 [SMILES: O=C(CCC(=O)Nc1cccc(Cl)c1)N/N=C/c1c2ccccc2cc2ccccc12] | 80% 15 | 101% 25 |
| 01_03 | CHEMDIV | 8003-6329 | 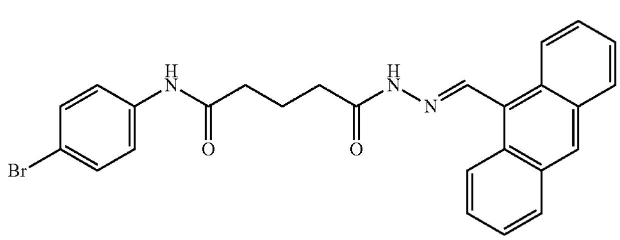 [SMILES: O=C(CCCC(=O)Nc1ccc(Br)cc1)N/N=C/c1c2ccccc2cc2ccccc12] | 80% 18 | 97% 33 |

TABLE 9-continued

| # | VENDOR | ID | STRUCTURE | INHIBITION (%) IC$_{50}$ (μM) | |
|---|---|---|---|---|---|
| | | | | *E. coli* | *B. anthracis* |
| 01_04 | CHEMDIV | 8003-8850 | 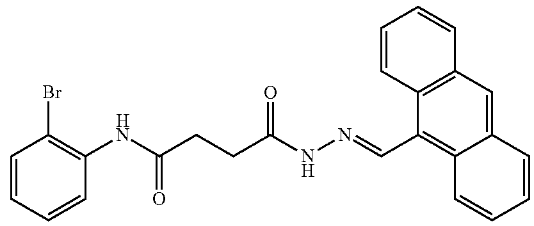 [SMILES: O=C(CCC(=O)Nc1ccccc1Br)N/N=C/c1c2ccccc2cc2ccccc12] | 79% 15 | 100% 25 |
| 01_05 | CHEMBRIDGE | 6048997 | 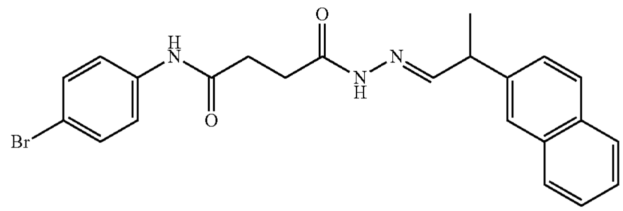 [SMILES: CC(/C=N/NC(=O)CCC(=O)Nc1ccc(Br)cc1)c1ccc2ccccc2c1] | 78% 88 | 76% >200 |
| 01_06 | CHEMDIV | 1761-1053 | 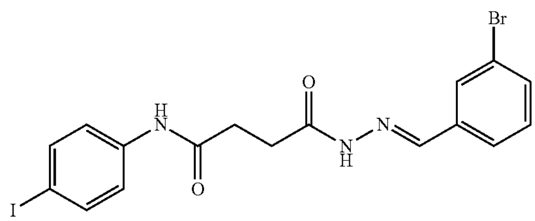 [SMILES: O=C(CCC(=O)Nc1ccc(I)cc1)N/N=C/c1cccc(Br)c1] | 78% | 54% |
| 01_07 | CHEMDIV | 1761-1076 | 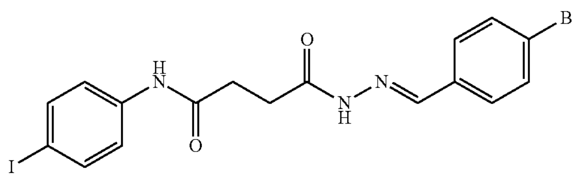 | 77% | 81% |
| 01_08 | CHEMDIV | 1761-0662 | 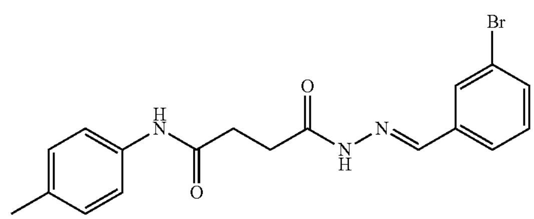 [SMILES: Cc1ccc(NC(=O)CCC(=O)N/N=C/c2cccc(Br)c2)cc1] | 75% | 74% |
| 01_09 | CHEMDIV | 1761-0639 | 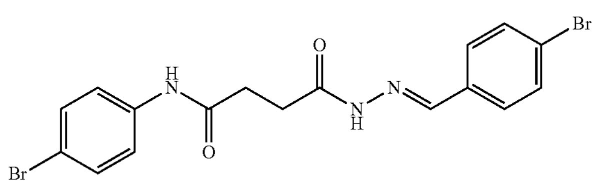 [SMILES: O=C(CCC(=O)Nc1ccc(Br)cc1)N/N=C/c1ccc(Br)cc1] | 74% | 68% |
| 01_10 | CHEMDIV | 8006-3094 | 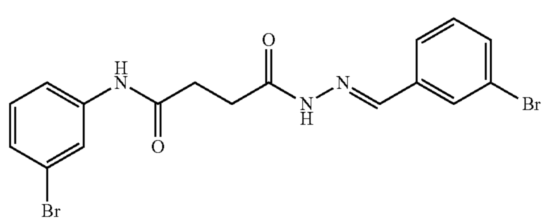 [SMILES: O=C(CCC(=O)Nc1cccc(Br)c1)N/N=C/c1cccc(Br)c1] | 72% | 53% |

TABLE 9-continued

| # | VENDOR | ID | STRUCTURE | INHIBITION (%) IC$_{50}$ (µM) | |
|---|--------|-----|-----------|---------|---------|
| | | | | E. coli | B. anthracis |
| 01_11 | CHEMDIV | 1761-0064 | 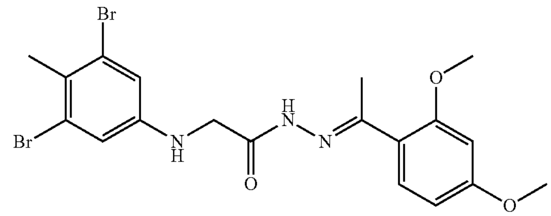 [SMILES: COc1ccc(/C(C)=N/NC(=O)CNc2cc(Br)c(C)c(Br)c2)c(OC)c1] | 70% — | 86% 30 |
| 01_12 | CHEMDIV | 1761-0644 | 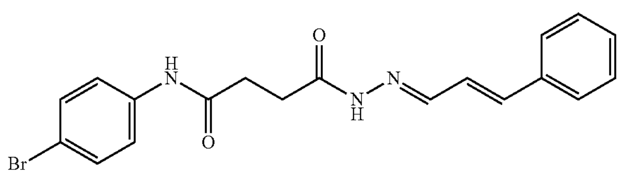 [SMILES: O=C(CCC(=O)Nc1ccc(Br)cc1)N/N=C/C=C/c1ccccc1] | 68% — | 75% 48 |
| 01_13 | CHEMDIV | 1761-0615 | 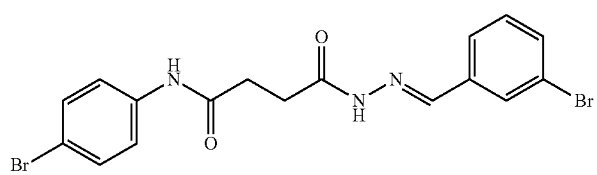 [SMILES: O=C(CCC(=O)Nc1ccc(Br)cc1)N/N=C/c1cccc(Br)c1] | 67% — | 29% 170 |
| 01_14 | CHEMDIV | 1761-0686 | 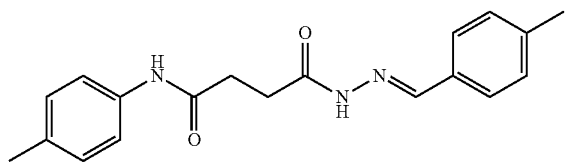 | 60% | 70% |
| 01_15 | CHEMDIV | 1761-0634 | 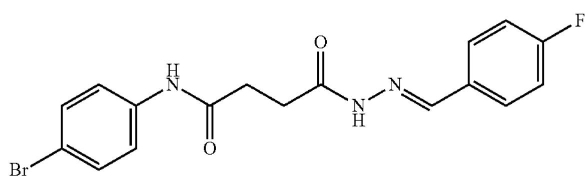 [SMILES: O=C(CCC(=O)Nc1ccc(Br)cc1)N/N=C/c1ccc(F)cc1] | 47% — | 22% 122 |
| 01_16 | CHEMDIV | 1761-0591 | 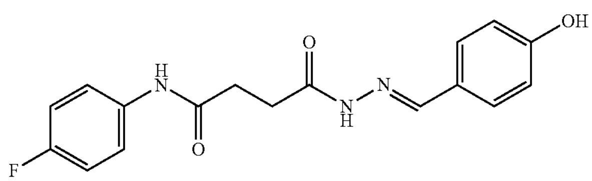 [SMILES: O=C(CCC(=O)Nc1ccc(F)cc1)N/N=C/c1ccc(O)cc1] | 42% | 29% |
| 01_17 | CHEMDIV | 8005-4949 | 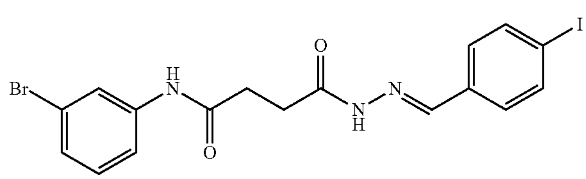 [SMILES: O=C(CCC(=O)Nc1cccc(Br)c1)N/N=C/c1ccc(I)cc1] | 41% | 35% |
| 01_18 | CHEMDIV | 1761-0651 | 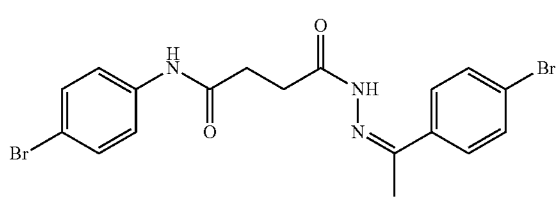 [SMILES: C/C(=N/NC(=O)CCC(=O)Nc1ccc(Br)cc1)c1ccc(Br)cc1] | 38% | 49% |

TABLE 9-continued
| # | VENDOR | ID | STRUCTURE | INHIBITION (%) IC$_{50}$ (μM) | |
|---|---|---|---|---|---|
| | | | | E. coli | B. anthracis |
| 015 | CHEMDIV | C285-0040 (12B) | 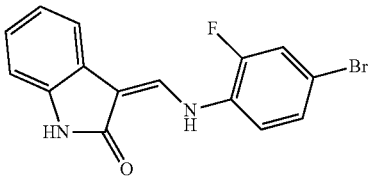 [SMILES: O=C1Nc2ccccc2/C1=C/Nc1ccc(Br)cc1F] | 29% 30 | 57% 16 |
| 15_01 | CHEMDIV | C285-0041 | 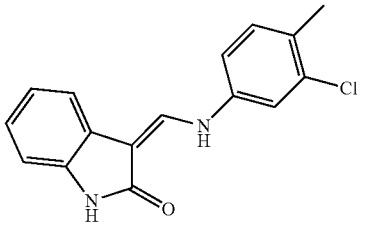 [SMILES: Cc1ccc(N/C=C2\C(=O)Nc3ccccc32)cc1Cl] | 24% >200 | 37% >200 |
| 15_02 | CHEMDIV | C285-0043 | 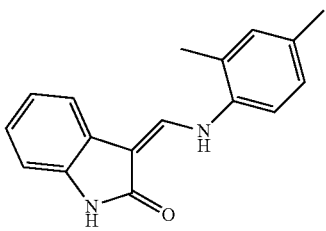 [SMILES: Cc1ccc(N/C=C2\C(=O)Nc3ccccc32)c(C)c1] | 20% | 29% |
| 15_03 | CHEMDIV | C285-0110 | 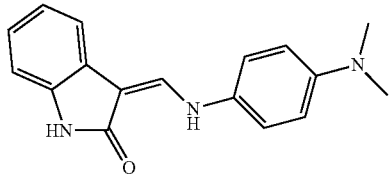 [SMILES: CN(C)c1ccc(N/C=C2\C(=O)Nc3ccccc32)cc1] | 19% | 27% |
| 15_04 | CHEMDIV | C285-0042 | 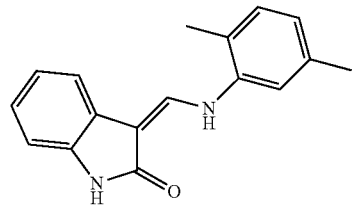 [SMILES: Cc1ccc(C)c(N/C=C2\C(=O)Nc3ccccc32)c1] | 18% | 26% |
| 15_05 | CHEMDIV | C285-0047 | 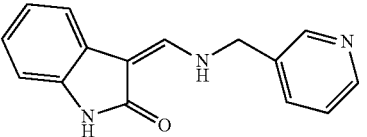 [SMILES: O=C1Nc2ccccc2/C1=C/NCc1cccnc1] | 17% | 23% |
| 15_06 | CHEMDIV | C285-0025 | 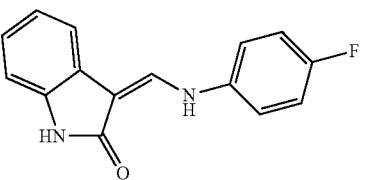 [SMILES: O=C1Nc2ccccc2/C1=C/Nc1ccc(F)cc1] | 15% | 49% |

TABLE 9-continued

| # | VENDOR | ID | STRUCTURE | INHIBITION (%) IC$_{50}$ (µM) E. coli | B. anthracis |
|---|---|---|---|---|---|
| 15_07 | CHEMDIV | 5682-0155 | 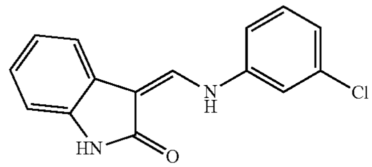 [SMILES: O=C1Nc2ccccc2/C1=C/Nc1cccc(Cl)c1] | 15% | 45% |
| 15_08 | CHEMDIV | C285-0037 | 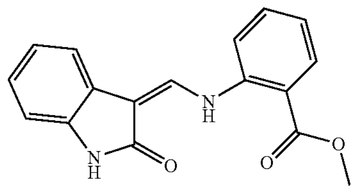 [SMILES: COC(=O)c1ccccc1N/C=C1\C(=O)Nc2ccccc21] | 14% | 0% |
| 15_09 | CHEMDIV | C285-0027 | 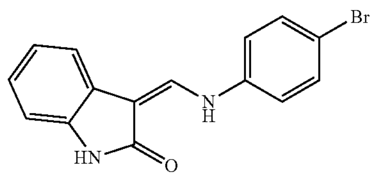 [SMILES: O=C1Nc2ccccc2/C1=C/Nc1ccc(Br)cc1] | 13%<br>>200 | 60%<br>111 |
| 15_10 | CHEMDIV | 5682-0153 | 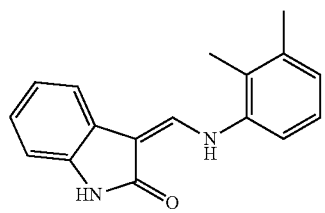 [SMILES: Cc1cccc(N/C=C2\C(=O)Nc3ccccc32)c1C] | 13% | 26% |
| 15_11 | CHEMDIV | C285-0115 | 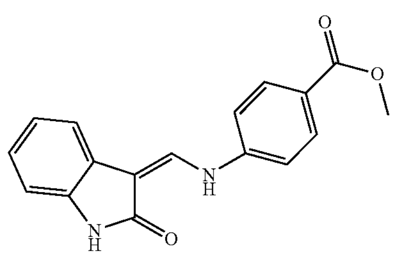 [SMILES: COC(=O)c1ccc(N/C=C2\C(=O)Nc3ccccc32)cc1] | 12%<br>191 | 63%<br>98 |
| 15_12 | CHEMDIV | 5682-0015 | 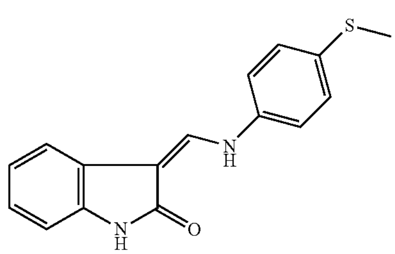 [SMILES: CSc1ccc(N/C=C2\C(=O)Nc3ccccc32)cc1] | 12% | 25% |
| 15_13 | CHEMDIV | C285-0028 | 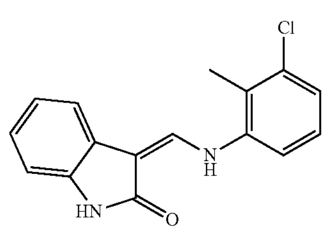 [SMILES: Cc1c(Cl)cccc1N/C=C1\C(=O)Nc2ccccc21] | 12% | 36% |

TABLE 9-continued

| # | VENDOR | ID | STRUCTURE | INHIBITION (%) IC$_{50}$ (μM) | |
|---|---|---|---|---|---|
| | | | | *E. coli* | *B. anthracis* |
| 15_14 | CHEMDIV | C285-0069 | 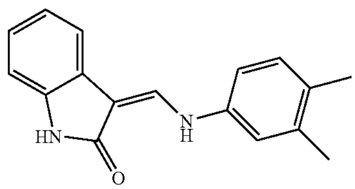 [SMILES: Cc1ccc(N/C=C2\C(=O)Nc3ccccc32)cc1C] | 12%<br>88 | 70%<br>74 |
| 15_15 | CHEMDIV | 5682-0145 | 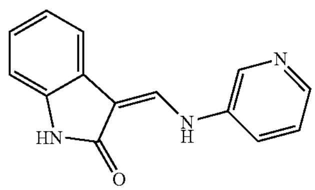 [SMILES: O=C1Nc2ccccc2/C1=C/Nc1cccnc1] | 12% | 10% |
| 15_16 | CHEMDIV | 5682-0013 | 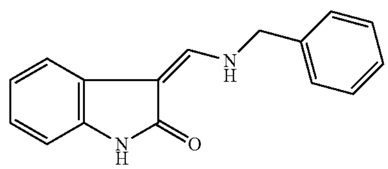 [SMILES: O=C1Nc2ccccc2/C1=C/NCc1ccccc1] | 11% | 6% |
| 15_17 | CHEMDIV | C285-0024 | 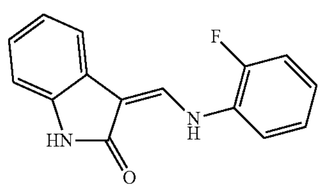 [SMILES: O=C1Nc2ccccc2/C1=C/Nc1ccccc1F] | 11% | 22% |
| 15_18 | CHEMDIV | C285-0073 | 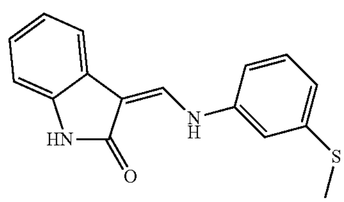 [SMILES: CSc1cccc(N/C=C2\C(=O)Nc3ccccc32)c1] | 11% | 24% |
| 15_19 | CHEMDIV | C285-0033 | 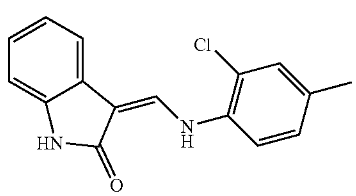 [SMILES: Cc1ccc(N/C=C2\C(=O)Nc3ccccc32)c(Cl)c1] | 11% | 14% |
| 15_20 | CHEMDIV | 5682-0012 | 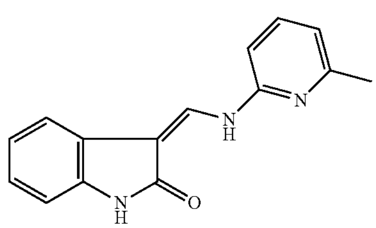 [SMILES: Cc1cccc(N/C=C2\C(=O)Nc3ccccc32)n1] | 11% | 8% |

TABLE 9-continued

| # | VENDOR | ID | STRUCTURE | INHIBITION (%) IC$_{50}$ (μM) | |
|---|---|---|---|---|---|
| | | | | E. coli | B. anthracis |
| 15_21 | CHEMDIV | C285-0070 | 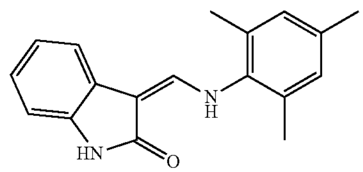 [SMILES: Cc1cc(C)c(N/C=C2\C(=O)Nc3ccccc32)c(C)c1] | 10% | 30% |
| 15_22 | CHEMDIV | 5682-0157 | 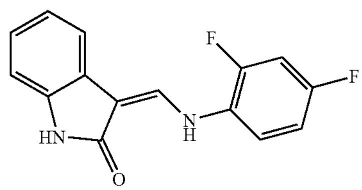 [SMILES: O=C1Nc2ccccc2/C1=C/Nc1ccc(F)cc1F] | 10% | 28% |
| 15_23 | CHEMDIV | C285-0071 | 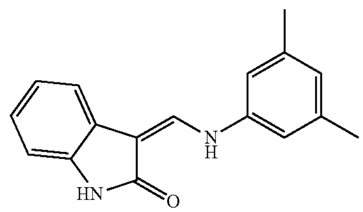 [SMILES: Cc1cc(C)cc(N/C=C2\C(=O)Nc3ccccc32)c1] | 10% | 32% |
| 15_24 | CHEMDIV | C285-0023 | 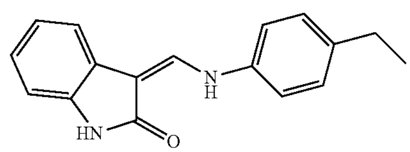 [SMILES: CCc1ccc(N/C=C2\C(=O)Nc3ccccc32)cc1] | 9% | 17% |
| 15_25 | CHEMDIV | C285-0050 | 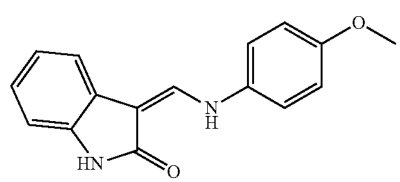 [SMILES: COc1ccc(N/C=C2\C(=O)Nc3ccccc32)cc1] | 9% | 16% |
| 15_26 | CHEMDIV | 5682-0149 | 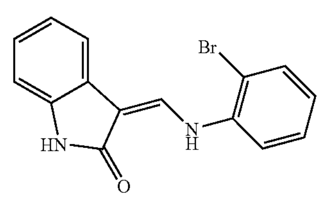 [SMILES: O=C1Nc2ccccc2/C1=C/Nc1ccccc1Br] | 8% | 8% |
| 15_27 | CHEMDIV | C285-0035 | 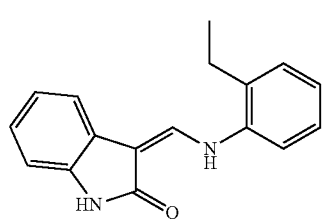 [SMILES: CCc1ccccc1N/C=C1\C(=O)Nc2ccccc21] | 8% >200 | 42% >200 |
| 15_28 | CHEMDIV | C285-0112 | 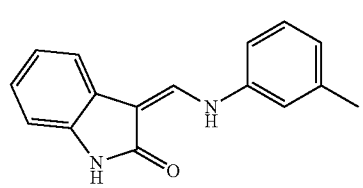 [SMILES: Cc1cccc(N/C=C2\C(=O)Nc3ccccc32)c1] | 8% >200 | 24% >200 |

TABLE 9-continued

| # | VENDOR | ID | STRUCTURE | INHIBITION (%) IC$_{50}$ (μM) E. coli | B. anthracis |
|---|---|---|---|---|---|
| 15_29 | CHEMDIV | C285-0107 | 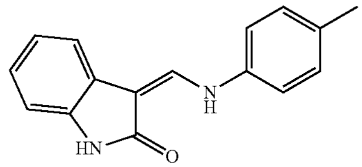 [SMILES: Cc1ccc(N/C=C2\C(=O)Nc3ccccc32)cc1] | 7% | 38% |
| 15_30 | CHEMDIV | C285-0078 | 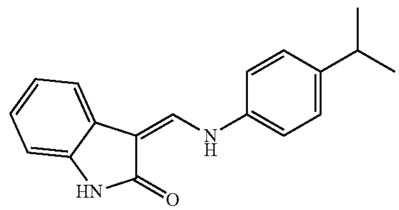 [SMILES: CC(C)c1ccc(N/C=C2\C(=O)Nc3ccccc32)cc1] | 7% | 42% |
| 15_31 | CHEMDIV | 5682-0010 | 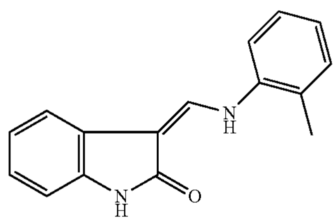 [SMILES: Cc1ccccc1N/C=C1\C(=O)Nc2ccccc21] | 7% 118 | 27% 112 |
| 15_32 | CHEMDIV | 5682-0009 | 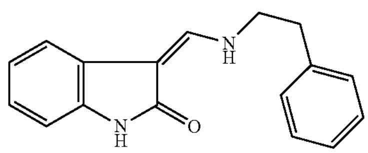 [SMILES: O=C1Nc2ccccc2/C1=C/NCCc1ccccc1] | 7% | 4% |
| 15_33 | CHEMDIV | 5682-0159 | 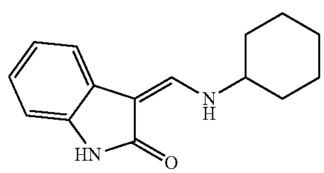 [SMILES: O=C1Nc2ccccc2/C1=C/NC1CCCCC1] | 6% | 15% |
| 15_34 | CHEMDIV | 5682-0160 | 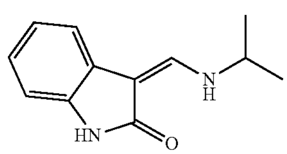 | 4% | 9% |
| 15_35 | CHEMDIV | C285-0072 | 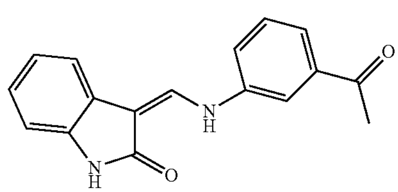 [SMILES: CC(=O)c1cccc(N/C=C2\C(=O)Nc3ccccc32)c1] | 4% | 19% |
| 15_36 | CHEMDIV | 5682-0154 | 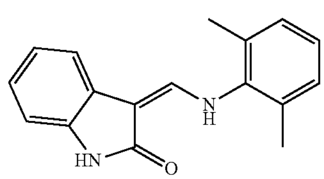 [SMILES: Cc1cccc(C)c1N/C=C1\C(=O)Nc2ccccc21] | 4% | 11% |

TABLE 9-continued

| # | VENDOR | ID | STRUCTURE | INHIBITION (%) IC$_{50}$ (µM) | |
|---|---|---|---|---|---|
| | | | | E. coli | B. anthracis |
| 15_37 | CHEMDIV | 5682-0148 | 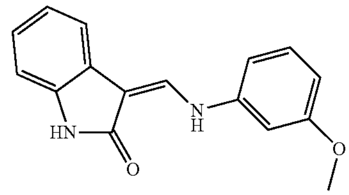 [SMILES: COc1cccc(N/C=C2\C(=O)Nc3ccccc32)c1] | 4% | 1% |
| 15_38 | CHEMDIV | 5682-0074 | 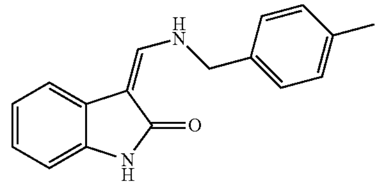 [SMILES: Cc1ccc(CN/C=C2\C(=O)Nc3ccccc32)cc1] | 3% | 17% |
| 15_39 | CHEMDIV | 5682-0077 | 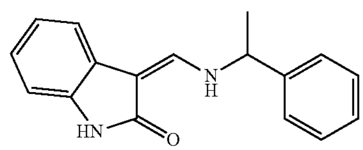 [SMILES: CC(N/C=C1\C(=O)Nc2ccccc21)c1ccccc1] | 3% | 18% |
| 15_40 | CHEMDIV | C285-0108 | 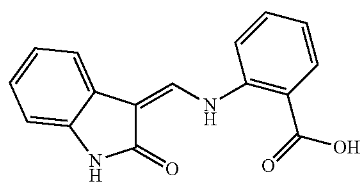 [SMILES: O=C1Nc2ccccc2/C1=C/Nc1ccccc1C(=O)O] | 1% | 0% |
| 15_41 | CHEMDIV | C285-0076 | 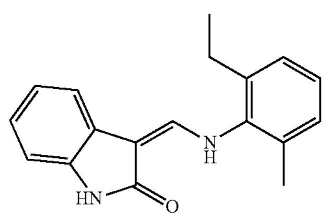 [SMILES: CCc1cccc(C)c1N/C=C1\C(=O)Nc2ccccc21] | 0% | 13% |
| 15_42 | CHEMDIV | 5682-0144 | 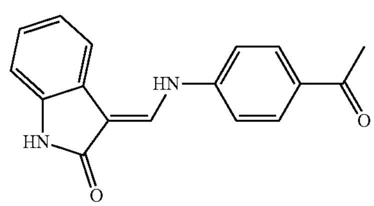 [SMILES: CC(=O)c1ccc(N/C=C2/C(=O)Nc3ccccc32)cc1] | 0% | 11% |

TABLE 10

| | NMNAT_X10_chemdiv039751_similar94 | COMP_NAME | IDNUMBER | MW | logP | 100 |
|---|---|---|---|---|---|---|
| 1 | | X10_chemdiv039751 | 8005-4955 | 474 | 6.17 | 1 |

TABLE 10-continued

| NMNAT_X10_chemdiv039751_similar94 | COMP_NAME | IDNUMBER | MW | logP | 100 |
|---|---|---|---|---|---|
| 2 | chembridge0164358 | 6048997 | 438 | 4.84 | 2 |
| 3 | chembridge018767 | 5247971 | 409 | 4.29 | 3 |
| 4 | chembridge048642 | 5478006 | 374 | 3.66 | 4 |
| 5 | chembridge048881 | 5479078 | 500 | 4.85 | 5 |
| 6 | chemdiv024765 | 8001-3249 | 450 | 5.28 | 6 |
| 7 | chemdiv028406 | 8002-2905 | 467 | 4.94 | 6 |
| 8 | chemdiv028415 | 8002-2934 | 388 | 4.1 | 6 |

TABLE 10-continued

| | NMNAT_X10_chemdiv039751_similar94 | COMP_NAME | IDNUMBER | MW | logP | 100 |
|---|---|---|---|---|---|---|
| 9 | | chemdiv0300479 | 8001-9257 | 413 | 5.49 | 9 |
| 10 | | chemdiv0303607 | 8003-8850 | 474 | 6.14 | 10 |
| 11 | | chemdiv0303616 | 8003-8866 | 409 | 4.29 | 3 |
| 12 | | chemdiv0304370 | 8004-3740 | 467 | 4.97 | 6 |
| 13 | | chemdiv031240 | 8003-0754 | 409 | 4.29 | 3 |
| 14 | | chemdiv032918 | 8003-6329 | 488 | 6.58 | 14 |

TABLE 10-continued

| NMNAT_X10_chemdiv039751_similar94 | COMP_NAME | IDNUMBER | MW | logP | 100 |
|---|---|---|---|---|---|
| 15 | chemdiv034066 | 8003-9695 | 430 | 5.97 | 15 |
| 16 | chemdiv034267 | 8004-0194 | 453 | 4.49 | 4 |
| 17 | chemdiv039712 | 8005-4902 | 374 | 3.7 | 4 |
| 18 | chemdiv039718 | 8005-4908 | 409 | 4.33 | 3 |
| 19 | chemdiv039747 | 8005-4949 | 500 | 4.89 | 5 |
| 20 | chemdiv043228 | 8006-3094 | 453 | 4.53 | 4 |
| 21 | chemdiv103114 | 1761-0568 | 392 | 3.85 | 21 |

TABLE 10-continued

| | NMNAT_X10_chemdiv039751_similar94 | COMP_NAME | IDNUMBER | MW | logP | 100 |
|---|---|---|---|---|---|---|
| 22 | | chemdiv103138 | 1761-0592 | 392 | 3.81 | 21 |
| 23 | | chemdiv103157 | 1761-0615 | 453 | 4.49 | 4 |
| 24 | | chemdiv103175 | 1761-0634 | 392 | 3.81 | 21 |
| 25 | | chemdiv103179 | 1761-0639 | 453 | 4.46 | 4 |

TABLE 10-continued

| NMNAT_X10_chemdiv039751_similar94 | COMP_NAME | IDNUMBER | MW | logP | 100 |
|---|---|---|---|---|---|
| 26 | chemdiv103184 | 1761-0644 | 400 | 4.3 | 26 |
| 27 | chemdiv103189 | 1761-0651 | 467 | 4.38 | 27 |
| 28 | chemdiv103198 | 1761-0662 | 388 | 3.99 | 27 |
| 29 | chemdiv103218 | 1761-0686 | 388 | 3.96 | 27 |
| 30 | chemdiv103453 | 1761-1053 | 500 | 4.89 | 5 |

TABLE 10-continued
| | NMNAT_X10_chemdiv039751_similar94 | COMP_NAME | IDNUMBER | MW | logP | 100 |
|---|---|---|---|---|---|---|
| 31 | 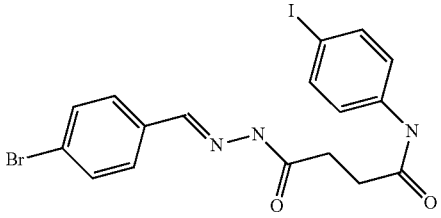 [SMILES: O=C(CCC(=O)Nc1ccc(I)cc1)N/N=C/c1ccc(Br)cc1] | chemdiv103475 | 1761-1076 | 500 | 4.85 | 5 |
| 32 | 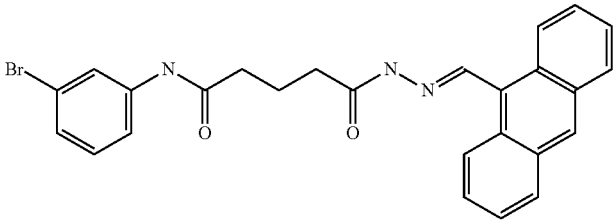 [SMILES: O=C(CCCC(=O)Nc1cccc(Br)c1)N/N=C/c1c2ccccc2cc2ccccc12] | mdd0529597 | APX000031595 | 483 | 6.62 | 14 |
| 33 | 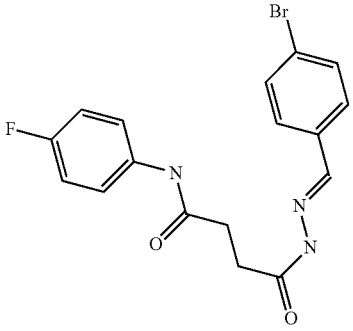 [SMILES: O=C(CCC(=O)Nc1ccc(F)cc1)N/N=C/c1ccc(Br)cc1] | nanosyn002233 | NS50906 | 392 | 3.81 | 21 |
| 34 | 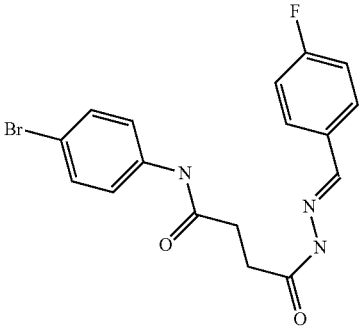 [SMILES: O=C(CCC(=O)Nc1ccc(Br)cc1)N/N=C/c1ccc(F)cc1] | nanosyn002254 | NS50927 | 392 | 3.81 | 21 |
| 35 | 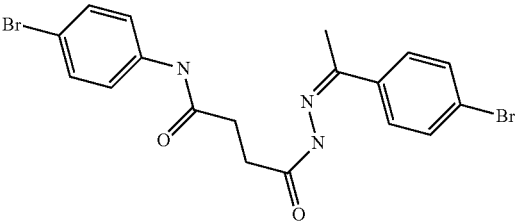 [SMILES: C/C(=N/NC(=O)CCC(=O)Nc1ccc(Br)cc1)c1ccc(Br)cc1] | nanosyn002268 | NS50941 | 467 | 4.38 | 27 |

TABLE 10-continued

| NMNAT_X10_chemdiv039751_similar94 | COMP_NAME | IDNUMBER | MW | logP | 100 |
|---|---|---|---|---|---|
| 36 | specs4019514 | AG-205/07767026 | 392 | 3.85 | 21 |
| 37 | specs4028799 | AG-205/32429038 | 521 | 6.53 | 37 |

TABLE 11

| NMNAT_C11_specs0182670_similar97 | COMP_NAME | IDNUMBER | MW | logP | 100 |
|---|---|---|---|---|---|
| 1 | C11_specs0182670 | AM-807/13614701 | 399 | 3.6 | 1 |
| 2 | chembridge0290293 | 7122170 | 420 | 4.8 | 2 |
| 3 | chembridge0388471 | 7904181 | 363 | 4.19 | 3 |

TABLE 11-continued

| NMNAT_C11_specs0182670_similar97 | COMP_NAME | IDNUMBER | MW | logP | 100 |
|---|---|---|---|---|---|
| 4 | chemdiv044455 | 8006-8558 | 363 | 4.22 | 3 |
| 5 | chemdiv4035313 | 5350-0016 | 387 | 3.92 | 3 |
| 6 | chemdiv4035318 | 5350-0029 | 369 | 3.77 | 3 |
| 7 | chemdiv4035329 | 5350-0047 | 382 | 3.16 | 3 |
| 8 | chemdiv4035410 | 5350-0377 | 387 | 3.92 | 3 |

TABLE 11-continued
| | NMNAT_C11_specs0182670_similar97 | COMP_NAME | IDNUMBER | MW | logP | 100 |
|---|---|---|---|---|---|---|
| 9 | 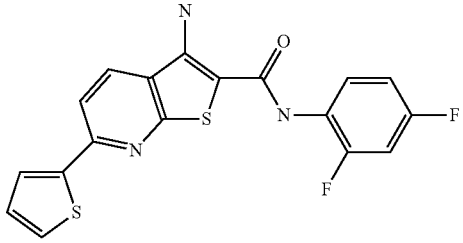 [SMILES: Nc1c(C(=O)Nc2ccc(F)cc2F)sc2nc(-c3cccs3)ccc12] | chemdiv4035411 | 5350-0378 | 387 | 3.92 | 3 |
| 10 | 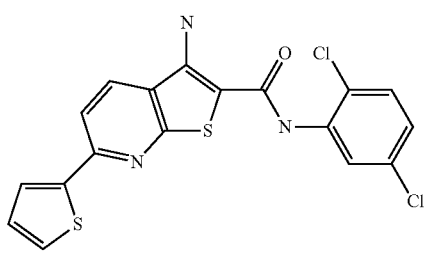 [SMILES: Nc1c(C(=O)Nc2cc(Cl)ccc2Cl)sc2nc(-c3cccs3)ccc12] | specs0182556 | AM-807/13614315 | 420 | 4.8 | 2 |
| 11 | 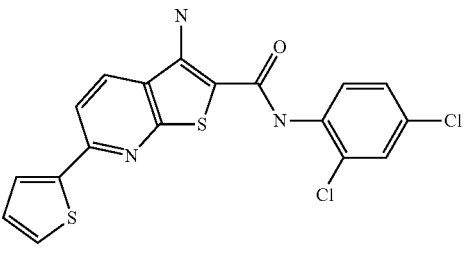 [SMILES: Nc1c(C(=O)Nc2ccc(Cl)cc2Cl)sc2nc(-c3cccs3)ccc12] | specs0182559 | AM-807/13614318 | 420 | 4.8 | 2 |
| 12 | 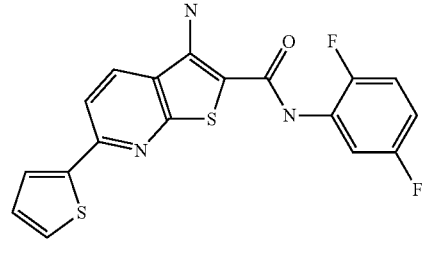 [SMILES: Nc1c(C(=O)Nc2cc(F)ccc2F)sc2nc(-c3cccs3)ccc12] | specs0182568 | AM-807/13614342 | 387 | 3.92 | 3 |
| 13 | 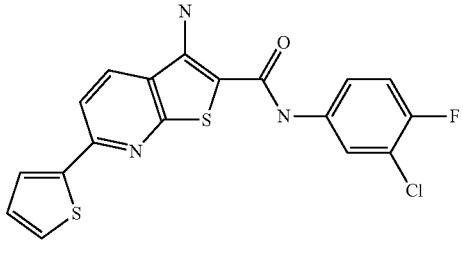 [SMILES: Nc1c(C(=O)Nc2ccc(F)c(Cl)c2)sc2nc(-c3cccs3)ccc12] | specs0182571 | AM-807/13614349 | 404 | 4.36 | 1 |
| 14 | 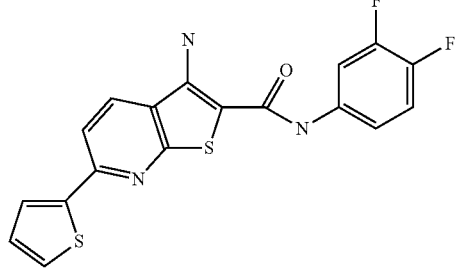 | specs0182576 | AM-807/13614357 | 387 | 3.92 | 3 |

TABLE 11-continued

| NMNAT_C11_specs0182670_similar97 | COMP_NAME | IDNUMBER | MW | logP | 100 |
|---|---|---|---|---|---|
| 15 | specs0182578 | AM-807/13614362 | 404 | 4.36 | 1 |
| 16 | specs0182588 | AM-807/13614398 | 387 | 3.92 | 3 |
| 17 | specs0182592 | AM-807/13614404 | 420 | 4.76 | 2 |
| 18 | specs0182593 | AM-807/13614405 | 420 | 4.87 | 2 |
| 19 | specs0182647 | AM-807/13614663 | 415 | 4.03 | 2 |
| 20 | specs0182651 | AM-807/13614667 | 415 | 4.03 | 2 |

TABLE 11-continued
| NMNAT_C11_specs0182670_similar97 | | COMP_NAME | IDNUMBER | MW | logP | 100 |
|---|---|---|---|---|---|---|
| 21 | 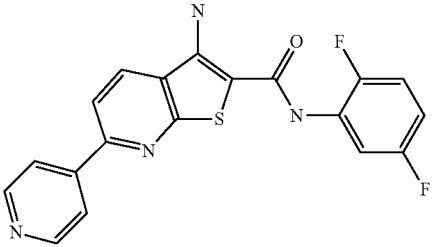 [SMILES: Nc1c(C(=O)Nc2cc(F)ccc2F)sc2nc(-c3ccncc3)ccc12] | specs0182666 | AM-807/13614694 | 382 | 3.16 | 3 |
| 22 | 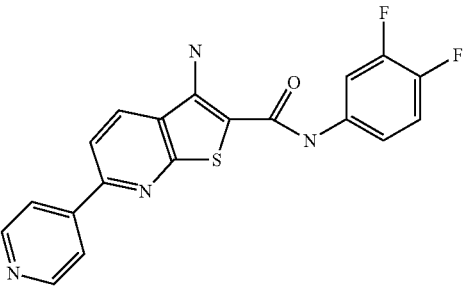 [SMILES: Nc1c(C(=O)Nc2ccc(F)c(F)c2)sc2nc(-c3ccncc3)ccc12] | specs0182675 | AM-807/13614710 | 382 | 3.16 | 3 |
| 23 | 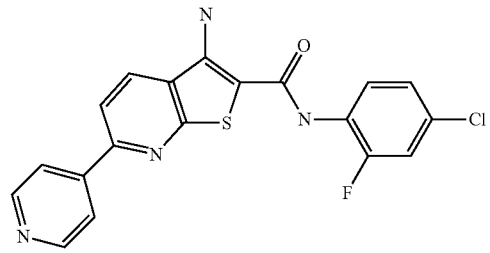 [SMILES: Nc1c(C(=O)Nc2ccc(Cl)cc2F)sc2nc(-c3ccncc3)ccc12] | specs0182676 | AM-807/13614715 | 399 | 3.6 | 1 |
| 24 | 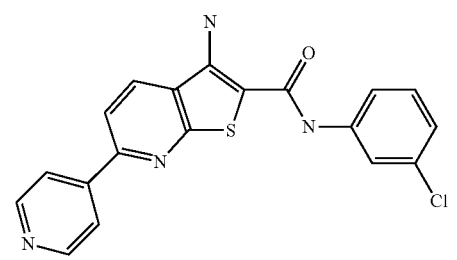 [SMILES: Nc1c(C(=O)Nc2cccc(Cl)c2)sc2nc(-c3ccncc3)ccc12] | specs0182690 | AM-807/13614744 | 381 | 3.44 | 2 |
| 25 | 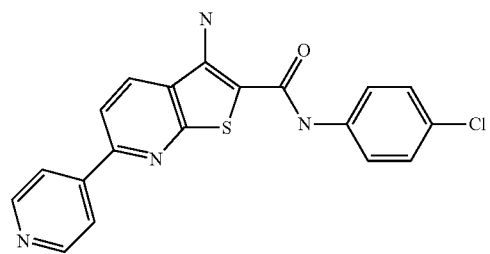 [SMILES: Nc1c(C(=O)Nc2ccc(Cl)cc2)sc2nc(-c3ccncc3)ccc12] | specs0182691 | AM-807/13614745 | 381 | 3.41 | 2 |
| 26 | 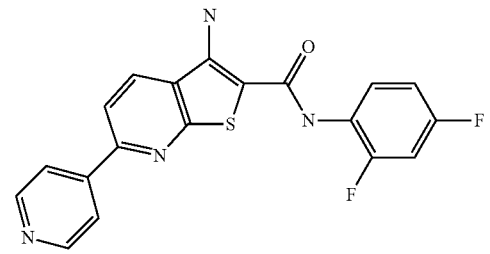 [SMILES: Nc1c(C(=O)Nc2ccc(F)cc2F)sc2nc(-c3ccncc3)ccc12] | specs0182695 | AM-807/13614751 | 382 | 3.16 | 3 |

TABLE 11-continued
| NMNAT_C11_specs0182670_similar97 | | COMP_NAME | IDNUMBER | MW | logP | 100 |
|---|---|---|---|---|---|---|
| 27 | 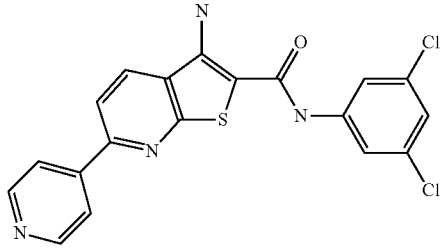 [SMILES: Nc1c(C(=O)Nc2cc(Cl)cc(Cl)c2)sc2nc(-c3ccncc3)ccc12] | specs0182698 | AM-807/13614758 | 415 | 4.11 | 2 |
| 28 | 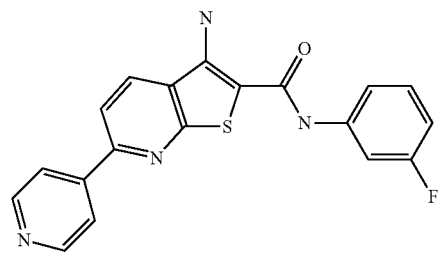 [SMILES: Nc1c(C(=O)Nc2cccc(F)c2)sc2nc(-c3ccncc3)ccc12] | specs0182702 | AM-807/13614764 | 364 | 3.01 | 3 |
| 29 | 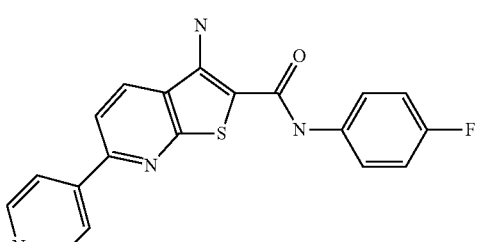 | specs0182703 | AM-807/13614765 | 364 | 2.97 | 3 |
| 30 | 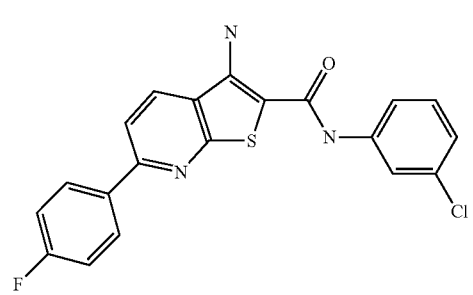 [SMILES: Nc1c(C(=O)Nc2cccc(Cl)c2)sc2nc(-c3ccc(F)cc3)ccc12] | specs0182886 | AM-807/13615708 | 398 | 4.83 | 1 |
| 31 | 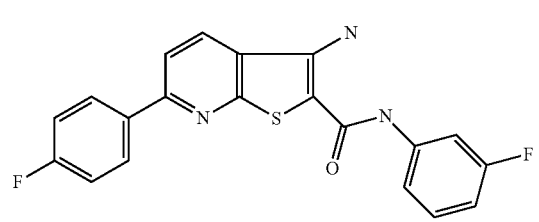 [SMILES: Nc1c(C(=O)Nc2cccc(F)c2)sc2nc(-c3ccc(F)cc3)ccc12] | specs4108874 | AM-807/12740165 | 381 | 4.39 | 3 |
| 32 | 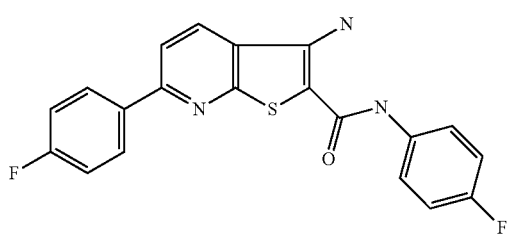 [SMILES: Nc1c(C(=O)Nc2ccc(F)cc2)sc2nc(-c3ccc(F)cc3)ccc12] | specs4108875 | AM-807/12740168 | 381 | 4.35 | 3 |

TABLE 11-continued

| NMNAT_C11_specs0182670_similar97 | COMP_NAME | IDNUMBER | MW | logP | 100 |
|---|---|---|---|---|---|
| 33 | specs4109084 | AM-807/13614391 | 386 | 4.21 | 2 |
| 34 | specs4109174 | AM-807/13615660 | 416 | 4.98 | 1 |
| 35 | specs4109176 | AM-807/13615668 | 399 | 4.54 | 3 |
| 36 | specs4109178 | AM-807/13615674 | 416 | 4.98 | 1 |
| 37 | specs4109179 | AM-807/13615675 | 416 | 4.98 | 1 |

TABLE 11-continued
| NMNAT_C11_specs0182670_similar97 | | COMP_NAME | IDNUMBER | MW | logP | 100 |
|---|---|---|---|---|---|---|
| 38 | | specs4109183 | AM-807/13615709 | 398 | 4.79 | 1 |
| 39 | | specs4109354 | AM-807/14147089 | 415 | 3.99 | 2 |
| 40 | | timtt5025068 | ST5025068 | 415 | 4 | 2 |
TABLE 12
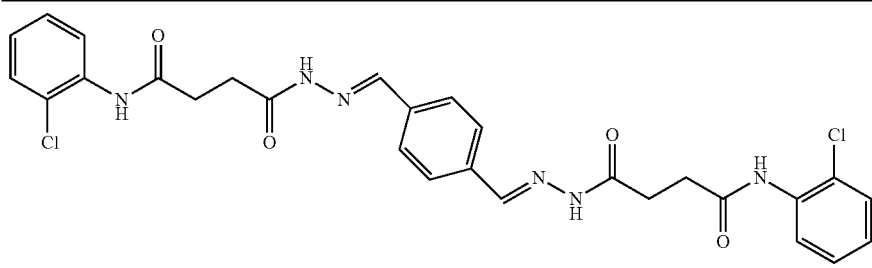
RK-AL-1

TABLE 12-continued
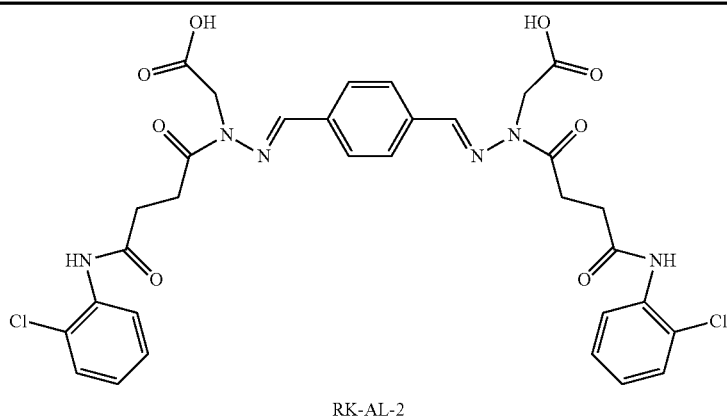
RK-AL-2
RK-AL-3
TABLE 13
Chemical structures of two classes of bacterial NadD inhibitors as represented by compounds 1_02 and 3_02[a]
| Compound class | Structure |
|---|---|
| 1 | 1_02 |
| 3 | 3_02 |
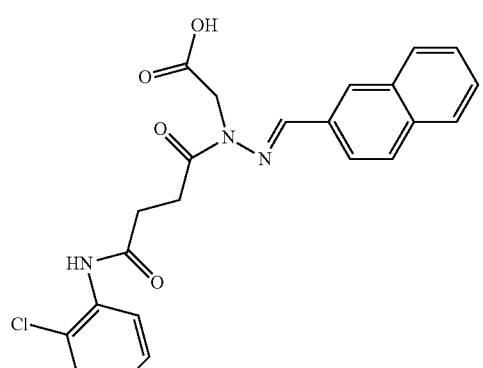
[a] The numbering of the compounds follows the scheme:
compound class_1$^{st}$ generation analog_2$^{nd}$ generation analog.

TABLE 14

| Crystal Data and refinement statistics | | | |
|---|---|---|---|
| Datasets | baNadD-1__02 | baNadD•1__02__1 | baNadD 1__02__03 |
| Data Statistics | | | |
| Space group | $P2_12_12$ | $P2_12_12$ | C2 |
| Unit cell Dimensions | a = 88.6 Å, | a = 88.34 | a = 295.15 Å, |
| | b = 97.53 Å, | Å, b = 96.64 | b = 46.45 Å, |
| | c = 44.30 Å | Å, c = 44.13 Å | c = 114.95 Å, |
| | | | β = 91.42° |
| Resolution (Å) | 50-1.70 | 50-1.80 | 50-2.55 |
| Total observations | 230680 | 73589 | 191091 |
| Unique Reflections | 74116 | 47493 | 97476 |
| Completeness (outershell) (%) | 99.0 (97.0) | 88.8 (79.3) | 99.6 (100) |
| $R_{sym}$ (outer shell) | 0.040 (0.574) | 0.040 (0.271) | 0.075/0.571 |
| I/δ (outer shell) | 39.2 (2.6) | 23.8 (2.7) | 20.53/2.06 |
| Refinement | | | |
| $R_{work}^{b}$ | 0.190 | 0.183 | 0.205 |
| $R_{free}^{c}$ | 0.230 | 0.232 | 0.270 |
| r.m.s.d bond length (Å) | 0.006 | 0.007 | 0.008 |
| r.m.s.d bond angle (°) | 1.049 | 1.121 | 1.073 |
| Protein atoms | 3051 | 3067 | 11783 |
| Water molecules | 308 | 337 | 232 |
| Ligand atoms | 85 | 48 | 191 |
| Average B-factors (Å$^2$) | | | |
| Protein | 32.5 | 26.3 | 57.31 |
| ligands | 39.7 | 24.6 | 67.81 |
| water | 32.6 | 33.2 | 44.19 |
| Ramachandran Plot | | | |
| Favored region (%) | 98.6 | 98.6 | 97.4 |
| Allowed region (%) | 100.0 | 100.0 | 99.8 |

$^{a}R_{sym} = \Sigma_{hkl}\Sigma_j|I_j - <I>|/\Sigma_{hkl}\Sigma_j|I_j|$.
$^{b}R_{work} = \Sigma_{hkl}|F_o - F_c|/\Sigma_{hkl}|F_o|$, where $F_o$ and $F_c$ are the observed and calculated structure factors, respectively.
$^{c}$Five percent randomly selected reflections were excluded from refinement and used in the calculation of $R_{free}$.

While detailed embodiments have been used to illustrate the present invention, to those skilled in the art, however, it will be apparent from the foregoing disclosure that various changes and modifications can be made therein without departing from the spirit and scope of the invention. Furthermore, the foregoing description of the embodiments according to the present invention is provided for illustration only, and is not intended to limit the invention.

We claim:

1. A pharmaceutical composition comprising Compound 01__02 as an active ingredient and a pharmaceutically acceptable carrier or excipient:

01_02

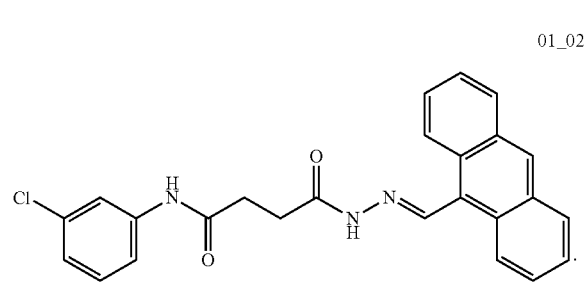 [SMILES: O=C(CCC(=O)Nc1cccc(Cl)c1)N/N=C/c1c2ccccc2cc2ccccc12]

2. The pharmaceutical composition of claim 1, wherein said Compound 01__02 inhibits bacterial nicotinate mononucleotide adenylyltransferase activity in a subject.

3. A method of treating a bacterial infection in a subject in need thereof, comprising administering a therapeutically effective amount the pharmaceutical composition of claim 1 to said subject, wherein said bacterial infection is at least one selected from the group consisting of *Escherichia coli*, *Bacillus anthracis*, *B. anthracis* sterne, *B. subtilis*, *S. aureus* (MRSA) strain, Vancomycin and vancomycin-resistant *enterococci* (VRE), and *Streptococcus pneumonia*.

4. A pharmaceutical composition comprising at least one compound of Formula 1 as an active ingredient and a pharmaceutically acceptable carrier or excipient:

Formula 1

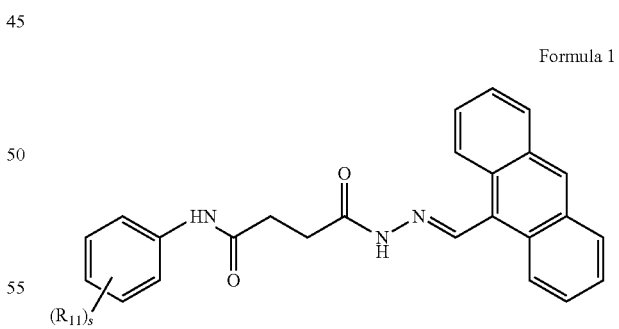

wherein each $R_{11}$ is independently selected from the group consisting of halogen and alkyl and s is an integer from 0 to 5.

5. The pharmaceutical composition of claim 4, wherein said compound of Formula I inhibits bacterial nicotinate mononucleotide adenylyltransferase activity in a subject.

6. A method of treating a bacterial infection in a subject in need thereof, comprising administering a therapeutically effective amount the pharmaceutical composition of claim 4 to said subject, wherein said bacterial infection is at least one selected from the group consisting of *Escherichia coli, Bacillus anthracis, B. anthracis* sterne, *B. subtilis, S. aureus* (MRSA) strain, Vancomycin and vancomycin-resistant enterococci (VRE), and *Streptococcus pneumonia*.

* * * * *